US012788872B2

(12) United States Patent
Rubalcaba, Jr. et al.

(10) Patent No.: US 12,788,872 B2
(45) Date of Patent: Nov. 10, 2026

(54) INFUSION PUMP WITH CRITICAL CARE AREA AND DRUG LIBRARY SETTINGS

(71) Applicant: ICU Medical, Inc., San Clemente, CA (US)

(72) Inventors: Bernardino Rubalcaba, Jr., Escondido, CA (US); Mihaela Cozmi, Gilroy, CA (US); Glenn Davis, Grayslake, IL (US); Angela LeCaptain, Silver Lake, WI (US); Angela Marino, Deerfield, IL (US); Raymond P. Silkaitis, Lake Forest, IL (US); H. Clay Teel, IV, San Diego, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 19/458,557

(22) Filed: Jan. 23, 2026

(65) Prior Publication Data

US 2026/0151559 A1 Jun. 4, 2026

Related U.S. Application Data

(63) Continuation of application No. 17/814,123, filed on Jul. 21, 2022, now abandoned, which is a (Continued)

(51) Int. Cl.
*G06F 8/60* (2018.01)
*A61M 5/142* (2006.01)

(Continued)

(52) U.S. Cl.
CPC .......... *A61M 5/14212* (2013.01); *G06F 8/60* (2013.01); *G16H 20/17* (2018.01);

(Continued)

(58) Field of Classification Search
CPC .......... A61M 5/142; A61M 2205/505; A61M 5/14212; A61M 5/14228; A61M 5/14232;

(Continued)

(56) References Cited

U.S. PATENT DOCUMENTS

| | | | |
|---|---|---|---|
| 3,401,337 | A | 9/1968 | Beusman et al. |
| 3,484,681 | A | 12/1969 | Grady, Jr. et al. |

(Continued)

FOREIGN PATENT DOCUMENTS

| | | |
|---|---|---|
| AU | 2013216679 | 9/2013 |
| BR | PI0704229-9 | 11/2009 |

(Continued)

OTHER PUBLICATIONS

Braun, "Infusomat® Space and Accessories", Instructions for Use, Nov. 2010, pp. 68. <http://corp.bbraun.ee/Extranet/Infusionipumbad/Kasutusjuhendid/Vanad/Kasutusjuhend-Infusomat_Space(vers688J,inglise_k).pdf>.

(Continued)

*Primary Examiner* — Phenuel S Salomon
(74) *Attorney, Agent, or Firm* — KNOBBE MARTENS OLSON & BEAR LLP

(57) ABSTRACT

A method and system is disclosed for operating a medical device with or without a cassette in place. A method is disclosed for adding additional VTBI to an ongoing infusion without stopping the infusion and with maintaining the infusion parameters. A method and system is disclosed for changing the CCA without having to interrupt or completely stop an ongoing infusion. Quick titration buttons are provided to allow improved navigation between various delivery display screens.

29 Claims, 41 Drawing Sheets

Related U.S. Application Data continuation of application No. 16/859,837, filed on Apr. 27, 2020, now Pat. No. 11,395,875, which is a continuation of application No. 12/337,803, filed on Dec. 18, 2008, now Pat. No. 10,635,784.

(60) Provisional application No. 61/014,677, filed on Dec. 18, 2007.

(51) Int. Cl.
*G16H 20/17* (2018.01)
*A61M 5/145* (2006.01)
*G16H 70/40* (2018.01)

(52) U.S. Cl.
CPC ..... *A61M 5/14228* (2013.01); *A61M 5/14232* (2013.01); *A61M 5/1452* (2013.01); *A61M 2205/3561* (2013.01); *A61M 2205/3592* (2013.01); *A61M 2205/505* (2013.01); *G06T 2200/24* (2013.01); *G06T 2219/2016* (2013.01); *G16H 70/40* (2018.01); *Y10S 128/06* (2013.01)

(58) Field of Classification Search
CPC ........ A61M 5/1452; A61M 2205/3561; A61M 2205/3592; G06F 8/60; G16H 20/17; G16H 70/40; G06T 2200/24; G06T 2219/2016; Y10S 128/06
See application file for complete search history.

(56) References Cited

U.S. PATENT DOCUMENTS

| | | | |
|---|---|---|---|
| 3,699,320 | A | 10/1972 | Zimmerman et al. |
| 3,727,074 | A | 4/1973 | Keller et al. |
| 3,731,679 | A | 5/1973 | Wilhelmson et al. |
| 3,768,084 | A | 10/1973 | Haynes |
| 3,770,354 | A | 11/1973 | Tsuruta et al. |
| 3,778,702 | A | 12/1973 | Finger |
| 3,806,821 | A | 4/1974 | Niemeyer et al. |
| 3,838,565 | A | 10/1974 | Carlyle |
| 3,847,138 | A | 11/1974 | Gollub |
| 3,854,038 | A | 12/1974 | McKinley |
| 3,858,815 | A | 1/1975 | Black |
| 3,886,459 | A | 5/1975 | Hufford et al. |
| 3,890,554 | A | 6/1975 | Yoshitake et al. |
| 3,894,431 | A | 7/1975 | Muston et al. |
| 3,898,637 | A | 8/1975 | Wolstenholme |
| 3,901,231 | A | 8/1975 | Olson |
| 3,909,693 | A | 9/1975 | Yoshitake et al. |
| 3,910,701 | A | 10/1975 | Henderson |
| 3,911,343 | A | 10/1975 | Oster |
| 3,919,608 | A | 11/1975 | Usami et al. |
| 3,921,622 | A | 11/1975 | Cole |
| 3,930,404 | A | 1/1976 | Ryden, Jr. |
| 3,933,431 | A | 1/1976 | Trujillo et al. |
| 3,935,876 | A | 2/1976 | Massie et al. |
| 3,944,963 | A | 3/1976 | Hively |
| 3,966,358 | A | 6/1976 | Heimes et al. |
| 3,971,980 | A | 7/1976 | Jungfer et al. |
| 3,974,681 | A | 8/1976 | Namery |
| 3,974,683 | A | 8/1976 | Martin |
| 3,985,467 | A | 10/1976 | Lefferson |
| 3,990,444 | A | 11/1976 | Vial |
| 3,997,888 | A | 12/1976 | Kremer |
| 4,005,724 | A | 2/1977 | Courtot |
| 4,014,206 | A | 3/1977 | Taylor |
| 4,038,982 | A | 8/1977 | Burke |
| 4,039,269 | A | 8/1977 | Pickering |
| 4,048,474 | A | 9/1977 | Olesen |
| 4,049,954 | A | 9/1977 | Da Costa Vieira et al. |
| 4,055,175 | A | 10/1977 | Clemens et al. |
| 4,057,228 | A | 11/1977 | Völker et al. |
| 4,068,521 | A | 1/1978 | Cosentino et al. |
| 4,078,562 | A | 3/1978 | Friedman |
| 4,089,227 | A | 5/1978 | Falgari et al. |
| 4,094,318 | A | 6/1978 | Burke |
| 4,105,028 | A | 8/1978 | Sadlier et al. |
| 4,114,144 | A | 9/1978 | Hyman |
| 4,151,845 | A | 5/1979 | Clemens |
| 4,155,362 | A | 5/1979 | Jess |
| 4,164,986 | A | 8/1979 | Eloy |
| 4,173,224 | A | 11/1979 | Marx |
| 4,181,610 | A | 1/1980 | Shintani et al. |
| 4,183,244 | A | 1/1980 | Kohno et al. |
| 4,195,515 | A | 4/1980 | Smoll |
| 4,210,138 | A | 7/1980 | Jess et al. |
| 4,213,454 | A | 7/1980 | Shim |
| 4,217,993 | A | 8/1980 | Jess et al. |
| 4,240,294 | A | 12/1980 | Grande |
| 4,240,438 | A | 12/1980 | Updike et al. |
| 4,244,365 | A | 1/1981 | McGill |
| 4,256,437 | A | 3/1981 | Brown |
| 4,261,356 | A | 4/1981 | Turner et al. |
| 4,264,861 | A | 4/1981 | Radu et al. |
| 4,265,240 | A | 5/1981 | Jenkins |
| 4,270,532 | A | 6/1981 | Franetzki et al. |
| 4,277,226 | A | 7/1981 | Archibald et al. |
| 4,278,085 | A | 7/1981 | Shim |
| 4,280,495 | A | 7/1981 | Lampert |
| 4,282,872 | A | 8/1981 | Franetzki et al. |
| 4,286,202 | A | 8/1981 | Clancy et al. |
| 4,290,346 | A | 9/1981 | Bujan |
| 4,291,692 | A | 9/1981 | Bowman et al. |
| 4,292,405 | A | 9/1981 | Mascoli |
| 4,298,357 | A | 11/1981 | Permic |
| 4,308,866 | A | 1/1982 | Jeliffe |
| 4,312,341 | A | 1/1982 | Zissimopoulos et al. |
| 4,319,568 | A | 3/1982 | Tregoning |
| 4,322,201 | A | 3/1982 | Archibald |
| 4,323,849 | A | 4/1982 | Smith |
| 4,324,662 | A | 4/1982 | Schnell |
| 4,328,800 | A | 5/1982 | Marx |
| 4,328,801 | A | 5/1982 | Marx |
| 4,333,045 | A | 6/1982 | Oltendorf |
| 4,343,316 | A | 8/1982 | Jespersen |
| 4,344,429 | A | 8/1982 | Gupton et al. |
| 4,346,707 | A | 8/1982 | Whitney et al. |
| 4,360,019 | A | 11/1982 | Portner et al. |
| 4,366,384 | A | 12/1982 | Jensen |
| 4,367,736 | A | 1/1983 | Gupton |
| 4,370,983 | A | 2/1983 | Lichtenstein et al. |
| 4,373,527 | A | 2/1983 | Fischell |
| 4,379,452 | A | 4/1983 | DeVries |
| 4,381,005 | A | 4/1983 | Bujan |
| 4,384,578 | A | 5/1983 | Winkler |
| 4,385,247 | A | 5/1983 | Satomi |
| 4,391,598 | A | 7/1983 | Thompson |
| 4,392,849 | A | 7/1983 | Petre et al. |
| 4,394,862 | A | 7/1983 | Shim |
| 4,395,259 | A | 7/1983 | Prestele et al. |
| 4,397,194 | A | 8/1983 | Soltz |
| 4,399,362 | A | 8/1983 | Cormier et al. |
| 4,407,659 | A | 10/1983 | Adam |
| 4,411,651 | A | 10/1983 | Schulman |
| 4,418,565 | A | 12/1983 | St. John |
| 4,432,699 | A | 2/1984 | Beckman et al. |
| 4,432,761 | A | 2/1984 | Dawe |
| 4,432,762 | A | 2/1984 | Dawe |
| 4,443,218 | A | 4/1984 | Decant, Jr. et al. |
| 4,444,546 | A | 4/1984 | Pazemenas |
| 4,447,191 | A | 5/1984 | Bilstad et al. |
| 4,447,224 | A | 5/1984 | Decant, Jr. et al. |
| 4,453,931 | A | 6/1984 | Pastrone |
| 4,457,751 | A | 7/1984 | Rodler |
| 4,463,301 | A | 7/1984 | Moriguchi et al. |
| 4,464,170 | A | 8/1984 | Clemens |
| 4,467,654 | A | 8/1984 | Murakami et al. |
| 4,468,222 | A | 8/1984 | Lundquist |
| 4,468,601 | A | 8/1984 | Chamran et al. |
| 4,469,481 | A | 9/1984 | Kobayashi |
| 4,475,666 | A | 10/1984 | Bilbrey et al. |
| 4,475,901 | A | 10/1984 | Kraegen et al. |

(56) References Cited

U.S. PATENT DOCUMENTS 4,477,756 A 10/1984 Moriguchi
4,479,760 A 10/1984 Bilstad et al.
4,480,218 A 10/1984 Hair
4,480,483 A 11/1984 McShane
4,483,202 A 11/1984 Ogua et al.
4,487,601 A 12/1984 Lindemann
4,492,909 A 1/1985 Hartwig
4,496,346 A 1/1985 Mosteller
4,498,843 A 2/1985 Schneider et al.
4,501,531 A 2/1985 Bilstad et al.
4,504,263 A 3/1985 Steuer
4,507,112 A 3/1985 Hillel
4,510,266 A 4/1985 Eertink
4,513,796 A 4/1985 Miller et al.
4,515,584 A 5/1985 Abe et al.
4,519,792 A 5/1985 Dawe
4,521,212 A 6/1985 Ruschke
4,525,163 A 6/1985 Slavik et al.
4,526,568 A 7/1985 Clemens et al.
4,526,574 A 7/1985 Pekkarinen
4,529,401 A 7/1985 Leslie et al.
4,533,350 A 8/1985 Danby et al.
4,543,955 A 10/1985 Schroeppel
4,551,134 A 11/1985 Slavik et al.
4,553,958 A 11/1985 LeCocq
4,559,036 A 12/1985 Wunsch
4,559,037 A 12/1985 Franetzki et al.
4,559,044 A 12/1985 Robinson
4,559,454 A 12/1985 Kramer
4,565,500 A 1/1986 Jeensalute et al.
4,583,981 A 4/1986 Urquhart et al.
4,587,473 A 5/1986 Turvey
4,607,520 A 8/1986 Dam
4,617,014 A 10/1986 Cannon et al.
4,624,661 A 11/1986 Arimond
4,627,835 A 12/1986 Fenton, Jr.
4,633,878 A 1/1987 Bombardieri
4,634,426 A 1/1987 kamen
4,634,427 A 1/1987 Hannula et al.
4,636,144 A 1/1987 Abe et al.
4,637,813 A 1/1987 DeVries
4,645,489 A 2/1987 Krumme
4,648,869 A 3/1987 Bobo, Jr.
4,652,260 A 3/1987 Fenton, Jr. et al.
4,658,244 A 4/1987 Meijer
4,668,216 A 5/1987 Martin
4,668,945 A 5/1987 Aldrovandi et al.
4,673,334 A 6/1987 Allington et al.
4,673,389 A 6/1987 Archibald et al.
4,676,776 A 6/1987 Howson et al.
4,677,359 A 6/1987 Enami et al.
4,678,979 A 7/1987 Hori
4,678,998 A 7/1987 Muramatsu
4,679,562 A 7/1987 Luksha
4,683,428 A 7/1987 Gete
4,685,903 A 8/1987 Cable et al.
4,690,673 A 9/1987 Blomquist
4,691,153 A 9/1987 Nishimura
4,692,145 A 9/1987 Weyant
4,696,671 A 9/1987 Epstein et al.
4,697,129 A 9/1987 Enami et al.
4,702,675 A 10/1987 Aldrovandi et al.
4,705,506 A 11/1987 Archibald et al.
4,710,106 A 12/1987 Iwata et al.
4,714,462 A 12/1987 DiDomenico
4,714,463 A 12/1987 Archibald et al.
4,718,576 A 1/1988 Tamura et al.
4,720,636 A 1/1988 Benner
4,722,224 A 2/1988 Scheller et al.
4,722,734 A 2/1988 Kolin
4,731,051 A 3/1988 Fischell
4,731,057 A 3/1988 Tanaka et al.
4,737,711 A 4/1988 O'Hare
4,739,346 A 4/1988 Buckley
4,741,732 A 5/1988 Crankshaw et al.
4,741,736 A 5/1988 Brown
4,748,857 A 6/1988 Nakagawa
4,751,445 A 6/1988 Sakai
4,756,706 A 7/1988 Kerns et al.
4,758,228 A 7/1988 Williams
4,763,525 A 8/1988 Cobb
4,764,166 A 8/1988 Spani et al.
4,764,697 A 8/1988 Christiaens
4,769,001 A 9/1988 Prince
4,776,842 A 10/1988 Franetzki et al.
4,781,687 A 11/1988 Wall
4,784,576 A 11/1988 Bloom et al.
4,785,184 A 11/1988 Bien et al.
4,785,799 A 11/1988 Schoon et al.
4,785,969 A 11/1988 McLaughlin
4,786,800 A 11/1988 Kamen
4,789,014 A 12/1988 DiGianfilippo
4,797,655 A 1/1989 Orndal et al.
4,803,389 A 2/1989 Ogawa et al.
4,803,625 A 2/1989 Fu et al.
4,818,186 A 4/1989 Pastrone et al.
4,820,281 A 4/1989 Lawler
4,821,558 A 4/1989 Pastrone et al.
4,828,545 A 5/1989 Epstein et al.
4,828,693 A 5/1989 Lindsay
4,829,448 A 5/1989 Balding et al.
4,838,856 A 6/1989 Mulreany et al.
4,838,857 A 6/1989 Strowe et al.
4,840,542 A 6/1989 Abbott
4,842,584 A 6/1989 Pastrone et al.
4,845,487 A 7/1989 Frantz et al.
4,846,792 A 7/1989 Bobo et al.
4,850,805 A 7/1989 Madsen et al.
4,851,755 A 7/1989 Fincher
4,854,324 A 8/1989 Hirschman et al.
4,856,339 A 8/1989 Williams
4,857,048 A 8/1989 Simons et al.
4,857,050 A 8/1989 Lentz et al.
4,858,154 A 8/1989 Anderson et al.
4,863,425 A 9/1989 Slate et al.
4,865,584 A 9/1989 Epstein et al.
4,869,722 A 9/1989 Heyman
4,874,359 A 10/1989 White et al.
4,878,175 A 10/1989 Norden-Paul et al.
4,881,413 A 11/1989 Georgi et al.
4,882,575 A 11/1989 Kawahara
4,884,013 A 11/1989 Jackson et al.
4,884,065 A 11/1989 Crouse et al.
4,886,422 A 12/1989 Takeuchi et al.
4,898,576 A 2/1990 Philip
4,898,578 A 2/1990 Rubalcaba, Jr.
4,906,103 A 3/1990 Kao
4,908,017 A 3/1990 Howson et al.
4,908,019 A 3/1990 Urquhart et al.
4,910,475 A 3/1990 Lin
4,919,595 A 4/1990 Likuski et al.
4,919,596 A 4/1990 Slate et al.
4,925,444 A 5/1990 Orkin et al.
4,927,411 A 5/1990 Pastrone et al.
4,930,358 A 6/1990 Motegi et al.
4,936,820 A 6/1990 Dennehey
4,936,828 A 6/1990 Chiang
4,938,079 A 7/1990 Goldberg
4,943,279 A 7/1990 Samiotes et al.
4,946,439 A 8/1990 Eggers
4,947,856 A 8/1990 Beard
4,950,235 A 8/1990 Slate et al.
4,950,244 A 8/1990 Fellingham et al.
4,959,050 A 9/1990 Bobo, Jr.
4,966,579 A 10/1990 Polaschegg
4,968,941 A 11/1990 Rogers
4,972,842 A 11/1990 Korten et al.
4,976,687 A 12/1990 Martin
4,978,335 A 12/1990 Arthur, III
4,979,940 A 12/1990 Lapp et al.
4,981,467 A 1/1991 Bobo et al.
5,000,663 A 3/1991 Gorton
5,000,739 A 3/1991 Kulisz et al.
5,006,050 A 4/1991 Cooke et al.

(56) References Cited

U.S. PATENT DOCUMENTS 5,010,473 A 4/1991 Jacobs
5,014,714 A 5/1991 Millay et al.
5,014,798 A 5/1991 Glynn
5,018,945 A 5/1991 D'Silva
5,026,348 A 6/1991 Venegas
5,028,857 A 7/1991 Taghezout
5,032,112 A 7/1991 Fairchild et al.
5,034,004 A 7/1991 Crankshaw
5,035,143 A 7/1991 Latimer et al.
5,040,699 A 8/1991 Gangemi
5,041,086 A * 8/1991 Koenig ................. A61M 5/172 128/DIG. 13
5,043,706 A 8/1991 Oliver
5,045,069 A 9/1991 Imparato
5,049,047 A 9/1991 Polaschegg et al.
5,052,230 A 10/1991 Lang
5,053,747 A 10/1991 Slate et al.
5,055,761 A 10/1991 Mills
5,056,992 A 10/1991 Simons
5,058,161 A 10/1991 Weiss
5,059,171 A 10/1991 Bridge
5,063,603 A 11/1991 Burt
5,064,412 A 11/1991 Henke et al.
5,078,683 A 1/1992 Sancoff et al.
5,084,663 A 1/1992 Olsson
5,084,828 A 1/1992 Kaufman et al.
5,088,981 A 2/1992 Howson et al.
5,096,385 A 3/1992 Georgi et al.
5,097,505 A 3/1992 Weiss
5,100,380 A 3/1992 Epstein et al.
5,102,392 A 4/1992 Sakai et al.
5,103,211 A 4/1992 Daoud et al.
5,104,374 A 4/1992 Bishko et al.
5,108,367 A 4/1992 Epstein et al.
5,109,850 A 5/1992 Blanco et al.
5,116,203 A 5/1992 Nartwick et al.
5,116,312 A 5/1992 Blakenship et al.
5,116,316 A 5/1992 Sertic
5,123,275 A 6/1992 Daoud et al.
5,124,627 A 6/1992 Okada
5,125,499 A 6/1992 Saathoff et al.
5,131,816 A 7/1992 Brown
5,132,603 A 7/1992 Yoshimoto
5,153,827 A 10/1992 Coutre et al.
5,158,441 A 10/1992 Aid
5,161,222 A 11/1992 Montejo et al.
5,174,472 A 12/1992 Raque et al.
5,176,631 A 1/1993 Koenig
5,176,646 A 1/1993 Kuroda
5,179,340 A 1/1993 Rogers
5,180,287 A 1/1993 Natwick et al.
5,181,910 A 1/1993 Scanlon
5,186,057 A 2/1993 Everhart
5,188,603 A 2/1993 Vaillancourt
5,190,522 A 3/1993 Wocicki et al.
5,191,795 A 3/1993 Fellingham et al.
5,192,340 A 3/1993 Grant et al.
5,194,796 A 3/1993 Domeki et al.
5,198,776 A 3/1993 Carr
5,200,090 A 4/1993 Ford
5,205,819 A 4/1993 Ross et al.
5,206,522 A 4/1993 Danby et al.
5,207,642 A 5/1993 Orkin et al.
5,211,626 A 5/1993 Frank et al.
5,213,573 A 5/1993 Sorich et al.
5,215,450 A 6/1993 Tamari
5,216,597 A 6/1993 Beckers
5,219,099 A 6/1993 Spence et al.
5,219,327 A 6/1993 Okada
5,221,268 A 6/1993 Barton et al.
5,229,713 A 7/1993 Bullock et al.
5,232,476 A 8/1993 Grant
5,233,571 A 8/1993 Wirtschafter
5,237,309 A 8/1993 Frantz et al.
5,242,406 A 9/1993 Gross et al.
5,242,408 A 9/1993 Jhuboo et al.
5,243,982 A 9/1993 Möstl et al.
5,244,463 A 9/1993 Cordner, Jr. et al.
5,244,568 A 9/1993 Lindsay et al.
5,254,096 A 10/1993 Rondelet et al.
5,256,155 A 10/1993 Yerlikaya et al.
5,256,156 A 10/1993 Kern et al.
5,256,157 A 10/1993 Samiotes et al.
5,257,206 A 10/1993 Hanson
5,260,665 A 11/1993 Goldberg
5,262,944 A 11/1993 Weisner et al.
5,267,980 A 12/1993 Dirr et al.
5,274,316 A 12/1993 Evans et al.
5,276,610 A 1/1994 Maeda et al.
5,280,728 A 1/1994 Sato et al.
5,283,510 A 2/1994 Tamaki et al.
5,287,851 A 2/1994 Beran et al.
5,292,306 A 3/1994 Wynkoop et al.
5,295,967 A 3/1994 Rondelet et al.
5,298,021 A 3/1994 Sherer
5,303,585 A 4/1994 Lichte
5,304,126 A 4/1994 Epstein et al.
5,304,216 A 4/1994 Wallace
5,308,333 A 5/1994 Skakoon
5,317,506 A 5/1994 Coutre et al.
5,319,363 A 6/1994 Welch et al.
5,319,979 A 6/1994 Abrahamson
5,321,392 A 6/1994 Skakoon et al.
5,325,170 A 6/1994 Bornhop
5,325,728 A 7/1994 Zimmerman et al.
5,328,460 A 7/1994 Lord et al.
5,330,634 A 7/1994 Wong et al.
5,333,497 A 8/1994 Braend et al.
5,336,051 A 8/1994 Tamari
5,338,157 A 8/1994 Blomquist
5,342,298 A 8/1994 Michaels
5,343,734 A 9/1994 Maeda et al.
5,343,885 A 9/1994 Grant
5,346,466 A 9/1994 Yerlikaya et al.
5,356,378 A 10/1994 Doan et al.
5,359,271 A 10/1994 Husher
D352,778 S 11/1994 Irvin et al.
5,364,346 A 11/1994 Schrezenmeir
5,366,346 A 11/1994 Danby
5,368,562 A 11/1994 Blomquist et al.
5,374,865 A 12/1994 Yoshimura et al.
5,376,070 A 12/1994 Purvis et al.
5,378,231 A 1/1995 Johnson et al.
5,382,232 A 1/1995 Hague et al.
5,383,369 A 1/1995 Khuri-Yakub et al.
5,389,071 A 2/1995 Kawahara et al.
5,389,078 A 2/1995 Zalesky et al.
5,392,638 A 2/1995 Kawahara
5,394,732 A 3/1995 Johnson et al.
5,395,320 A 3/1995 Padda et al.
5,399,171 A 3/1995 Bowman et al.
5,406,954 A 4/1995 Tomita
5,408,326 A 4/1995 Priestley
5,415,528 A 5/1995 Ogden et al.
5,417,119 A 5/1995 Smoll
5,417,222 A 5/1995 Dempsey et al.
5,417,395 A 5/1995 Fowler et al.
5,418,443 A 5/1995 Kikuchi
5,421,208 A 6/1995 Packard et al.
5,423,748 A 6/1995 Uhala
5,423,749 A 6/1995 Merte et al.
5,423,759 A 6/1995 Campbell
5,428,284 A 6/1995 Kaneda et al.
5,429,485 A 7/1995 Dodge
5,429,601 A 7/1995 Conley
5,429,602 A 7/1995 Hauser
5,431,627 A 7/1995 Pastrone et al.
5,434,508 A 7/1995 Ishida
5,437,624 A 8/1995 Langley et al.
5,444,316 A 8/1995 Ohya et al.
5,444,378 A 8/1995 Rogers
5,445,621 A 8/1995 Poli et al.
5,450,758 A 9/1995 Smoll
5,451,881 A 9/1995 Finger

(56) References Cited

U.S. PATENT DOCUMENTS

| | | | | |
|---|---|---|---|---|
| 5,455,423 | A | 10/1995 | Mount et al. | |
| 5,455,851 | A | 10/1995 | Chaco et al. | |
| 5,463,906 | A | 11/1995 | Spani et al. | |
| 5,464,392 | A | 11/1995 | Epstein et al. | |
| 5,465,082 | A | 11/1995 | Chaco | |
| 5,469,851 | A | 11/1995 | Lipschutz | |
| 5,473,948 | A | 12/1995 | Moss et al. | |
| 5,480,294 | A | 1/1996 | Di Perna et al. | |
| 5,482,438 | A | 1/1996 | Anderson et al. | |
| 5,485,408 | A | 1/1996 | Blomquist | |
| 5,486,286 | A | 1/1996 | Peterson et al. | |
| D367,528 | S | 2/1996 | Martson et al. | |
| 5,489,265 | A | 2/1996 | Montalvo et al. | |
| 5,495,566 | A | 2/1996 | Kwatinetz | |
| 5,496,273 | A | 3/1996 | Pastrone et al. | |
| 5,505,696 | A | 4/1996 | Miki | |
| 5,505,828 | A | 4/1996 | Wong et al. | |
| 5,507,288 | A | 4/1996 | Bocker et al. | |
| 5,507,412 | A | 4/1996 | Ebert et al. | |
| 5,520,637 | A | 5/1996 | Pager et al. | |
| 5,522,798 | A | 6/1996 | Johnson et al. | |
| 5,522,799 | A | 6/1996 | Furukawa | |
| 5,527,344 | A | 6/1996 | Arzbaecher et al. | |
| 5,527,630 | A | 6/1996 | Nagata | |
| 5,533,389 | A | 7/1996 | Kamen et al. | |
| 5,537,853 | A | 7/1996 | Finburgh et al. | |
| 5,542,040 | A | 7/1996 | Chang et al. | |
| 5,545,140 | A | 8/1996 | Conero et al. | |
| 5,547,470 | A | 8/1996 | Johnson et al. | |
| 5,551,850 | A | 9/1996 | Williamson et al. | |
| 5,554,013 | A | 9/1996 | Owens et al. | |
| 5,554,115 | A | 9/1996 | Thomas et al. | |
| 5,558,638 | A | 9/1996 | Evers et al. | |
| 5,562,615 | A | 10/1996 | Nassif | |
| 5,563,486 | A | 10/1996 | Yamamoto et al. | |
| 5,572,105 | A | 11/1996 | Nojima et al. | |
| 5,573,502 | A | 11/1996 | LeCocq et al. | |
| 5,583,280 | A | 12/1996 | Mo et al. | |
| 5,584,667 | A | 12/1996 | Davis | |
| 5,584,806 | A | 12/1996 | Amano | |
| 5,586,868 | A | 12/1996 | Lawless et al. | |
| 5,590,653 | A | 1/1997 | Aida et al. | |
| 5,594,786 | A | 1/1997 | Chaco et al. | |
| 5,600,073 | A | 2/1997 | Hill | |
| 5,601,420 | A | 2/1997 | Warner et al. | |
| 5,609,575 | A | 3/1997 | Larson et al. | |
| 5,609,576 | A | 3/1997 | Voss | |
| 5,611,784 | A | 3/1997 | Barresi et al. | |
| 5,616,124 | A | 4/1997 | Hague et al. | |
| 5,620,312 | A | 4/1997 | Hyman et al. | |
| 5,620,608 | A | 4/1997 | Rosa et al. | |
| 5,626,140 | A | 5/1997 | Feldman et al. | |
| 5,626,151 | A | 5/1997 | Linden | |
| 5,626,563 | A | 5/1997 | Dodge et al. | |
| 5,627,443 | A | 5/1997 | Kimura et al. | |
| 5,628,309 | A | 5/1997 | Brown | |
| 5,628,731 | A | 5/1997 | Dodge et al. | |
| 5,630,710 | A | 5/1997 | Tune et al. | |
| 5,634,896 | A | 6/1997 | Bryant et al. | |
| 5,637,095 | A | 6/1997 | Nason et al. | |
| 5,640,075 | A | 6/1997 | Brasseur et al. | |
| 5,640,150 | A | 6/1997 | Atwater | |
| 5,643,212 | A | 7/1997 | Coutre et al. | |
| 5,648,710 | A | 7/1997 | Ikeda | |
| 5,649,536 | A | 7/1997 | Ogura et al. | |
| 5,651,775 | A | 7/1997 | Walker et al. | |
| 5,657,000 | A | 8/1997 | Ellingboe | |
| 5,658,133 | A | 8/1997 | Anderson et al. | |
| 5,658,250 | A | 8/1997 | Blomquist et al. | |
| 5,659,234 | A | 8/1997 | Cresens | |
| 5,661,245 | A | 8/1997 | Svoboda et al. | |
| D384,052 | S | 9/1997 | Kodosky | |
| 5,662,612 | A | 9/1997 | Niehoff | |
| 5,665,065 | A | 9/1997 | Colman et al. | |
| 5,669,877 | A | 9/1997 | Blomquist | |
| 5,672,154 | A | 9/1997 | Sillén et al. | |
| 5,672,832 | A | 9/1997 | Cucci et al. | |
| 5,681,285 | A | 10/1997 | Ford et al. | |
| 5,681,286 | A | 10/1997 | Niehoff | |
| 5,685,844 | A | 11/1997 | Marttila | |
| 5,685,866 | A | 11/1997 | Lopez | |
| 5,687,717 | A | 11/1997 | Halpern et al. | |
| 5,689,229 | A | 11/1997 | Chaco et al. | |
| 5,691,613 | A | 11/1997 | Gutwillinger | |
| 5,695,464 | A | 12/1997 | Viallet | |
| 5,695,473 | A | 12/1997 | Olsen | |
| 5,697,899 | A | 12/1997 | Hillman et al. | |
| 5,697,916 | A | 12/1997 | Schraga | |
| 5,712,795 | A | 1/1998 | Layman et al. | |
| 5,713,856 | A | 2/1998 | Eggers et al. | |
| 5,714,691 | A | 2/1998 | Hill | |
| 5,718,562 | A | 2/1998 | Lawless et al. | |
| 5,718,569 | A | 2/1998 | Holst | |
| 5,720,721 | A | 2/1998 | Dumas et al. | |
| 5,722,417 | A | 3/1998 | Rudolph | |
| 5,728,074 | A | 3/1998 | Castellano et al. | |
| 5,728,948 | A | 3/1998 | Bignell et al. | |
| 5,733,257 | A | 3/1998 | Stemby | |
| 5,733,259 | A | 3/1998 | Valcke et al. | |
| 5,734,464 | A | 3/1998 | Gibbs | |
| 5,738,659 | A | 4/1998 | Neer et al. | |
| 5,743,856 | A | 4/1998 | Oka et al. | |
| 5,744,027 | A | 4/1998 | Connell et al. | |
| 5,744,929 | A | 4/1998 | Miyazaki | |
| 5,745,378 | A | 4/1998 | Barker et al. | |
| 5,752,813 | A | 5/1998 | Tyner et al. | |
| 5,752,918 | A | 5/1998 | Fowler et al. | |
| 5,752,919 | A | 5/1998 | Schrimpf | |
| 5,755,691 | A | 5/1998 | Hilborne | |
| 5,758,643 | A | 6/1998 | Wong et al. | |
| 5,761,072 | A | 6/1998 | Bardsley, Jr. et al. | |
| 5,764,034 | A | 6/1998 | Bowman et al. | |
| 5,766,155 | A | 6/1998 | Hyman et al. | |
| 5,772,635 | A * | 6/1998 | Dastur | G16H 20/17 604/67 |
| 5,778,256 | A | 7/1998 | Darbee | |
| 5,781,442 | A | 7/1998 | Engleson et al. | |
| 5,782,805 | A * | 7/1998 | Meinzer | G16H 20/17 604/67 |
| 5,788,669 | A | 8/1998 | Peterson | |
| 5,788,674 | A | 8/1998 | McWilliams | |
| 5,789,923 | A | 8/1998 | Shimoyama et al. | |
| 5,792,069 | A | 8/1998 | Greenwald et al. | |
| 5,793,211 | A | 8/1998 | Shimoyama et al. | |
| 5,795,327 | A | 8/1998 | Wilson et al. | |
| 5,798,934 | A | 8/1998 | Saigo et al. | |
| 5,800,387 | A | 9/1998 | Duffy et al. | |
| 5,803,712 | A | 9/1998 | Davis et al. | |
| 5,803,917 | A | 9/1998 | Butterfield | |
| 5,805,455 | A | 9/1998 | Lipps | |
| 5,807,322 | A | 9/1998 | Lindsey et al. | |
| 5,810,770 | A | 9/1998 | Chin et al. | |
| 5,813,972 | A | 9/1998 | Nazarian et al. | |
| 5,814,004 | A | 9/1998 | Tamari | |
| 5,814,015 | A | 9/1998 | Gargano et al. | |
| D400,195 | S | 10/1998 | Utesch | |
| 5,816,779 | A | 10/1998 | Lawless et al. | |
| 5,822,715 | A | 10/1998 | Worthington et al. | |
| 5,827,179 | A | 10/1998 | Lichter et al. | |
| 5,827,223 | A | 10/1998 | Butterfield | |
| 5,832,448 | A | 11/1998 | Brown | |
| 5,836,910 | A | 11/1998 | Duffy et al. | |
| 5,841,261 | A | 11/1998 | Nojima et al. | |
| 5,841,284 | A | 11/1998 | Takahashi | |
| 5,843,035 | A | 12/1998 | Bowman | |
| 5,848,971 | A | 12/1998 | Fowler et al. | |
| 5,850,344 | A | 12/1998 | Conkright | |
| 5,857,843 | A | 1/1999 | Leason et al. | |
| 5,864,330 | A | 1/1999 | Haynes | |
| 5,865,805 | A | 2/1999 | Ziemba | |
| 5,867,821 | A | 2/1999 | Ballantyne et al. | |
| 5,871,465 | A | 2/1999 | Vasko | |
| 5,872,453 | A | 2/1999 | Shimoyama et al. | |
| 5,875,195 | A | 2/1999 | Choi | |

(56) References Cited

U.S. PATENT DOCUMENTS 5,882,300 A 3/1999 Malinouskas et al.
5,882,339 A 3/1999 Beiser et al.
5,885,245 A 3/1999 Lynch et al.
5,889,379 A 3/1999 Yanagi et al.
5,891,051 A 4/1999 Han et al.
5,894,209 A 4/1999 Takagi et al.
5,897,493 A 4/1999 Brown
5,897,498 A 4/1999 Canfield, II et al.
5,898,292 A 4/1999 Takemoto et al.
5,899,665 A 5/1999 Makino et al.
5,901,150 A 5/1999 Jhuboo et al.
5,904,666 A 5/1999 DeDecker et al.
5,904,668 A 5/1999 Hyman et al.
5,905,207 A 5/1999 Schalk
5,906,598 A 5/1999 Giesier
5,910,252 A 6/1999 Truitt et al.
5,915,240 A 6/1999 Karpf
5,920,263 A 7/1999 Huttenhoff et al.
5,923,159 A 7/1999 Ezell
5,924,074 A 7/1999 Evans
5,927,349 A 7/1999 Martucci
5,932,119 A 8/1999 Kaplan et al.
5,932,987 A 8/1999 McLoughlin
5,935,066 A 8/1999 Harris
5,935,099 A 8/1999 Peterson et al.
5,935,106 A 8/1999 Olsen
5,938,634 A 8/1999 Packard
5,938,636 A 8/1999 Kramer et al.
5,941,846 A 8/1999 Duffy et al.
5,944,660 A 8/1999 Kimball et al.
5,947,911 A 9/1999 Wong et al.
5,954,527 A 9/1999 Jhuboo et al.
5,954,696 A 9/1999 Ryan et al.
5,956,023 A 9/1999 Lyle et al.
5,956,501 A 9/1999 Brown
5,957,885 A 9/1999 Bollish et al.
5,957,890 A 9/1999 Mann et al.
5,971,594 A 10/1999 Sahai et al.
5,973,497 A 10/1999 Bergk et al.
5,975,081 A 11/1999 Hood et al.
5,989,222 A 11/1999 Cole et al.
5,990,838 A 11/1999 Burns et al.
5,991,525 A 11/1999 Shah et al.
5,993,393 A 11/1999 Ryan et al.
5,994,876 A 11/1999 Canny et al.
5,997,476 A 12/1999 Brown
6,000,828 A 12/1999 Leet
6,003,006 A 12/1999 Colella et al.
6,003,388 A 12/1999 Oeftering
D418,497 S 1/2000 Howard, III et al.
6,012,034 A 1/2000 Hamparian et al.
6,017,318 A 1/2000 Gauthier et al.
6,017,493 A 1/2000 Cambron
6,021,392 A 2/2000 Lester et al.
6,023,977 A 2/2000 Langdon et al.
6,024,539 A 2/2000 Blomquist
6,027,441 A 2/2000 Cantu
6,028,412 A 2/2000 Shine et al.
6,032,676 A 3/2000 Moore
6,033,561 A 3/2000 Schoendorfer
6,036,017 A 3/2000 Bayliss, IV
6,068,612 A 5/2000 Bowman
6,068,615 A 5/2000 Brown et al.
6,073,106 A 6/2000 Rozen et al.
6,077,246 A 6/2000 Kullas et al.
6,083,206 A 7/2000 Molko
6,089,104 A 7/2000 Chang
6,104,295 A 8/2000 Gaisser et al.
6,110,152 A 8/2000 Kovelman
6,110,153 A 8/2000 Davis
RE36,871 E 9/2000 Epstein et al.
6,120,459 A 9/2000 Nitzan et al.
6,122,536 A 9/2000 Sun et al.
6,142,008 A 11/2000 Cole et al.
6,150,942 A 11/2000 O'Brien
6,151,643 A 11/2000 Cheng et al.
6,157,914 A 12/2000 Seto et al.
6,158,288 A 12/2000 Smith
6,158,965 A 12/2000 Butterfield et al.
6,159,147 A 12/2000 Lichter et al.
6,159,186 A 12/2000 Wickham et al.
6,164,921 A 12/2000 Moubayed et al.
6,167,567 A 12/2000 Chiles et al.
6,168,561 B1 1/2001 Cantu
6,178,827 B1 1/2001 Feller
6,182,667 B1 2/2001 Hanks et al.
6,186,141 B1 2/2001 Pike et al.
6,189,105 B1 2/2001 Lopes
6,192,752 B1 2/2001 Blaine
6,195,589 B1 2/2001 Ketcham
6,202,711 B1 3/2001 Martucci
6,203,528 B1 3/2001 Deckert
6,208,107 B1 3/2001 Maske et al.
6,212,936 B1 4/2001 Meisberger
6,213,972 B1 4/2001 Butterfield
6,231,320 B1 5/2001 Lawless et al.
6,234,176 B1 5/2001 Domae et al.
6,236,326 B1 5/2001 Murphy et al.
6,237,398 B1 5/2001 Porat et al.
6,241,704 B1 6/2001 Peterson et al.
6,248,067 B1 6/2001 Causey, III et al.
6,250,132 B1 6/2001 Drzewiecki
6,259,355 B1 7/2001 Chaco et al.
6,259,587 B1 7/2001 Sheldon et al.
6,261,065 B1 7/2001 Nayak
6,262,946 B1 7/2001 Khuri-Yakub et al.
6,267,559 B1 7/2001 Mossman et al.
6,267,725 B1 7/2001 Dubberstein et al.
6,269,340 B1 7/2001 Ford et al.
6,270,455 B1 8/2001 Brown
6,271,813 B1 8/2001 Palalau
6,277,072 B1 8/2001 Bardy
6,277,099 B1 8/2001 Strowe et al.
6,280,380 B1 8/2001 Bardy
6,280,391 B1 8/2001 Olson et al.
6,280,408 B1 8/2001 Sipin
6,283,761 B1 9/2001 Joao
6,285,155 B1 9/2001 Maske et al.
6,312,378 B1 11/2001 Bardy
6,322,516 B1 11/2001 Masuda et al.
6,330,351 B1 12/2001 Yasunaga
6,336,053 B1 1/2002 Beatty
6,337,675 B1 1/2002 Toffolo et al.
6,345,539 B1 2/2002 Rawes et al.
6,347,553 B1 2/2002 Morris et al.
6,349,740 B1 2/2002 Cho et al.
6,358,225 B1 3/2002 Butterfield
6,358,387 B1 3/2002 Kopf-Sill et al.
6,362,591 B1 3/2002 Moberg
6,363,282 B1 3/2002 Nichols et al.
6,385,505 B1 5/2002 Lipps
6,386,050 B1 5/2002 Yin et al.
6,394,958 B1 5/2002 Bratteli et al.
6,396,583 B1 5/2002 Clare
D459,362 S 6/2002 Platz
6,398,760 B1 6/2002 Danby
6,405,076 B1 6/2002 Taylor et al.
6,408,679 B1 6/2002 Kline-Schoder et al.
6,409,699 B1 6/2002 Ash
6,413,238 B1 7/2002 Maget
6,416,291 B1 7/2002 Butterfield et al.
6,418,334 B1 7/2002 Unger et al.
6,418,535 B1 7/2002 Kulakowski et al.
6,445,053 B1 9/2002 Cho
6,456,245 B1 9/2002 Crawford
6,457,346 B1 10/2002 Kline-Schoder et al.
6,463,785 B1 10/2002 Kline-Schoder et al.
6,467,331 B1 10/2002 Kline-Schoder et al.
6,468,242 B1 10/2002 Wilson et al.
6,475,178 B1 11/2002 Krajewski
6,481,980 B1 11/2002 Vandlik
6,482,158 B2 11/2002 Mault
6,482,185 B1 11/2002 Hartmann
6,485,263 B1 11/2002 Bryant et al.

(56) References Cited

U.S. PATENT DOCUMENTS 6,485,418 B2 11/2002 Yasushi et al.
6,485,465 B2 11/2002 Moberg et al.
6,487,916 B1 12/2002 Gomm et al.
6,489,896 B1 12/2002 Platt
6,494,694 B2 12/2002 Lawless et al.
6,494,831 B1 12/2002 Koritzinsky
6,497,680 B1 12/2002 Holst et al.
6,503,221 B1 1/2003 Briggs
6,512,944 B1 1/2003 Kovtun et al.
6,516,667 B1 2/2003 Broad et al.
6,517,482 B1 2/2003 Eiden et al.
6,519,569 B1 2/2003 White et al.
6,529,751 B1 3/2003 Van Driel et al.
6,531,708 B1 3/2003 Malmstrom
6,539,315 B1 3/2003 Adams et al.
D473,238 S 4/2003 Cockerill
6,540,672 B1 4/2003 Simonsen et al.
6,544,212 B2 4/2003 Galley et al.
6,544,228 B1 4/2003 Heitmeier
6,558,125 B1 5/2003 Futterknecht
6,558,351 B1 5/2003 Steil et al.
6,562,012 B1 5/2003 Brown et al.
6,564,825 B2 5/2003 Lowery et al.
6,565,509 B1 5/2003 Say et al.
6,568,416 B2 5/2003 Tucker et al.
6,572,542 B1 6/2003 Houben et al.
6,572,545 B2 6/2003 Knobbe et al.
6,572,576 B2 6/2003 Brugger et al.
6,578,002 B1 6/2003 Derzay et al.
6,578,422 B2 6/2003 Lam et al.
6,578,435 B2 6/2003 Gould et al.
6,581,117 B1 6/2003 Klein et al.
RE38,189 E 7/2003 Walker et al.
6,585,675 B1 7/2003 O'Mahony et al.
6,589,229 B1 7/2003 Connelly et al.
6,589,792 B1 7/2003 Malachowski
6,599,281 B1 7/2003 Struys et al.
6,599,282 B2 7/2003 Burko
6,602,191 B2 8/2003 Quy
6,605,072 B2 8/2003 Struys et al.
6,606,047 B1 8/2003 Börjesson et al.
6,609,047 B1 8/2003 Lipps
6,615,674 B2 9/2003 Ohnishi
6,616,633 B1 9/2003 Butterfield et al.
6,617,564 B2 9/2003 Ockerse et al.
6,618,916 B1 9/2003 Eberle et al.
6,622,542 B2 9/2003 Derek
6,622,561 B2 9/2003 Lam et al.
D481,121 S 10/2003 Evans
6,629,449 B1 10/2003 Kline-Schoder et al.
6,634,233 B2 10/2003 He
6,640,246 B1 10/2003 Gardy, Jr. et al.
6,641,533 B2 11/2003 Causey, III et al.
6,641,541 B1 11/2003 Lovett et al.
6,648,861 B2 11/2003 Platt et al.
6,652,455 B1 11/2003 Kocher
6,653,937 B2 11/2003 Nelson et al.
6,659,980 B2 12/2003 Moberg et al.
D485,356 S 1/2004 Evans
6,685,668 B1 2/2004 Cho et al.
6,685,678 B2 2/2004 Evans et al.
6,689,069 B2 2/2004 Bratteli et al.
6,689,091 B2 2/2004 Bui et al.
6,692,241 B2 2/2004 Watanabe et al.
D487,574 S 3/2004 Glaser
6,716,004 B2 4/2004 Vandlik
6,719,535 B2 4/2004 Rakestraw et al.
6,721,582 B2 4/2004 Trepagnier et al.
6,722,211 B1 4/2004 Ciobanu et al.
6,725,200 B1 4/2004 Rost
6,725,721 B2 4/2004 Venczel
6,731,989 B2 5/2004 Engleson et al.
6,732,595 B2 5/2004 Lynnworth
6,738,052 B1 5/2004 Manke et al.
6,740,072 B2 5/2004 Starkweather et al.
6,741,212 B2 5/2004 Kralovec et al.
6,748,808 B2 6/2004 Lam et al.
6,749,403 B2 6/2004 Bryant et al.
6,752,787 B1 6/2004 Causey, III et al.
6,753,842 B1 6/2004 Williams et al.
6,759,007 B1 7/2004 Westberg
6,760,643 B2 7/2004 Lipps
6,768,920 B2 7/2004 Lange
6,773,412 B2 8/2004 O'Mahony
6,780,156 B2 8/2004 Haueter et al.
6,783,328 B2 8/2004 Lucke et al.
6,785,573 B2 8/2004 Kovtun et al.
6,786,885 B2 9/2004 Hochman et al.
6,789,426 B2 9/2004 Yaralioglu et al.
6,790,198 B1 9/2004 White et al.
6,793,625 B2 9/2004 Cavallaro et al.
6,801,227 B2 10/2004 Bocionek et al.
6,805,671 B2 10/2004 Stergiopoulos et al.
6,807,965 B1 10/2004 Hickle
6,809,653 B1 10/2004 Mann et al.
6,813,964 B1 11/2004 Clark et al.
6,814,547 B2 11/2004 Childers
6,824,528 B1 11/2004 Faries
6,830,558 B2 12/2004 Flaherty et al.
6,840,113 B2 1/2005 Fukumura et al.
6,846,161 B2 1/2005 Kline
6,852,094 B2 2/2005 Beck
6,852,104 B2 2/2005 Blomquist
6,854,338 B2 2/2005 Khuri-Yakub et al.
6,857,318 B1 2/2005 Silber et al.
6,869,425 B2 3/2005 Briggs et al.
6,873,268 B2 3/2005 Lebel et al.
6,883,376 B2 4/2005 He
6,885,881 B2 4/2005 Leonhardt
6,887,216 B2 5/2005 Hochman et al.
6,898,301 B2 5/2005 Iwanaga
6,907,361 B2 6/2005 Molenaar
6,907,792 B2 6/2005 Ohnishi
6,915,170 B2 7/2005 Engleson et al.
6,920,795 B2 7/2005 Bischoff et al.
6,923,763 B1 8/2005 Kovatchev et al.
6,928,338 B1 8/2005 Buchser et al.
6,929,619 B2 8/2005 Fago et al.
6,929,751 B2 8/2005 Bowman
6,932,114 B2 8/2005 Sparks
6,932,796 B2 8/2005 Sage et al.
6,935,192 B2 8/2005 Sobek et al.
6,936,029 B2 8/2005 Mann et al.
6,941,005 B2 9/2005 Lary et al.
6,942,636 B2 9/2005 Holst et al.
6,945,954 B2 9/2005 Hochman et al.
6,958,705 B2 10/2005 Lebel et al.
6,964,204 B2 11/2005 Clark et al.
6,973,374 B2 12/2005 Ader
6,974,437 B2 12/2005 Lebel et al.
6,975,922 B2 12/2005 Duncan et al.
6,978,779 B2 12/2005 Haveri et al.
6,979,326 B2 12/2005 Mann et al.
6,981,960 B2 1/2006 Cho et al.
6,984,218 B2 1/2006 Nayak et al.
6,985,768 B2 1/2006 Hemming et al.
6,985,870 B2 1/2006 Martucci et al.
6,986,347 B2 1/2006 Hickle
6,986,753 B2 1/2006 Bui
6,997,905 B2 2/2006 Gillespie, Jr. et al.
6,997,920 B2 2/2006 Mann et al.
7,006,005 B2 2/2006 Nazarian et al.
7,017,623 B2 3/2006 Tribble et al.
7,021,148 B2 4/2006 Kuhn
7,025,743 B2 4/2006 Mann et al.
7,029,455 B2 4/2006 Flaherty
7,029,456 B2 4/2006 Ware et al.
7,031,857 B2 4/2006 Tarassenko et al.
7,059,184 B2 6/2006 Kanouda et al.
7,060,059 B2 6/2006 Keith et al.
7,069,793 B2 7/2006 Ishikawa et al.
7,072,725 B2 7/2006 Bristol et al.
7,074,209 B2 7/2006 Evans et al.
7,080,557 B2 7/2006 Adnan

(56) References Cited

U.S. PATENT DOCUMENTS 7,082,843 B2 8/2006 Clark et al.
7,087,444 B2 8/2006 Wong et al.
7,092,796 B2 8/2006 Vanderveen
7,092,797 B2 8/2006 Gaines et al.
7,093,502 B2 8/2006 Kupnik et al.
7,096,729 B2 8/2006 Repko et al.
7,103,419 B2 9/2006 Engleson et al.
7,104,763 B2 9/2006 Bouton et al.
7,104,769 B2 9/2006 Davis
7,108,680 B2 9/2006 Rohr et al.
7,109,878 B2 9/2006 Mann et al.
7,115,113 B2 10/2006 Evans et al.
7,117,041 B2 10/2006 Engleson et al.
7,137,964 B2 11/2006 Flaherty
7,141,037 B2 11/2006 Butterfield et al.
7,152,490 B1 12/2006 Freund, Jr. et al.
7,154,397 B2 12/2006 Zerhusen et al.
7,161,488 B2 1/2007 Frasch
7,162,290 B1 1/2007 Levin
7,162,927 B1 1/2007 Selvan et al.
7,171,277 B2 1/2007 Engleson et al.
7,171,992 B2 2/2007 DiGianfilippo et al.
7,174,789 B2 2/2007 Orr et al.
7,185,288 B2 2/2007 McKeever
7,197,943 B2 4/2007 Lee et al.
7,201,734 B2 4/2007 Hickle
7,204,823 B2 4/2007 Estes et al.
7,206,715 B2 4/2007 Vanderveen et al.
7,213,009 B2 5/2007 Pestotnik
7,220,240 B2 5/2007 Struys et al.
7,229,430 B2 6/2007 Hickle et al.
7,230,529 B2 6/2007 Ketcherside
7,232,430 B2 6/2007 Carlisle
7,238,164 B2 7/2007 Childers et al.
7,247,154 B2 7/2007 Hickle
7,253,779 B2 8/2007 Greer et al.
7,254,425 B2 8/2007 Lowery et al.
7,258,534 B2 8/2007 Fathallah et al.
7,267,664 B2 9/2007 Rizzo
7,267,665 B2 9/2007 Steil et al.
7,272,529 B2 9/2007 Hogan et al.
7,278,983 B2 10/2007 Ireland et al.
7,291,123 B2 11/2007 Baraldi et al.
7,293,461 B1 11/2007 Gimdt
7,294,109 B2 11/2007 Lovett et al.
7,296,482 B2 11/2007 Schaffer et al.
7,300,418 B2 11/2007 Zaleski
7,305,883 B2 12/2007 Khuri-Yakub et al.
7,327,273 B2 2/2008 Hung et al.
D563,986 S 3/2008 Lettau
7,338,470 B2 3/2008 Katz
7,343,224 B2 3/2008 DiGianfilippo et al.
7,347,836 B2 3/2008 Peterson et al.
7,347,854 B2 3/2008 Shelton et al.
7,354,420 B2 4/2008 Steil et al.
7,356,382 B2 4/2008 Vanderveen
7,360,999 B2 4/2008 Nelson et al.
7,364,562 B2 4/2008 Braig et al.
7,367,942 B2 5/2008 Grage et al.
7,369,948 B1 5/2008 Ferenczi et al.
7,384,410 B2 6/2008 Eggers et al.
7,397,166 B1 7/2008 Morgan et al.
7,398,183 B2 7/2008 Holland et al.
7,399,277 B2 7/2008 Saidara et al.
7,402,153 B2 7/2008 Steil et al.
7,402,154 B2 7/2008 Mendez
7,407,489 B2 8/2008 Mendez
7,414,534 B1 8/2008 Kroll et al.
7,415,895 B2 8/2008 Kurisaki et al.
7,426,443 B2 9/2008 Simon
7,430,675 B2 9/2008 Lee et al.
D581,426 S 11/2008 Jasinski
7,447,566 B2 11/2008 Knauper et al.
7,447,643 B1 11/2008 Olson
7,452,190 B2 11/2008 Bouton et al.
7,454,314 B2 11/2008 Holland et al.
7,471,994 B2 12/2008 Ford et al.
7,477,997 B2 1/2009 Kaplit
7,482,818 B2 1/2009 Greenwald et al.
7,483,756 B2 1/2009 Engleson et al.
7,490,021 B2 2/2009 Holland et al.
7,491,187 B2 2/2009 Van Den Berghe et al.
7,503,903 B2 3/2009 Carlisle et al.
7,517,332 B2 4/2009 Tonelli et al.
7,523,401 B1 4/2009 Aldridge
D593,125 S 5/2009 Danton
7,545,075 B2 6/2009 Huang et al.
D596,195 S 7/2009 Wall
7,556,616 B2 7/2009 Fathallah et al.
7,561,986 B2 7/2009 Vanderveen et al.
7,571,024 B2 8/2009 Duncan et al.
7,605,730 B2 10/2009 Tomioka et al.
D604,306 S 11/2009 Chow
7,614,310 B2 11/2009 Konzelmann
7,645,258 B2 1/2010 White et al.
7,654,127 B2 2/2010 Krulevitch et al.
7,657,443 B2 2/2010 Crass
7,668,731 B2 2/2010 Martucci et al.
7,678,048 B1 3/2010 Urbano et al.
7,693,697 B2 4/2010 Westenskow et al.
7,699,806 B2 4/2010 Ware et al.
7,705,727 B2 4/2010 Pestotnik
D617,807 S 6/2010 Christie
7,726,179 B2 6/2010 Muller
D621,845 S 8/2010 Anzures
7,766,873 B2 8/2010 Moberg et al.
7,775,126 B2 8/2010 Eckhardt
7,775,127 B2 8/2010 Wade
7,785,284 B2 8/2010 Baralsi et al.
7,785,313 B2 8/2010 Mastrototaro
7,786,909 B2 8/2010 Udupa et al.
7,806,886 B2 10/2010 Kanderian, Jr. et al.
7,826,981 B2 11/2010 Goode, Jr. et al.
7,847,276 B2 12/2010 Carlisle
7,860,583 B2 12/2010 Condurso et al.
7,871,394 B2 1/2011 Halbert et al.
7,876,443 B2 1/2011 Bernacki
7,895,053 B2 2/2011 Holland et al.
7,895,882 B2 3/2011 Carlisle
7,896,834 B2 3/2011 Smisson, III
7,896,842 B2 3/2011 Palmroos et al.
7,905,710 B2 3/2011 Wang et al.
7,933,780 B2 4/2011 de la Huerga
7,938,817 B2 5/2011 Gelfand et al.
7,945,452 B2 5/2011 Fathallah et al.
D642,195 S 7/2011 Marks
7,976,508 B2 7/2011 Hoag
7,981,073 B2 7/2011 Mollstam
7,981,082 B2 7/2011 Wang et al.
7,998,134 B2 8/2011 Fangrow
8,002,736 B2 8/2011 Patrick et al.
8,034,020 B2 10/2011 Dewey
8,038,593 B2 10/2011 Friedman et al.
8,062,249 B2 11/2011 Willinska
8,065,161 B2 11/2011 Howard et al.
8,067,760 B2 11/2011 Carlisle
8,075,514 B2 12/2011 Butterfield et al.
8,075,546 B2 12/2011 Carlisle et al.
8,078,983 B2 12/2011 Davis et al.
8,121,857 B2 2/2012 Galasso et al.
8,149,131 B2 4/2012 Blomquist
D659,709 S 5/2012 Eby
8,175,668 B1 5/2012 Nabutovsky et al.
8,177,739 B2 5/2012 Cartledge et al.
8,180,440 B2 5/2012 McCombie et al.
8,185,322 B2 5/2012 Schroeder et al.
8,197,444 B1 6/2012 Bazargan et al.
8,219,413 B2 7/2012 Martinez et al.
8,221,395 B2 7/2012 Shelton et al.
8,226,597 B2 7/2012 Jacobson et al.
8,231,578 B2 7/2012 Fathallah et al.
8,234,128 B2 7/2012 Martucci et al.
D667,452 S 9/2012 Wujcik
D667,840 S 9/2012 Anzures

(56) References Cited

U.S. PATENT DOCUMENTS

| | | | |
|---|---|---|---|
| 8,271,106 | B2 | 9/2012 | Wehba et al. |
| 8,287,514 | B2 | 10/2012 | Miller et al. |
| 8,291,337 | B2 | 10/2012 | Gannin et al. |
| 8,313,308 | B2 | 11/2012 | Lawless et al. |
| 8,317,698 | B2 | 11/2012 | Lowery |
| 8,317,750 | B2 | 11/2012 | Ware et al. |
| 8,317,752 | B2 | 11/2012 | Cozmi et al. |
| 8,318,094 | B1 | 11/2012 | Bayandorian et al. |
| 8,340,792 | B2 | 12/2012 | Condurso et al. |
| 8,347,731 | B2 | 1/2013 | Genosar |
| 8,359,338 | B2 | 1/2013 | Butterfield et al. |
| 8,361,021 | B2 | 1/2013 | Wang et al. |
| 8,378,837 | B2 | 2/2013 | Wang et al. |
| 8,387,112 | B1 | 2/2013 | Ranjan et al. |
| 8,388,598 | B2 | 3/2013 | Steinkogler |
| 8,398,616 | B2 | 3/2013 | Budiman |
| 8,403,908 | B2 | 3/2013 | Jacobson et al. |
| D679,727 | S | 4/2013 | Abratowski |
| 8,409,164 | B2 | 4/2013 | Fangrow |
| 8,449,524 | B2 | 5/2013 | Braig et al. |
| 8,469,942 | B2 | 6/2013 | Kow et al. |
| 8,477,307 | B1 | 7/2013 | Yufa et al. |
| 8,494,879 | B2 | 7/2013 | Davis et al. |
| 8,504,179 | B2 | 8/2013 | Blomquist |
| 8,506,552 | B2 | 8/2013 | Rebours |
| 8,517,990 | B2 | 8/2013 | Teel et al. |
| 8,518,021 | B2 | 8/2013 | Stewart et al. |
| 8,522,832 | B2 | 9/2013 | Lopez et al. |
| 8,523,797 | B2 | 9/2013 | Lowery et al. |
| 8,539,812 | B2 | 9/2013 | Stringham et al. |
| 8,543,416 | B2 | 9/2013 | Palmroos et al. |
| 8,577,692 | B2 | 11/2013 | Silkaitis et al. |
| D696,270 | S | 12/2013 | Hyunjung et al. |
| D696,275 | S | 12/2013 | Tagliabue et al. |
| 8,606,596 | B1 | 12/2013 | Bochenko et al. |
| 8,622,990 | B2 | 1/2014 | Estes et al. |
| 8,630,722 | B2 | 1/2014 | Condurso et al. |
| 8,641,670 | B2 | 2/2014 | Yodfat et al. |
| D701,517 | S | 3/2014 | Thornton et al. |
| 8,665,214 | B2 | 3/2014 | Forutanpour et al. |
| 8,666,769 | B2 | 3/2014 | Butler et al. |
| 8,700,421 | B2 | 4/2014 | Feng et al. |
| 8,706,233 | B2 | 4/2014 | Su et al. |
| D705,260 | S | 5/2014 | Gerssen |
| 8,719,045 | B2 | 5/2014 | Yoon |
| 8,721,584 | B2 | 5/2014 | Braithwaite et al. |
| 8,728,020 | B2 | 5/2014 | Caleffi et al. |
| D706,294 | S | 6/2014 | Jewitt |
| 8,758,306 | B2 | 6/2014 | Lopez et al. |
| 8,761,906 | B2 | 6/2014 | Condurso et al. |
| D709,091 | S | 7/2014 | Kwon |
| 8,768,719 | B2 | 7/2014 | Wehba et al. |
| 8,771,251 | B2 | 7/2014 | Ruchti et al. |
| 8,792,981 | B2 | 7/2014 | Yudovsky et al. |
| D710,370 | S | 8/2014 | Inose et al. |
| D711,916 | S | 8/2014 | Matas |
| D712,926 | S | 9/2014 | Meegan |
| D713,417 | S | 9/2014 | Daniel |
| D713,418 | S | 9/2014 | Yang |
| D713,420 | S | 9/2014 | Dallmeyer |
| 8,821,432 | B2 | 9/2014 | Unverdorben |
| 8,823,382 | B2 | 9/2014 | Rondoni et al. |
| 8,823,528 | B2 | 9/2014 | Blomquist |
| 8,857,269 | B2 | 10/2014 | Johnson et al. |
| 8,858,185 | B2 | 10/2014 | Johnson et al. |
| 8,905,965 | B2 | 12/2014 | Mandro et al. |
| D721,385 | S | 1/2015 | Barling |
| 8,948,734 | B2 | 2/2015 | Vaglio |
| 8,964,185 | B1 | 2/2015 | Luo et al. |
| 9,005,150 | B2 | 4/2015 | Ware et al. |
| 9,026,370 | B2 | 5/2015 | Rubalcaba et al. |
| D731,535 | S | 6/2015 | Seo et al. |
| 9,084,855 | B2 | 7/2015 | Ware et al. |
| 9,114,217 | B2 | 8/2015 | Sur et al. |
| 9,134,735 | B2 | 9/2015 | Lowery et al. |
| 9,134,736 | B2 | 9/2015 | Lowery et al. |
| 9,138,526 | B2 | 9/2015 | Ware et al. |
| D742,413 | S | 11/2015 | Torres |
| D742,414 | S | 11/2015 | Brunner |
| D742,415 | S | 11/2015 | Cahill |
| D743,414 | S | 11/2015 | Uno |
| D744,001 | S | 11/2015 | Orr |
| 9,190,010 | B2 | 11/2015 | Vik et al. |
| D747,339 | S | 1/2016 | Cohen |
| 9,240,002 | B2 | 1/2016 | Hume et al. |
| D750,099 | S | 2/2016 | Kadosh |
| 9,272,089 | B2 | 3/2016 | Jacobson et al. |
| D754,740 | S | 4/2016 | Cho et al. |
| 9,316,216 | B1 | 4/2016 | Cook et al. |
| D757,099 | S | 5/2016 | Seo |
| 9,333,291 | B2 | 5/2016 | Jacobson et al. |
| D758,379 | S | 6/2016 | Kadosh |
| D759,036 | S | 6/2016 | Evanes |
| D760,238 | S | 6/2016 | Suarez |
| D760,248 | S | 6/2016 | Smith |
| D760,295 | S | 6/2016 | Smith |
| D760,788 | S | 7/2016 | Cho |
| D761,820 | S | 7/2016 | Lee |
| D762,238 | S | 7/2016 | Day |
| 9,381,296 | B2 | 7/2016 | Arrizza et al. |
| 9,393,362 | B2 | 7/2016 | Cozmi et al. |
| D764,538 | S | 8/2016 | Lee |
| 9,468,718 | B2 | 10/2016 | Hung et al. |
| 9,498,583 | B2 | 11/2016 | Sur et al. |
| D773,519 | S | 12/2016 | Hurley |
| D777,205 | S | 1/2017 | Orr |
| 9,545,475 | B2 | 1/2017 | Borges et al. |
| 9,545,476 | B2 | 1/2017 | Qi et al. |
| D779,537 | S | 2/2017 | Wingate-Whyte |
| D779,546 | S | 2/2017 | Chetzroni |
| D781,874 | S | 3/2017 | Dunn |
| D782,535 | S | 3/2017 | Menz |
| 9,594,875 | B2 | 3/2017 | Arrizza et al. |
| D785,018 | S | 4/2017 | Lee et al. |
| D785,040 | S | 4/2017 | Day et al. |
| 9,662,436 | B2 | 5/2017 | Belkin et al. |
| 9,707,341 | B2 | 7/2017 | Dumas, III et al. |
| 9,764,087 | B2 | 9/2017 | Peterfreund et al. |
| 9,773,330 | B1 | 9/2017 | Douglas |
| D803,872 | S | 11/2017 | Cole |
| D803,881 | S | 11/2017 | Hurley |
| 9,808,316 | B2 | 11/2017 | Hasegawa |
| D806,109 | S | 12/2017 | Day |
| 9,852,265 | B1 | 12/2017 | Treacy et al. |
| D809,006 | S | 1/2018 | Mehta |
| 9,883,987 | B2 | 2/2018 | Lopez et al. |
| 9,943,269 | B2 | 4/2018 | Muhsin et al. |
| D819,051 | S | 5/2018 | Norris et al. |
| D819,052 | S | 5/2018 | Norris et al. |
| D819,058 | S | 5/2018 | Clediere |
| 9,971,871 | B2 | 5/2018 | Arrizza et al. |
| 9,995,611 | B2 | 6/2018 | Ruchti et al. |
| 10,002,496 | B2 | 6/2018 | Humphrey |
| 10,022,498 | B2 | 7/2018 | Ruchti et al. |
| 10,046,112 | B2 | 8/2018 | Oruklu et al. |
| D827,665 | S | 9/2018 | Segars |
| D829,736 | S | 10/2018 | Jochetz et al. |
| 10,089,055 | B1 | 10/2018 | Fryman |
| 10,099,009 | B1 | 10/2018 | Anderson et al. |
| D835,145 | S | 12/2018 | Cashner et al. |
| 10,166,328 | B2 | 1/2019 | Oruklu et al. |
| 10,241,626 | B2 | 3/2019 | Miyazawa |
| 10,297,350 | B2 | 5/2019 | Duke et al. |
| 10,342,917 | B2 | 7/2019 | Shubinsky et al. |
| D862,495 | S | 10/2019 | Vierra |
| 10,430,761 | B2 | 10/2019 | Hume et al. |
| D865,777 | S | 11/2019 | Kovács |
| 10,463,788 | B2 | 11/2019 | Day |
| 10,549,248 | B2 | 2/2020 | Brown et al. |
| 10,578,474 | B2 | 3/2020 | Ruchti et al. |
| 10,596,316 | B2 | 3/2020 | Dumas, III et al. |
| 10,635,784 | B2 | 4/2020 | Rubalcaba, Jr. et al. |
| 10,656,894 | B2 | 5/2020 | Fryman |
| 10,682,102 | B2 | 6/2020 | Declerck |

(56) References Cited

U.S. PATENT DOCUMENTS

| | | | |
|---|---|---|---|
| 10,709,885 | B2 | 7/2020 | Janders et al. |
| D898,055 | S | 10/2020 | Connolly |
| 10,850,024 | B2 | 12/2020 | Day et al. |
| 10,874,793 | B2 | 12/2020 | Oruklu et al. |
| D907,647 | S | 1/2021 | Siebel et al. |
| 10,994,077 | B2 | 5/2021 | Rosinko |
| 11,004,035 | B2 | 5/2021 | Hume et al. |
| 11,007,119 | B2 | 5/2021 | Lopez et al. |
| D922,430 | S | 6/2021 | Kataoka et al. |
| D922,432 | S | 6/2021 | Kataoka et al. |
| D923,050 | S | 6/2021 | Kataoka et al. |
| 11,029,911 | B2 | 6/2021 | Fryman |
| D926,201 | S | 7/2021 | Bryant et al. |
| D926,224 | S | 7/2021 | Hummel |
| D928,813 | S | 8/2021 | Nurutdinov et al. |
| D928,840 | S | 8/2021 | Amit et al. |
| 11,090,431 | B2 | 8/2021 | Dumas, III et al. |
| D931,884 | S | 9/2021 | Bryant et al. |
| D931,892 | S | 9/2021 | Nurutdinov |
| D934,282 | S | 10/2021 | Clymer |
| 11,135,360 | B1 | 10/2021 | Jacobson et al. |
| 11,219,715 | B2 | 1/2022 | Gray et al. |
| D943,613 | S | 2/2022 | Bryant et al. |
| 11,246,985 | B2 | 2/2022 | Gylland et al. |
| D944,839 | S | 3/2022 | Harvey |
| D946,608 | S | 3/2022 | Higuchi |
| 11,278,671 | B2 | 3/2022 | Cavendish, Jr. et al. |
| 11,298,456 | B2 | 4/2022 | Shubinsky et al. |
| 11,324,888 | B2 | 5/2022 | Shubinsky et al. |
| 11,344,668 | B2 | 5/2022 | Sileika et al. |
| 11,344,673 | B2 | 5/2022 | Lindo et al. |
| 11,376,361 | B2 | 7/2022 | Ruchti et al. |
| 11,378,430 | B2 | 7/2022 | Ruchti et al. |
| 11,395,875 | B2 | 7/2022 | Rubalcaba, Jr. et al. |
| D962,984 | S | 9/2022 | Kuo et al. |
| 11,433,177 | B2 | 9/2022 | Oruklu et al. |
| 11,439,570 | B2 | 9/2022 | Lopez et al. |
| D980,273 | S | 3/2023 | Sigmon et al. |
| 11,596,737 | B2 | 3/2023 | Dumas, III et al. |
| 11,599,854 | B2 | 3/2023 | Hume et al. |
| 11,623,042 | B2 | 4/2023 | Day |
| 11,626,205 | B2 | 4/2023 | Arrizza et al. |
| D986,271 | S | 5/2023 | Shor |
| D998,633 | S | 9/2023 | PJ |
| 11,868,161 | B2 | 1/2024 | Fryman |
| 11,883,361 | B2 | 1/2024 | Janssen |
| D1,017,633 | S | 3/2024 | Chung |
| D1,018,593 | S | 3/2024 | Chiah |
| 11,933,650 | B2 | 3/2024 | Ruchti et al. |
| D1,021,917 | S | 4/2024 | Ceniceroz |
| D1,023,027 | S | 4/2024 | Slettnes |
| D1,024,096 | S | 4/2024 | Zhong |
| 11,972,395 | B2 | 4/2024 | Hume et al. |
| D1,027,974 | S | 5/2024 | Correy |
| 11,996,188 | B2 | 5/2024 | Arrizza et al. |
| D1,032,623 | S | 6/2024 | Lim et al. |
| D1,033,461 | S | 7/2024 | Kasha |
| D1,035,698 | S | 7/2024 | Brown et al. |
| 12,048,831 | B2 | 7/2024 | Oruklu et al. |
| D1,039,563 | S | 8/2024 | Daley |
| D1,039,564 | S | 8/2024 | Leetz et al. |
| 12,059,551 | B2 | 8/2024 | Dumas, III et al. |
| 12,064,217 | B2 | 8/2024 | Ahmed et al. |
| 12,073,928 | B2 | 8/2024 | Freeman et al. |
| D1,042,473 | S | 9/2024 | Siebel et al. |
| 12,076,531 | B2 | 9/2024 | Shubinsky et al. |
| 12,083,310 | B2 | 9/2024 | Shubinsky et al. |
| 12,115,337 | B2 | 10/2024 | Day et al. |
| D1,054,430 | S | 12/2024 | Ellison et al. |
| D1,055,954 | S | 12/2024 | Fujisawa |
| 12,156,967 | B2 | 12/2024 | King et al. |
| D1,056,922 | S | 1/2025 | Pryor |
| D1,058,585 | S | 1/2025 | Chae |
| D1,059,400 | S | 1/2025 | Chai et al. |
| 12,201,811 | B2 | 1/2025 | Gylland et al. |
| D1,060,377 | S | 2/2025 | Lemay et al. |
| 12,239,818 | B2 | 3/2025 | Morton |
| D1,068,786 | S | 4/2025 | Holaman et al. |
| 12,268,843 | B2 | 4/2025 | Cavendish, Jr. et al. |
| 12,280,239 | B2 | 4/2025 | Day |
| 12,310,921 | B2 | 5/2025 | Janssen |
| 12,333,201 | B2 | 6/2025 | Fryman |
| 12,346,879 | B2 | 7/2025 | Hume et al. |
| 12,350,233 | B2 | 7/2025 | Fister |
| 12,380,997 | B2 | 8/2025 | Arrizza et al. |
| 12,390,586 | B2 | 8/2025 | Jacobson et al. |
| D1,091,564 | S | 9/2025 | Cousineau et al. |
| 12,485,221 | B2 | 12/2025 | Lindo et al. |
| 12,539,365 | B2 | 2/2026 | Ruchti et al. |
| 12,571,665 | B2 | 3/2026 | Ruchti et al. |
| 12,599,716 | B2 | 4/2026 | Cousineau et al. |
| 2001/0007636 | A1 | 7/2001 | Butterfield |
| 2001/0014769 | A1 | 8/2001 | Bufe et al. |
| 2001/0015099 | A1 | 8/2001 | Blaine |
| 2001/0016056 | A1 | 8/2001 | Westphal et al. |
| 2001/0032099 | A1 | 10/2001 | Joao |
| 2001/0037060 | A1 | 11/2001 | Thompson et al. |
| 2001/0041869 | A1 | 11/2001 | Causey et al. |
| 2001/0044731 | A1 | 11/2001 | Coffman et al. |
| 2002/0003892 | A1 | 1/2002 | Iwanaga |
| 2002/0007116 | A1 | 1/2002 | Zatezalo et al. |
| 2002/0013545 | A1 | 1/2002 | Soltanpour et al. |
| 2002/0013551 | A1 | 1/2002 | Zaitsu et al. |
| 2002/0015018 | A1 | 2/2002 | Shimazu et al. |
| 2002/0018720 | A1 | 2/2002 | Carlisle et al. |
| 2002/0029776 | A1 | 3/2002 | Blomquist |
| 2002/0031838 | A1 | 3/2002 | Meinhart et al. |
| 2002/0032583 | A1 | 3/2002 | Joao |
| 2002/0040208 | A1 | 4/2002 | Flaherty et al. |
| 2002/0044059 | A1 | 4/2002 | Reeder et al. |
| 2002/0045806 | A1 | 4/2002 | Baker, Jr. et al. |
| 2002/0082728 | A1 | 6/2002 | Mueller et al. |
| 2002/0083771 | A1 | 7/2002 | Khuri-Yakub et al. |
| 2002/0085952 | A1 | 7/2002 | Ellingboe et al. |
| 2002/0087115 | A1 | 7/2002 | Hartlaub |
| 2002/0093641 | A1 | 7/2002 | Ortyn et al. |
| 2002/0095486 | A1 | 7/2002 | Bahl |
| 2002/0099282 | A1 | 7/2002 | Knobbe et al. |
| 2002/0099334 | A1 | 7/2002 | Hanson et al. |
| 2002/0143580 | A1 | 10/2002 | Bristol et al. |
| 2002/0147389 | A1 | 10/2002 | Cavallaro et al. |
| 2002/0152239 | A1 | 10/2002 | Bautista-Lloyd et al. |
| 2002/0158919 | A1 | 10/2002 | Nacey |
| 2002/0168278 | A1 | 11/2002 | Jeon et al. |
| 2002/0173703 | A1 | 11/2002 | Lebel et al. |
| 2002/0183693 | A1 | 12/2002 | Peterson et al. |
| 2003/0009244 | A1 | 1/2003 | Engleson |
| 2003/0013959 | A1 | 1/2003 | Grunwald et al. |
| 2003/0018289 | A1 | 1/2003 | Ng et al. |
| 2003/0018308 | A1 | 1/2003 | Tsai |
| 2003/0025602 | A1 | 2/2003 | Medema et al. |
| 2003/0028082 | A1 | 2/2003 | Thompson |
| 2003/0030001 | A1 | 2/2003 | Cooper et al. |
| 2003/0045840 | A1 | 3/2003 | Burko |
| 2003/0050621 | A1 | 3/2003 | Lebel et al. |
| 2003/0060688 | A1 | 3/2003 | Ciarniello et al. |
| 2003/0060765 | A1 | 3/2003 | Campbell et al. |
| 2003/0065537 | A1 | 4/2003 | Evans |
| 2003/0065589 | A1 | 4/2003 | Giacchetti |
| 2003/0073954 | A1 | 4/2003 | Moberg et al. |
| 2003/0079746 | A1 | 5/2003 | Hickle |
| 2003/0083583 | A1 | 5/2003 | Kovtun et al. |
| 2003/0091442 | A1 | 5/2003 | Bush et al. |
| 2003/0104982 | A1 | 6/2003 | Wittmann et al. |
| 2003/0106553 | A1 | 6/2003 | Vanderveen |
| 2003/0117296 | A1 | 6/2003 | Seely |
| 2003/0125662 | A1 | 7/2003 | Bui |
| 2003/0130616 | A1 | 7/2003 | Steil |
| 2003/0135087 | A1 | 7/2003 | Hickle et al. |
| 2003/0136193 | A1 | 7/2003 | Fujimoto |
| 2003/0139701 | A1 | 7/2003 | White et al. |
| 2003/0140928 | A1 | 7/2003 | Bui et al. |
| 2003/0140929 | A1 | 7/2003 | Wilkes et al. |
| 2003/0141981 | A1 | 7/2003 | Bui et al. |

(56) References Cited

U.S. PATENT DOCUMENTS

2003/0143746 A1 7/2003 Sage, Jr.
2003/0144878 A1 7/2003 Wilkes et al.
2003/0158508 A1 8/2003 DiGianfilippo
2003/0159741 A1 8/2003 Sparks
2003/0160683 A1 8/2003 Blomquist
2003/0163789 A1 8/2003 Blomquist
2003/0167185 A1 9/2003 Gordon et al.
2003/0173408 A1 9/2003 Mosher, Jr. et al.
2003/0186833 A1 10/2003 Huff et al.
2003/0187338 A1 10/2003 Say et al.
2003/0200116 A1 10/2003 Forrester
2003/0204274 A1 10/2003 Ullestad et al.
2003/0204416 A1 10/2003 Acharya
2003/0212364 A1 11/2003 Mann et al.
2003/0212379 A1 11/2003 Bylund et al.
2003/0216682 A1 11/2003 Junker
2003/0217962 A1 11/2003 Childers et al.
2003/0233071 A1 12/2003 Gillespie, Jr. et al.
2004/0010786 A1 1/2004 Cool et al.
2004/0030277 A1 2/2004 O'Mahony et al.
2004/0031756 A1 2/2004 Suzuki et al.
2004/0047736 A1 3/2004 Nose et al.
2004/0051368 A1 3/2004 Caputo
2004/0057226 A1 3/2004 Berthou et al.
2004/0064342 A1 4/2004 Browne et al.
2004/0073125 A1 4/2004 Lovett et al.
2004/0073161 A1 4/2004 Tachibana
2004/0077996 A1 4/2004 Jasperson et al.
2004/0082908 A1 4/2004 Whitehurst
2004/0082918 A1 4/2004 Evans et al.
2004/0087888 A1* 5/2004 DiGianfilippo ........ G16H 20/17 604/19
2004/0104271 A1 6/2004 Martucci et al.
2004/0119753 A1 6/2004 Zencke
2004/0120825 A1 6/2004 Bouton et al.
2004/0128162 A1 7/2004 Schlotterbeck et al.
2004/0128163 A1 7/2004 Goodman et al.
2004/0130573 A1 7/2004 Konuma
2004/0133166 A1 7/2004 Moberg et al.
2004/0139004 A1 7/2004 Cohen et al.
2004/0145114 A1 7/2004 Ippolito et al.
2004/0147034 A1 7/2004 Gore et al.
2004/0149823 A1 8/2004 Aptekar
2004/0152970 A1 8/2004 Hunter et al.
2004/0158193 A1 8/2004 Bui et al.
2004/0167464 A1 8/2004 Ireland et al.
2004/0167465 A1 8/2004 Kohler
2004/0167804 A1 8/2004 Simpson
2004/0172222 A1 9/2004 Simpson et al.
2004/0172283 A1 9/2004 Vanderveen
2004/0172289 A1* 9/2004 Kozic .................... G16H 70/40 705/2
2004/0172301 A1 9/2004 Mihai et al.
2004/0172302 A1 9/2004 Martucci et al.
2004/0176984 A1 9/2004 White et al.
2004/0181314 A1 9/2004 Zaleski
2004/0193025 A1 9/2004 Steil et al.
2004/0193325 A1 9/2004 Bonderud
2004/0193328 A1 9/2004 Butterfield et al.
2004/0204638 A1 10/2004 Diab et al.
2004/0204673 A1 10/2004 Flaherty et al.
2004/0215278 A1 10/2004 Stegink et al.
2004/0220517 A1 11/2004 Starkweather et al.
2004/0225252 A1 11/2004 Gillespie et al.
2004/0225409 A1 11/2004 Duncan et al.
2004/0232219 A1 11/2004 Fowler
2004/0253123 A1 12/2004 Xie et al.
2004/0254434 A1 12/2004 Goodnow et al.
2004/0254513 A1 12/2004 Shang et al.
2005/0021006 A1 1/2005 Tonnies
2005/0021297 A1 1/2005 Hartlaub
2005/0022274 A1 1/2005 Campbell et al.
2005/0038680 A1 2/2005 McMahon
2005/0055242 A1 3/2005 Bello et al.
2005/0055244 A1 3/2005 Mullan et al.
2005/0065465 A1 3/2005 Lebel et al.
2005/0075544 A1 4/2005 Shapiro et al.
2005/0080801 A1 4/2005 Kothandaraman et al.
2005/0096593 A1 5/2005 Pope et al.
2005/0099624 A1 5/2005 Staehr
2005/0102669 A1 5/2005 Marney et al.
2005/0107923 A1 5/2005 Vanderveen
2005/0108057 A1 5/2005 Cohen et al.
2005/0119597 A1 6/2005 O'Mahony et al.
2005/0119914 A1 6/2005 Batch
2005/0131739 A1 6/2005 Rabinowitz et al.
2005/0137522 A1 6/2005 Aoki
2005/0143864 A1 6/2005 Blomquist
2005/0145010 A1 7/2005 Vanderveen et al.
2005/0171503 A1 8/2005 Van Den Berghe et al.
2005/0171815 A1 8/2005 Vanderveen
2005/0177045 A1 8/2005 Degertekin et al.
2005/0177096 A1 8/2005 Bollish et al.
2005/0182306 A1 8/2005 Sloan
2005/0182355 A1 8/2005 Bui
2005/0182366 A1 8/2005 Vogt et al.
2005/0187515 A1 8/2005 Varrichio et al.
2005/0192529 A1 9/2005 Butterfield et al.
2005/0192557 A1 9/2005 Brauker et al.
2005/0197554 A1 9/2005 Polcha
2005/0197621 A1 9/2005 Poulsen et al.
2005/0209563 A1 9/2005 Hopping et al.
2005/0209793 A1 9/2005 Yamada
2005/0224083 A1 10/2005 Crass
2005/0235732 A1 10/2005 Rush
2005/0238506 A1 10/2005 Mescher et al.
2005/0240305 A1 10/2005 Bogash et al.
2005/0273059 A1 12/2005 Mernoe et al.
2005/0277890 A1 12/2005 Stewart et al.
2005/0278194 A1 12/2005 Holland et al.
2005/0279419 A1 12/2005 Tribble et al.
2006/0002799 A1 1/2006 Schann et al.
2006/0009727 A1 1/2006 O'Mahony et al.
2006/0009734 A1 1/2006 Martin
2006/0042633 A1 3/2006 Bishop et al.
2006/0047270 A1 3/2006 Shelton
2006/0053036 A1 3/2006 Coffman et al.
2006/0064020 A1 3/2006 Burnes et al.
2006/0064053 A1 3/2006 Bollish et al.
2006/0079768 A1 4/2006 Small et al.
2006/0079831 A1 4/2006 Gilbert
2006/0100746 A1 5/2006 Leibner-Druska
2006/0100907 A1 5/2006 Holland et al.
2006/0106649 A1 5/2006 Eggers et al.
2006/0116639 A1 6/2006 Russell
2006/0117856 A1 6/2006 Orr et al.
2006/0117867 A1 6/2006 Froehlich et al.
2006/0122867 A1 6/2006 Eggers et al.
2006/0135939 A1 6/2006 Brown
2006/0135940 A1 6/2006 Joshi
2006/0136095 A1 6/2006 Rob et al.
2006/0136271 A1 6/2006 Eggers et al.
2006/0140798 A1 6/2006 Kutsuzawa
2006/0143051 A1 6/2006 Eggers et al.
2006/0173260 A1 8/2006 Gaoni et al.
2006/0173406 A1 8/2006 Hayes et al.
2006/0181695 A1 8/2006 Sage, Jr.
2006/0187069 A1 8/2006 Duan
2006/0190302 A1 8/2006 Eggers et al.
2006/0195022 A1 8/2006 Trepagnier et al.
2006/0200007 A1 9/2006 Brockway et al.
2006/0200369 A1 9/2006 Batch et al.
2006/0211404 A1 9/2006 Cromp et al.
2006/0224140 A1 10/2006 Junker
2006/0224141 A1 10/2006 Rush et al.
2006/0224181 A1 10/2006 McEwen et al.
2006/0226088 A1 10/2006 Robinson et al.
2006/0226089 A1 10/2006 Robinson et al.
2006/0226090 A1 10/2006 Robinson et al.
2006/0229557 A1* 10/2006 Fathallah ............... G16H 40/63 705/2
2006/0229918 A1 10/2006 Fotsch et al.
2006/0235353 A1 10/2006 Gelfand et al.
2006/0255149 A1 11/2006 Retter et al.

(56) References Cited

U.S. PATENT DOCUMENTS

2006/0258985 A1 11/2006 Russell
2006/0260416 A1 11/2006 Sage et al.
2006/0264895 A1 11/2006 Flanders
2006/0266128 A1 11/2006 Clark et al.
2006/0270971 A1 11/2006 Gelfand et al.
2006/0271286 A1 11/2006 Rosenberg
2006/0272421 A1 12/2006 Frinak et al.
2006/0275142 A1 12/2006 Bouton et al.
2006/0276771 A1 12/2006 Galley
2007/0015972 A1 1/2007 Wang et al.
2007/0027506 A1 2/2007 Stender et al.
2007/0036511 A1 2/2007 Lundquist et al.
2007/0055479 A1* 3/2007 Holland ................ G16H 20/17 702/182
2007/0060796 A1 3/2007 Kim
2007/0060869 A1 3/2007 Tolle et al.
2007/0060871 A1 3/2007 Istoc
2007/0060872 A1 3/2007 Hall et al.
2007/0060874 A1 3/2007 Nesbitt et al.
2007/0062250 A1 3/2007 Krulevitch et al.
2007/0065363 A1 3/2007 Dalal et al.
2007/0078314 A1 4/2007 Grounsell
2007/0083152 A1 4/2007 Williams, Jr. et al.
2007/0084286 A1 4/2007 Ajay et al.
2007/0084288 A1 4/2007 Thomas et al.
2007/0088271 A1 4/2007 Richards
2007/0088333 A1 4/2007 Levin et al.
2007/0093753 A1 4/2007 Krulevitcvh et al.
2007/0094045 A1 4/2007 Cobbs et al.
2007/0094046 A1 4/2007 Cobbs et al.
2007/0100222 A1 5/2007 Mastrototaro et al.
2007/0100665 A1 5/2007 Brown
2007/0112298 A1 5/2007 Mueller et al.
2007/0118405 A1 5/2007 Campbell et al.
2007/0129618 A1 6/2007 Goldberger et al.
2007/0136098 A1 6/2007 Smythe et al.
2007/0142822 A1 6/2007 Remde
2007/0156452 A1 7/2007 Batch
2007/0156456 A1 7/2007 McGillin et al.
2007/0179436 A1 8/2007 Braig et al.
2007/0180916 A1 8/2007 Tian et al.
2007/0191770 A1 8/2007 Moberg et al.
2007/0191817 A1 8/2007 Martin
2007/0197963 A1 8/2007 Griffiths et al.
2007/0214003 A1 9/2007 Holland et al.
2007/0215545 A1 9/2007 Bissler et al.
2007/0233035 A1 10/2007 Wehba et al.
2007/0233049 A1 10/2007 Wehba et al.
2007/0233521 A1* 10/2007 Wehba .................. G16H 20/17 700/216
2007/0240497 A1 10/2007 Robinson et al.
2007/0250339 A1 10/2007 Mallett et al.
2007/0255250 A1 11/2007 Moberg et al.
2007/0257788 A1 11/2007 Carlson
2007/0267945 A1 11/2007 Sudol
2007/0270747 A1 11/2007 Remde
2007/0274843 A1 11/2007 Vanderveen et al.
2007/0289384 A1 12/2007 Sakai et al.
2008/0009684 A1 1/2008 Corsetti et al.
2008/0028868 A1 2/2008 Konzelmann et al.
2008/0033361 A1 2/2008 Evans et al.
2008/0039777 A1 2/2008 Katz et al.
2008/0048211 A1 2/2008 Khuri-Yakub et al.
2008/0052704 A1 2/2008 Wysocki
2008/0058773 A1 3/2008 John
2008/0060448 A1 3/2008 Wiest et al.
2008/0065420 A1 3/2008 Tirinato et al.
2008/0071210 A1 3/2008 Moubayed et al.
2008/0071496 A1 3/2008 Glascock
2008/0071580 A1 3/2008 Marcus et al.
2008/0077116 A1 3/2008 Dailey et al.
2008/0086087 A1 4/2008 Spohn et al.
2008/0091466 A1 4/2008 Butler et al.
2008/0097288 A1 4/2008 Levin et al.
2008/0097289 A1 4/2008 Steil et al.
2008/0097317 A1 4/2008 Alholm et al.
2008/0098798 A1 5/2008 Riley et al.
2008/0119822 A1 5/2008 Knauper
2008/0125701 A1 5/2008 Moberg et al.
2008/0139907 A1 6/2008 Rao et al.
2008/0145249 A1 6/2008 Smisson
2008/0169044 A1 7/2008 Osborne et al.
2008/0172030 A1 7/2008 Blomquist et al.
2008/0177126 A1 7/2008 Tate et al.
2008/0184784 A1 8/2008 Dam
2008/0188789 A1 8/2008 Galavotti et al.
2008/0188796 A1 8/2008 Steil et al.
2008/0208484 A1 8/2008 Butterfield et al.
2008/0214919 A1 9/2008 Harmon et al.
2008/0219405 A1 9/2008 Falco et al.
2008/0221521 A1 9/2008 Getz et al.
2008/0221522 A1 9/2008 Moberg et al.
2008/0262469 A1 10/2008 Bristol et al.
2008/0269663 A1 10/2008 Arnold et al.
2008/0269714 A1 10/2008 Mastrototaro et al.
2008/0269723 A1 10/2008 Mastrototaro et al.
2008/0275384 A1 11/2008 Mastrototaro et al.
2008/0300572 A1 12/2008 Rankers et al.
2009/0001908 A1 1/2009 Shubinsky et al.
2009/0005703 A1 1/2009 Fasciano
2009/0006061 A1 1/2009 Thukral et al.
2009/0006129 A1 1/2009 Thukral
2009/0006133 A1 1/2009 Weinert
2009/0015824 A1 1/2009 Shubinsky et al.
2009/0043171 A1 2/2009 Rule
2009/0054743 A1 2/2009 Stewart
2009/0054754 A1 2/2009 McMahon et al.
2009/0062727 A1 3/2009 Woo
2009/0069743 A1 3/2009 Krishnamoorthy et al.
2009/0077248 A1 3/2009 Castellucci et al.
2009/0082676 A1 3/2009 Bennison
2009/0088731 A1 4/2009 Campbell et al.
2009/0097029 A1 4/2009 Tokhtuev et al.
2009/0099866 A1 4/2009 Newman
2009/0099867 A1 4/2009 Newman
2009/0105636 A1 4/2009 Hayter et al.
2009/0112155 A1 4/2009 Zhao
2009/0114037 A1 5/2009 Smith
2009/0119330 A1 5/2009 Sampath et al.
2009/0124963 A1 5/2009 Hogard et al.
2009/0124964 A1 5/2009 Leach et al.
2009/0126825 A1 5/2009 Eliuk et al.
2009/0131861 A1 5/2009 Braig et al.
2009/0135196 A1 5/2009 Holland et al.
2009/0143726 A1 6/2009 Bouton et al.
2009/0144025 A1 6/2009 Bouton et al.
2009/0144026 A1 6/2009 Bouton et al.
2009/0149743 A1 6/2009 Barron et al.
2009/0156922 A1 6/2009 Goldberger et al.
2009/0156975 A1 6/2009 Robinson et al.
2009/0158274 A1 6/2009 Roberts
2009/0177146 A1 7/2009 Nesbitt et al.
2009/0177188 A1 7/2009 Steinkogler
2009/0177248 A1 7/2009 Roberts
2009/0177769 A1 7/2009 Roberts
2009/0178485 A1 7/2009 Thomas et al.
2009/0183147 A1 7/2009 Davis et al.
2009/0192367 A1 7/2009 Braig et al.
2009/0198347 A1 8/2009 Kirzinger
2009/0199113 A1 8/2009 McWhinnie et al.
2009/0205426 A1 8/2009 Balschat et al.
2009/0209938 A1 8/2009 Aalto-Setala
2009/0209945 A1 8/2009 Lobl et al.
2009/0212966 A1 8/2009 Panduro
2009/0221890 A1 9/2009 Saffer et al.
2009/0223294 A1 9/2009 Thomas et al.
2009/0227939 A1 9/2009 Memoe et al.
2009/0264720 A1 10/2009 Torjman et al.
2009/0270810 A1 10/2009 DeBelser
2009/0270833 A1 10/2009 DeBelser
2009/0281497 A1 11/2009 Kamen et al.
2009/0299156 A1 12/2009 Simpson et al.
2009/0315485 A1 12/2009 Verfuerth et al.
2010/0022988 A1 1/2010 Wochner

(56) References Cited

U.S. PATENT DOCUMENTS

2010/0036310 A1 2/2010 Hillman
2010/0056992 A1 3/2010 Hayter
2010/0057042 A1 3/2010 Hayter
2010/0069892 A1 3/2010 Steinbach et al.
2010/0077866 A1 4/2010 Graboi et al.
2010/0079760 A1 4/2010 Bernacki
2010/0094251 A1 4/2010 Estes et al.
2010/0106082 A1 4/2010 Zhou
2010/0114027 A1 5/2010 Jacobson et al.
2010/0121170 A1 5/2010 Rule
2010/0121415 A1 5/2010 Skelton et al.
2010/0130933 A1 5/2010 Holland et al.
2010/0131434 A1 5/2010 Magent et al.
2010/0141460 A1 6/2010 Tokhtuev et al.
2010/0147081 A1 6/2010 Thomas et al.
2010/0152554 A1 6/2010 Steine et al.
2010/0160854 A1 6/2010 Gauthier
2010/0168535 A1 7/2010 Robinson et al.
2010/0177375 A1 7/2010 Seyfried
2010/0185142 A1 7/2010 Kamen et al.
2010/0185182 A1 7/2010 Alme et al.
2010/0198034 A1 8/2010 Thomas et al.
2010/0198182 A1 8/2010 Lanigan et al.
2010/0198183 A1 8/2010 Lanigan et al.
2010/0211002 A1 8/2010 Davis
2010/0212407 A1 8/2010 Stringham et al.
2010/0212675 A1 8/2010 Walling et al.
2010/0217154 A1 8/2010 Deshmukh et al.
2010/0217621 A1 8/2010 Schoenberg
2010/0271218 A1 10/2010 Hoag et al.
2010/0271479 A1 10/2010 Heydlauf
2010/0273738 A1 10/2010 Valcke et al.
2010/0280430 A1 11/2010 Caleffi et al.
2010/0292634 A1 11/2010 Kircher
2010/0295686 A1 11/2010 Sloan et al.
2010/0298765 A1 11/2010 Budiman et al.
2010/0312039 A1 12/2010 Quirico et al.
2010/0317093 A1 12/2010 Turewicz et al.
2010/0317952 A1 12/2010 Budiman et al.
2010/0318025 A1 12/2010 John
2011/0000560 A1 1/2011 Miller et al.
2011/0001605 A1 1/2011 Kiani et al.
2011/0004186 A1 1/2011 Butterfield
2011/0009797 A1 1/2011 Kelly et al.
2011/0028885 A1 2/2011 Eggers et al.
2011/0046558 A1 2/2011 Gravesen et al.
2011/0054311 A1 3/2011 Williams et al.
2011/0062703 A1 3/2011 Lopez et al.
2011/0064612 A1 3/2011 Franzoni et al.
2011/0071464 A1 3/2011 Palerm
2011/0071844 A1 3/2011 Cannon et al.
2011/0072379 A1 3/2011 Gannon
2011/0072381 A1 3/2011 Gannon
2011/0077480 A1 3/2011 Bloom et al.
2011/0078608 A1 3/2011 Gannon et al.
2011/0099313 A1 4/2011 Bolanowski
2011/0105983 A1 5/2011 Kelly et al.
2011/0106561 A1 5/2011 Eaton, Jr. et al.
2011/0107251 A1 5/2011 Guaitoli et al.
2011/0119612 A1 5/2011 Gannon et al.
2011/0133946 A1 6/2011 Kopp
2011/0137241 A1 6/2011 DelCastillo et al.
2011/0138185 A1 6/2011 Ju et al.
2011/0144595 A1 6/2011 Cheng
2011/0152770 A1 6/2011 Diperna et al.
2011/0160649 A1 6/2011 Pan
2011/0162647 A1 7/2011 Huby et al.
2011/0172918 A1 7/2011 Tome
2011/0175728 A1 7/2011 Baker, Jr.
2011/0184379 A1 7/2011 Van Antwerp et al.
2011/0190598 A1 8/2011 Shusterman
2011/0190694 A1 8/2011 Lanier et al.
2011/0238032 A1 9/2011 McTaggart et al.
2011/0241878 A1 10/2011 Hoag
2011/0264006 A1 10/2011 Ali et al.
2011/0264043 A1 10/2011 Kotnick et al.
2011/0282321 A1 11/2011 Steil et al.
2011/0289497 A1 11/2011 Kiaie et al.
2011/0313390 A1 12/2011 Roy et al.
2011/0319728 A1 12/2011 Petisce et al.
2011/0320049 A1 12/2011 Chossat et al.
2012/0016215 A1 1/2012 Condurso et al.
2012/0023431 A1 1/2012 Roth
2012/0025995 A1 2/2012 Moberg et al.
2012/0059234 A1 3/2012 Barrett et al.
2012/0068001 A1 3/2012 Pushkarsky et al.
2012/0083760 A1 4/2012 Ledford et al.
2012/0085277 A1 4/2012 Abdel-Rahman
2012/0089411 A1 4/2012 Srnka et al.
2012/0095433 A1 4/2012 Hungerford et al.
2012/0116195 A1 5/2012 Chaum et al.
2012/0123322 A1 5/2012 Scarpaci et al.
2012/0143116 A1 6/2012 Ware et al.
2012/0180790 A1 7/2012 Montgomery
2012/0185267 A1 7/2012 Kamen et al.
2012/0191059 A1 7/2012 Cummings et al.
2012/0194341 A1 8/2012 Peichel et al.
2012/0203177 A1 8/2012 Lanier
2012/0222774 A1 9/2012 Husnu et al.
2012/0226350 A1 9/2012 Rudser et al.
2012/0245525 A1 9/2012 Pope et al.
2012/0259278 A1 10/2012 Hayes et al.
2012/0310204 A1 12/2012 Krogh et al.
2012/0323212 A1 12/2012 Murphy
2013/0006666 A1 1/2013 Schneider
2013/0009551 A1 1/2013 Knapp
2013/0012880 A1 1/2013 Blomquist
2013/0012917 A1 1/2013 Miller et al.
2013/0032634 A1 2/2013 McKirdy
2013/0036412 A1 2/2013 Birtwhistle et al.
2013/0041342 A1 2/2013 Bernini et al.
2013/0044111 A1 2/2013 VanGilder et al.
2013/0085778 A1 4/2013 Guertin et al.
2013/0110538 A1 5/2013 Butterfield et al.
2013/0116649 A1 5/2013 Breton et al.
2013/0150766 A1 6/2013 Olde et al.
2013/0150821 A1* 6/2013 Bollish ............ A61M 5/16895 422/44
2013/0173291 A1 7/2013 Kelly
2013/0177455 A1 7/2013 Kamen et al.
2013/0184676 A1 7/2013 Kamen et al.
2013/0197930 A1 8/2013 Garibaldi et al.
2013/0201482 A1 8/2013 Munro
2013/0214040 A1 8/2013 Beerling et al.
2013/0218080 A1 8/2013 Peterfreund et al.
2013/0253430 A1 9/2013 Kouyoumjian et al.
2013/0253946 A1 9/2013 Broselow
2013/0274576 A1 10/2013 Amirouche et al.
2013/0281965 A1 10/2013 Kamen et al.
2013/0291116 A1 10/2013 Homer
2013/0296823 A1 11/2013 Melker et al.
2013/0296984 A1 11/2013 Burnett et al.
2013/0318158 A1 11/2013 Teng et al.
2013/0322201 A1 12/2013 Hitchcock et al.
2013/0345658 A1 12/2013 Browne et al.
2013/0345666 A1 12/2013 Panduro et al.
2014/0067425 A1 3/2014 Dudar et al.
2014/0132524 A1 5/2014 Lee
2014/0145915 A1 5/2014 Ribble et al.
2014/0180711 A1 6/2014 Kamen et al.
2014/0224829 A1 8/2014 Capone et al.
2014/0249500 A1 9/2014 Estes et al.
2014/0267563 A1 9/2014 Baca et al.
2014/0303754 A1 10/2014 Nixon et al.
2015/0025453 A1 1/2015 Ledford et al.
2015/0033073 A1 1/2015 Yang et al.
2015/0051458 A1 2/2015 Chen
2015/0057108 A1 2/2015 Regimbal
2015/0065988 A1 3/2015 Holderle et al.
2015/0089439 A1 3/2015 Wada
2015/0114515 A1 4/2015 Phallen
2015/0141921 A1 5/2015 Stewart et al.
2015/0168958 A1 6/2015 Downie et al.
2015/0265765 A1 9/2015 Yavorsky et al.

(56) References Cited

U.S. PATENT DOCUMENTS

| | | | |
|---|---|---|---|
| 2015/0278474 | A1 | 10/2015 | Stueckemann |
| 2015/0289823 | A1 | 10/2015 | Rack-Gomer et al. |
| 2015/0324544 | A1 | 11/2015 | Maslowski et al. |
| 2015/0338340 | A1 | 11/2015 | Jiang et al. |
| 2015/0363086 | A1 | 12/2015 | Lim |
| 2015/0371004 | A1 | 12/2015 | Jones |
| 2016/0000998 | A1 | 1/2016 | Estes |
| 2016/0019352 | A1 | 1/2016 | Seo |
| 2016/0042264 | A1 | 2/2016 | Borges et al. |
| 2016/0051750 | A1 | 2/2016 | Tsoukalis |
| 2016/0110088 | A1 | 4/2016 | Vik et al. |
| 2016/0144101 | A1 | 5/2016 | Pananen |
| 2016/0151560 | A1 | 6/2016 | Toro et al. |
| 2016/0151562 | A1 | 6/2016 | Magers et al. |
| 2016/0151601 | A1 | 6/2016 | Cardelius et al. |
| 2016/0158437 | A1 | 6/2016 | Biasi et al. |
| 2016/0193604 | A1 | 7/2016 | McFarland et al. |
| 2016/0253460 | A1 | 9/2016 | Kanada |
| 2016/0300425 | A1 | 10/2016 | Devaraj et al. |
| 2016/0339167 | A1 | 11/2016 | Ledford et al. |
| 2017/0010677 | A1 | 1/2017 | Roh |
| 2017/0043089 | A1 | 2/2017 | Handler |
| 2017/0056604 | A1 | 3/2017 | Cowan |
| 2017/0068498 | A1 | 3/2017 | Hashem |
| 2017/0132867 | A1 | 5/2017 | Berg et al. |
| 2017/0354941 | A1 | 12/2017 | Brown et al. |
| 2018/0008787 | A1 | 1/2018 | Schriver et al. |
| 2018/0018440 | A1 | 1/2018 | Sugawara |
| 2018/0021514 | A1 | 1/2018 | Rosinko et al. |
| 2018/0206798 | A1 | 7/2018 | Murai |
| 2018/0214636 | A1 | 8/2018 | Amirouche |
| 2018/0296751 | A1 | 10/2018 | Lefort et al. |
| 2018/0300994 | A1 | 10/2018 | Nelson et al. |
| 2018/0326146 | A1 | 11/2018 | Gupta et al. |
| 2019/0072405 | A1 | 3/2019 | Luchner |
| 2019/0111209 | A1 | 4/2019 | Murphy et al. |
| 2019/0160254 | A1 | 5/2019 | Anand |
| 2019/0201607 | A1 | 7/2019 | Öberg |
| 2019/0282757 | A1 | 9/2019 | Gylland et al. |
| 2019/0328964 | A1 | 10/2019 | Desch et al. |
| 2019/0351131 | A1 | 11/2019 | Butterfield et al. |
| 2020/0054825 | A1 | 2/2020 | Kamen et al. |
| 2020/0113784 | A1 | 4/2020 | Lopez et al. |
| 2020/0147303 | A1 | 5/2020 | Lee |
| 2020/0273013 | A1 | 8/2020 | Garner |
| 2020/0330689 | A1 | 10/2020 | Nemoto et al. |
| 2020/0353163 | A1 | 11/2020 | Hand |
| 2020/0384191 | A1 | 12/2020 | Rosinko et al. |
| 2021/0016006 | A1 | 1/2021 | El-Khatib et al. |
| 2021/0041994 | A1 | 2/2021 | Yamamoto |
| 2021/0049555 | A1 | 2/2021 | Shor |
| 2021/0146035 | A1 | 5/2021 | Tsoukalis |
| 2021/0158481 | A1 | 5/2021 | Wang |
| 2021/0158946 | A1 | 5/2021 | Starobinets et al. |
| 2021/0162115 | A1 | 6/2021 | Surine |
| 2021/0304864 | A1 | 9/2021 | Kamen et al. |
| 2022/0088305 | A1 | 3/2022 | Cavendish, Jr. |
| 2022/0184302 | A1 | 6/2022 | Cavendish, Jr. et al. |
| 2022/0184304 | A1 | 6/2022 | Rinehart |
| 2022/0362463 | A1 | 11/2022 | Lindo et al. |
| 2022/0391940 | A1 | 12/2022 | Tietzen et al. |
| 2022/0401640 | A1 | 12/2022 | Jacobson |
| 2023/0010290 | A1 | 1/2023 | Oruklu et al. |
| 2023/0010638 | A1 | 1/2023 | Rubalcaba, Jr. et al. |
| 2023/0017117 | A1 | 1/2023 | Sileika et al. |
| 2023/0112979 | A1 | 4/2023 | Xavier |
| 2023/0245741 | A1 | 8/2023 | Shigyo |
| 2023/0285669 | A1 | 9/2023 | Day |
| 2023/0310735 | A1 | 10/2023 | Cousineau |
| 2024/0366858 | A1 | 11/2024 | Cousineau et al. |
| 2024/0386433 | A1 | 11/2024 | Shah et al. |
| 2025/0114521 | A1 | 4/2025 | Jacobson et al. |
| 2025/0127986 | A1 | 4/2025 | Gylland et al. |
| 2025/0285747 | A1 | 9/2025 | Burgess |
| 2025/0303053 | A1 | 10/2025 | Day |
| 2026/0018280 | A1 | 1/2026 | Arrizza et al. |
| 2026/0096953 | A1 | 4/2026 | Fister |

FOREIGN PATENT DOCUMENTS

| | | |
|---|---|---|
| CA | 2 113 473 | 3/1993 |
| CA | 2 551 817 | 7/2005 |
| CA | 2 554 407 | 8/2005 |
| CA | 2 630 102 | 10/2008 |
| CN | 201061636 | 5/2008 |
| CN | 105682703 | 6/2016 |
| CN | 107106042 | 8/2017 |
| CN | 109310962 | 2/2019 |
| CN | 110573195 | 12/2019 |
| CN | 105848694 | 1/2020 |
| CN | 111954966 | 11/2020 |
| CN | 306893275 | 10/2021 |
| CN | 307412164 | 6/2022 |
| CN | 307979072 | 4/2023 |
| CN | 112105405 | 8/2023 |
| CN | 308499458 | 3/2024 |
| CO | 0020220004676-0001 | 11/2022 |
| CO | 0020220008155-0001 | 11/2022 |
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 100 53 116 | 5/2001 |
| DE | 102 49 238 | 5/2004 |
| DE | 103 52 456 | 7/2005 |
| DE | 20 2022 100987 | 3/2022 |
| EM | 008932172-0003 | 4/2022 |
| EM | 008932172-0004 | 4/2022 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 1 490 131 | 12/2007 |
| EP | 2 026 223 | 2/2009 |
| EP | 2 062 527 | 5/2009 |
| EP | 2 228 004 | 9/2010 |
| EP | 2 243 506 | 10/2010 |
| EP | 2 381 260 | 10/2011 |
| EP | 3 171 287 | 5/2017 |
| ES | 254513 | 10/1981 |
| ES | 2 371 995 | 1/2012 |
| FR | 2 717 919 | 9/1995 |
| GB | 2 121 971 | 1/1984 |

(56) References Cited

FOREIGN PATENT DOCUMENTS

| | | |
|---|---|---|
| GB | 2 303 706 | 2/1997 |
| GB | 2 312 022 | 10/1997 |
| GB | 2 312 046 | 10/1997 |
| GB | 6 201 192 | 4/2022 |
| GB | 6 201 193 | 4/2022 |
| JP | 01-301118 | 12/1989 |
| JP | 01-308568 | 12/1989 |
| JP | 04-161139 | 6/1992 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-518471 | 7/2007 |
| JP | 2007-520270 | 7/2007 |
| JP | 2007-275106 | 10/2007 |
| JP | 2008-249400 | 10/2008 |
| JP | 4322661 | 6/2009 |
| JP | 2009-148592 | 7/2009 |
| JP | 2010-063767 | 3/2010 |
| JP | 5716879 | 3/2015 |
| JP | 6446030 | 12/2018 |
| JP | 2020-533111 | 11/2020 |
| TW | 201841165 | 11/2018 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/010029 | 3/1999 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/061745 | 7/2004 |
| WO | WO 2004/070556 | 8/2004 |
| WO | WO 2004/070994 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2006/026270 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/036854 | 3/2013 |
| WO | WO 2013/096769 | 6/2013 |
| WO | WO 2015/134478 | 9/2015 |
| WO | WO 2016/160321 | 10/2016 |
| WO | WO 2017/051271 | 3/2017 |
| WO | WO 2017/087157 | 5/2017 |
| WO | WO 2017/144366 | 8/2017 |
| WO | WO 2019/055516 | 3/2019 |
| WO | WO 2019/063462 | 4/2019 |
| WO | WO 2019/092680 | 5/2019 |
| WO | WO 2020/214717 | 10/2020 |
| WO | WO 2022/020184 | 1/2022 |
| WO | WO 2022/072159 | 4/2022 |
| WO | WO 2022/125471 | 6/2022 |
| WO | WO 2022/140204 | 6/2022 |
| WO | WO 2023/064662 | 4/2023 |
| WO | WO 2023/108030 | 6/2023 |

(56) References Cited

FOREIGN PATENT DOCUMENTS

| | | |
|---|---|---|
| WO | WO 2023/192791 | 10/2023 |
| WO | WO 2023/244922 | 12/2023 |

OTHER PUBLICATIONS

"Download", Free On-Line Dictionary of Computing, as archived Jun. 16, 2010 in 1 page, http://web.archive.org/web/20100616010314/https://foldoc.org/download.

Fan et al., "Smart Medication Delivery Systems: Infusion Pumps", Supplementary Report, Healthcare Human Factors, Feb. 26, 2010, pp. 94.

"File Verification", Wikipedia.org, as last modified Oct. 11, 2011 in 2 pages, <https://en.wikipedia.org/w/index.php?title=File_verification&oldid=455048290>.

Me.math, Tikz: Arrow tip overlaps with node, Publication Date May 13, 2022, Retrieved Date Jul. 8, 2025, Retrieved from Internet, https://tex.stackexchange.com/questions/644097/tikz-arrow-tip-overlaps-with-node, pp. 2.

Medfusion™, "Medfusion Syringe Infusion Pump Model 4000", Operator's Manual, Software Version V1.1, Sep. 2011, pp. 154. <http://www.medfusionpump.com/assets/literature/manuals/Operators_Manual_4000_40-5760-51A.pdf>.

Panasonic, Reference Manual Personal Computer Model No. CF-31 Series, 2010, Panasonic Corporation, PCE0301A_XP/7, pp. 129.

"Sigma Spectrum: Operator's Manual", May 15, 2008, pp. 63. <https://usme.com/content/manuals/sigma-spectrum-operator-manual.pdf>.

"Sigma Spectrum: Operator's Manual", Oct. 2009, pp. 72. <http://static.medonecapital.com/manuals/userManuals/Sigma-Spectrum-Operator-Manual-October-2009.pdf>.

Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. <http://www.thomasland.com/hpj4209-832.pdf>.

"Software Versioning", Wikipedia.org, dated Oct. 16, 2011 in 11 pages, <https://en.wikipedia.org/w/index.php?title=Software_versioning&oldid=455859110>.

Sony, Bloggie Handbook Mobile HD Snap Camera M Hs-FS 1 /FS 1 k/FS2/FS2k, 2011, Sony Corporation 4-275-040-12(1), pp. 80.

Sony, Sony Camera and Camcorder Battery Information, 2010, sony.com via Wayback Machine, Article ID: S1Q0399, https://web.archive.org/web/20210126195509/https://www.sony.com/electronics/support/dvd-camcorders-dcr-dvd-series/dcr-dvd101/articles/S1Q0399, pp. 3.

Zhou et al., "Performance-Aware Thermal Management via Task Scheduling", ACM Transactions on Architecture and Code Optimization, May 7, 2010, vol. 7, Issue 1, No. 5, pp. 31.

International Search Report and Written Opinion received in PCT Application No. PCT/US2008/087484, dated May 4, 2009 in 8 pages.

Abbott Laboratories, "LifeCare® 5000, Plum®: Concurrent Flow Infusion System with DataPort™", System Operating Manual, Version 1.6, Jul. 1998, pp. 76.

Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.

ALARIS® Medical Systems, "Signature Edition® GOLD—Single & Dual Channel Infusion System", San Diego, CA, USA, date unknown, but believed to be at least as early as Nov. 29, 2008, pp. 2-88 & 2-91.

Allegro, "3955—Full-Bridge PWM Microstepping Motor Drive", Datasheet, 1997, pp. 16.

Amazon, Post-it Message "Sign Here" Flags, 30/Dispenser, 4 Dispensers/Pack, Published Sep. 29, 2016, https://www.amazon.com/Assorted-Color-Colors-Dispenser-MMM684SH/dp/B00006JNMN/?th=1, 2 pages.

Aragon, Daleen RN, Ph.D., CORN, "Evaluation of Nursing Work Effort and Perceptions About Blood Glucose Testing in Tight Glycemic Control", American Journal of Critical Care, Jul. 2006, vol. 15, No. 4, pp. 370-377.

Baxter, "Baxter Receives 510(k) Clearance for Next-Generation SIGMA Spectrum Infusion Pump with Master Drug Library" Press Release, May 8, 2014, pp. 2. <http://web.archive.org/web/20160403140025/http://www.baxter.com/news-media/newsroom/press-releases/2014/05_08_14_sigma.page>.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.

Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.

Buhrdorf et al., "Capacitive Micromachined Ultrasonic Transducers and their Application", Proceedings of the IEEE Ultrasonics Symposium, Feb. 2001, vol. 2, pp. 933-940.

Cannon, MD et al., "Automated Heparin-Delivery System to Control Activated Partial Thromboplastin Time", Circulation, Feb. 16, 1999, vol. 99, pp. 751-756.

"CareAware® Infusion Management", Cerner Store, as printed May 12, 2011, pp. 3, <https://store.cerner.com/items/7>.

Chen et al., "Enabling Location-Based Services on Wireless LANs", The 11th IEEE International Conference on Networks, ICON 2003, Sep. 28-Oct. 1, 2003, pp. 567-572.

Cheung et al., "Hyperglycemia is Associated with Adverse Outcomes in Patients Receiving Total Parenteral Nutrition", Diabetes Care, Oct. 2005, vol. 28, No. 10, pp. 2367-2371.

Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.

"Continually vs Continuously", <https://web.archive.org/web/20090813092423/http://www.diffen.com/difference/Continually_vs_Continuously>, as accessed Aug. 13, 2009 in 4 pages.

"CritiCore® Monitor: Critical Fluid Output and Core Bladder Temperature Monitor", BARD Urological Catheter Systems, Advertisement, 2005, pp. 2.

Daimiwal et al., "Wireless Transfusion Supervision and Analysis Using Embedded System", IEEE, 2010 International Conference ICBBT, China, Apr. 2010, pp. 56-60.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. <http://archive.epo.org/epo/pubs/oj013/11_13/11_5033.pdf>.

"Decision of the Administrative Council of Oct. 27, 2009 Amending the Implementing Regulations to the European Patent Convention (CA/D 20/09)", Official Journal EPO Dec. 2009, Dec. 2009, pp. 582-584. <http://archive.epo.org/epo/pubs/oj009/12_09/12_5829.pdf>.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

"Differential Pressure Transmitter, Series PD-39 X", SensorsOne Ltd., Advertisement, Dec. 2005, pp. 2.

Dunster et al., "Flow Continuity of Infusion Systems at Low Flow Rates", Anaesthesia and Intensive Care, Oct. 1995, vol. 23, No. 5, pp. 5.

File:Soldado, Raso Fuerza Aerea Boliviana.jpg, Feb. 9, 2021, https://commons.m.wikimedia.org/wiki/File:Soldado_Raso_Fuerza_A%C3%A9rea_Boliviana.jpg, 1 page.

(56) References Cited

OTHER PUBLICATIONS

Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Fresenius, "Infusion Workstation: Orchestra® Base Intensive", Operator's Guide, Jun. 20, 2006, <https://manualmachine.com/fresenius/orchestrabaseunit/7455278-user-manual/>, 24 pages.
"Froth", <http://www.merriam-webster.com/dictionary/froth>, as accessed May 13, 2015 in 1 page.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. <www.hospira.com/products_and_services/infusion_pumps/plum/index>.
Hospira, "Plum XL™ Series Infusion System" Technical Service Manual, Feb. 2005, Lake Forest, Illinois, USA, pp. i-vii, 5-14, 8-3.
"ICU Medical Receives FDA Clearance for New Infusion Pump", Medical Design & Development Staff, Aug. 29, 2023, https://www.medicaldesigndevelopment.com/topics/devices/news/22871498/icu-medical-receives-fda-clearance-for-new-infusion-pump, 2 pages.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
JMS Co., Ltd., "Infusion Pump: OT-701", Tokyo, Japan, 2002, pp. 4.
Junda, Lin, "Global development trends of green bonds", Jul. 10, 2018, pp. 9.
Jusko: Moving from Basic Toward Systems Pharmacodynamic Models; Department of Pharmaceutical Sciences, School of Pharmacy and Pharmaceutical Sciences, State University of New York at Buffalo, Buffalo, New York 14214; Journal of Pharmaceutical Sciences, vol. 102, No. 9, Sep. 2013; DOI 10.1002/jps; in 11 pages.
Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.
Kutcher et al., "The Effect of Lighting Conditions on Caries Interpretation with a Laptop Computer in a Clinical Setting", Elsevier, Oct. 2006, vol. 102, No. 4, pp. 537-543.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Lesson 1: Introduction to Pharmacokinetics and Pharmacodynamics; Concepts in Clinical Pharmacokinetics; in 18 pages.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Meibohm, et al; Basic Concepts of Pharmacokinetic/pharmacodynamic (PK/PD) modelling; Department of Pharmaceutics, College of Pharmacy, University of Florida, Gainesville, FL, USA, International Journal of Clinical Pharmacology and Therapeutics, vol. 35, No. Oct. 1997 (401-413); 13 pages.
Merry et al., "A New, Safety-Oriented, Integrated Drug Administration and Automated Anesthesia Record System", Anesthesia & Analgesia, Aug. 2001, vol. 93, No. 2 pp. 385-390.
Microchip Technology Inc., "MTA11200B; TrueGauge™ Intelligent Battery Management I.C.", <https://www.elektronik.ropla.eu/pdf/stock/mcp/mta11200b.pdf>, 1995, pp. 44.
Moghissi, Etie, MD, FACP, FACE, "Hyperglycemia in Hospitalized Patients", A Supplement to ACP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Safer Care Victoria: Dobutamine I Safer Care Victoria; https://www.safercare.vic.gov.au/clinical-guidance/critical/dobutamine; in 9 pages.
Safer Care Victoria: Dopamine I Safer Care Victoria; https://www.safercare.vic.gov.au/clinical-guidance/critical/dopamine; in 9 pages.
Safer Care Victoria: Adrenaline (epinephrine) I Safer Care Victoria; https://www.safercare.vic.gov.au/clinical-guidance/critical/adrenaline-epinephrine; in 9 pages.
Safer Care Victoria: Isoprenaline I Safer Care Victoria; https://www.safercare.vic.gov.au/clinical-guidance/critical/isoprenaline; in 8 pages.
Safer Care Victoria: Noradrenaline (norepinephrine) I Safer Care Victoria; https://www.safercare.vic.gov.au/clinical-guidance/critical/noradrenaline-norepinephrine; in 8 pages.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS-Thomson Microelectronics, "L6219—Stepper Motor Drive", Datasheet, Dec. 1996, pp. 10.
SGS-Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.
Tang et al., "Linear Dimensionality Reduction Using Relevance Weighted LDA", Pattern Recognition, 2005, vol. 38, pp. 485-493, <http://staff.ustc.edu.cn/~ketang/papers/TangSuganYaoQin_PR04.pdf>.
The heart.org Medscape: nitroglycerin IV (Rx); glyceryl trinitrate IV, IV Nitroglycerin (nitroglycerin IV) dosing, indication, interaction, adverse effects, and more; https://reference.medscape.com/drug/glyceryl-trinitrate-iv-iv-nitroglycerin-nitroglycerin-iv-342278#10; 1 page.
Thomas et al., "Implementation of a Tight Glycaemic Control Protocol Using a Web-Based Insulin Dose Calculator", Anaesthesia, 2005, vol. 60, pp. 1093-1100.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph. D., et al., "Intensive Insulin Therapy in the Medical ICU", The New England Journal of Medicine, Feb. 2, 2006, vol. 354, No. 5, pp. 449-461.
Westbrook et al., "Errors in the Administration of Intravenous Medications in Hospital and the Role of Correct Procedures and Nurse Experience", BMJ Quality & Safety, 2011, vol. 20, pp. 1027-1034.
Zakariah et al., "Combination of Biphasic Transmittance Waveform with Blood Procalcitonin Levels for Diagnosis of Sepsis in Acutely

(56) References Cited

OTHER PUBLICATIONS

Ill Patients", Critical Care Medicine, 2008, vol. 36, No. 5, pp. 1507-1512.

* cited by examiner

995

2200

INFUSION PUMP WITH CRITICAL CARE AREA AND DRUG LIBRARY SETTINGS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention relates to medical devices. More specifically, the invention relates to infusion pumps that include touch screen graphical user interfaces.

BACKGROUND

Graphical user interfaces for medical devices that display patient and treatment information have improved clinician efficiency when caring for patients. However, a challenge for designing graphical user interfaces is the need to balance the amount of information displayed on any one screen viewable by the clinician with the need to create a device that is easy to read and navigate. Too often the user is presented with an overwhelming amount of information, impeding the interaction between the user and the user interface.

Additionally, medical devices, including medical pumps, can be complicated and time-consuming for caregivers to program. The need for an improved graphical interface is critical to maintain efficiency of patient care and to reduce potential clinical errors and thereby improve patient safety. Device interfaces that increase input efficiency and accuracy are critical to improve patient safety and therapy.

Graphical user interface design must also take into account strict design parameters as well as safety parameters. As a result, many medical devices do not provide flexibility in programming parameters, neither for the administrator nor for the clinician.

SUMMARY

A method and apparatus system is disclosed for operating a medical device with or without a cassette in place. A method is disclosed for adding additional VTBI to an ongoing infusion without stopping the infusion and with maintaining the infusion parameters. A method and system is disclosed for changing the CCA without having to interrupt or completely stop an ongoing infusion. Quick titration buttons are provided to allow improved navigation between various delivery display screens.

The aforementioned and other features and advantages will become further apparent from the following detailed description of the presently preferred embodiments, read in conjunction with the accompanying drawings. The detailed description and drawings are merely illustrative rather than limiting, the scope of the invention being defined by the appended claims and equivalents thereof.

DETAILED DESCRIPTION OF THE PREFERRED EMBODIMENT

This will be described as it applies to its preferred embodiment. It is not intended to be limited to the preferred embodiment. It is intended to cover all modifications and alternatives that may be included within the scope of the appended claims.

Figure 1:
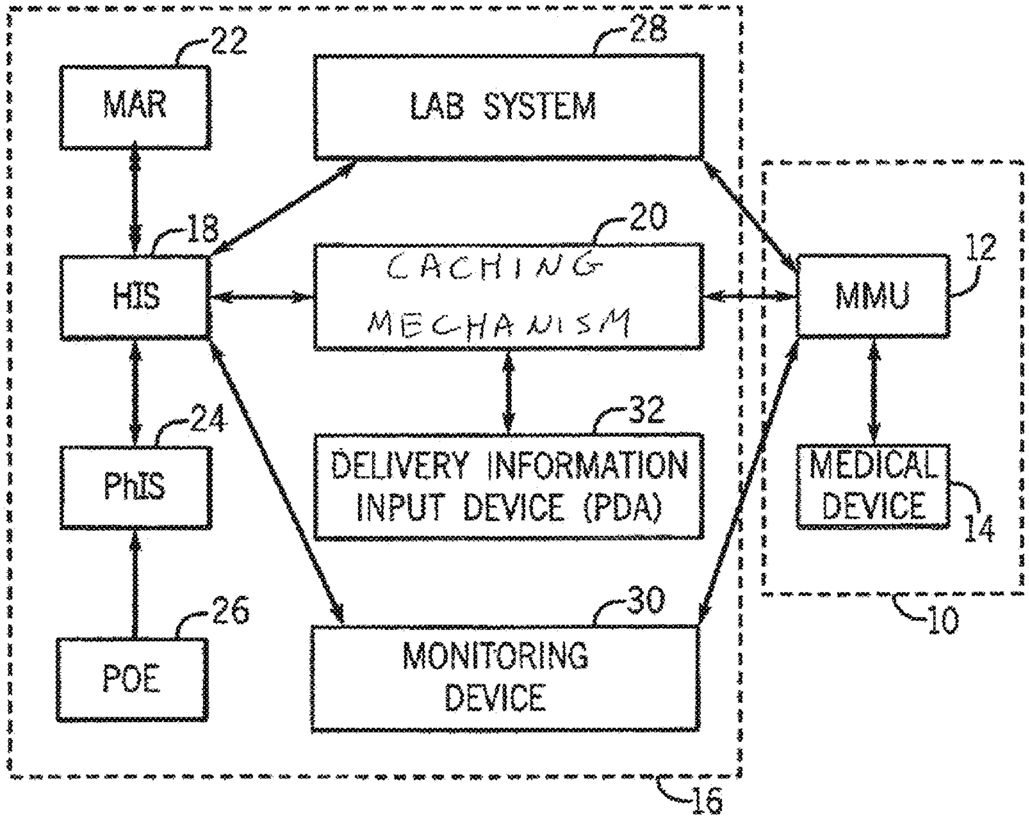
FIG. 1 is a schematic diagram of the medication management system including a medication management unit and a medical device, integrated with an information system.

With reference to FIG. 1, the medication management system (MMS) 10 includes a medication management unit (MMU) 12 and a medical device 14, typically operating in conjunction with one or more information systems or components of a hospital environment 16. The term hospital environment should be construed broadly herein to mean any medical care facility, including but not limited to a hospital, treatment center, clinic, doctor's office, day surgery center, hospice, nursing home, and any of the above associated with a home care environment. As discussed below, there can be a variety of information systems in a hospital environment. As shown in FIG. 1, the MMU 12 communicates to a hospital information system (HIS) 18 via a caching mechanism 20 that is part of the hospital environment 16.

It will be understood by those of skill in art that the caching mechanism 20 is primarily a pass through device for facilitating communication with the HIS 18 and its functions can be eliminated or incorporated into the MMU 12 (FIG. 1) and/or the medical device 14 and/or the HIS 18 and/or other information systems or components within the hospital environment 16. The caching mechanism 20 provides temporary storage of hospital information data separate from the HIS 18, the medication administration record system (MAR) 22, pharmacy information system (PhIS) 24, physician order entry (POE) 26, and/or Lab System 28. The caching mechanism 20 provides information storage accessible to the Medication Management System 10 to support scenarios where direct access to data within the hospital environment 16 is not available or not desired. For example, the caching mechanism 20 provides continued flow of information in and out of the MMU 12 in instances where the HIS 18 is down or the connectivity between the MMU 12 and the electronic network (not shown) is down.

The HIS 18 communicates with a medication administration record system (MAR) 22 for maintaining medication records and a pharmacy information system (PhIS) 24 for delivering drug orders to the HIS. A physician/provider order entry (POE) device 26 permits a healthcare provider to deliver a medication order prescribed for a patient to the hospital information system directly or indirectly via the PhIS 24. One skilled in the art will also appreciate that a medication order can be sent to the MMU 12 directly from the PhIS 24 or POE device 26. As used herein the term medication order is defined as an order to administer something that has a physiological impact on a person or animal, including but not limited to liquid or gaseous fluids, drugs or medicines, liquid nutritional products and combinations thereof.

Lab system 28 and monitoring device 30 also communicate with the MMU 12 to deliver updated patient-specific information to the MMU 12. As shown, the MMU 12 communicates directly to the lab system 28 and monitoring device 30. However, it will be understood to those of skill in art that the MMU 12 can communicate to the lab system 28 and monitoring device 30 indirectly via the HIS 18, the caching mechanism 20, the medical device 14 or some other intermediary device or system.

Delivery information input device 32 also communicates with the MMU 12 to assist in processing drug orders for delivery through the MMU 12. The delivery information input device 32 can be any sort of data input means, including those adapted to read machine readable indicia such as barcode labels; for example a personal digital assistant (PDA) with a barcode scanner. Hereinafter the delivery information input device 32 will be referred to as input device 32. Alternatively, the machine readable indicia may be in other known forms, such as radio frequency identification (RFID) tag, two-dimensional bar code, ID matrix, transmitted radio ID code, human biometric data such as fingerprints, etc. and the input device 32 adapted to "read" or recognize such indicia. The input device 32 is shown as a separate device from the medical device 14; alternatively, the input device 32 communicates directly with the medical device 14 or may be integrated wholly or in part with the medical device.

Figure 2:
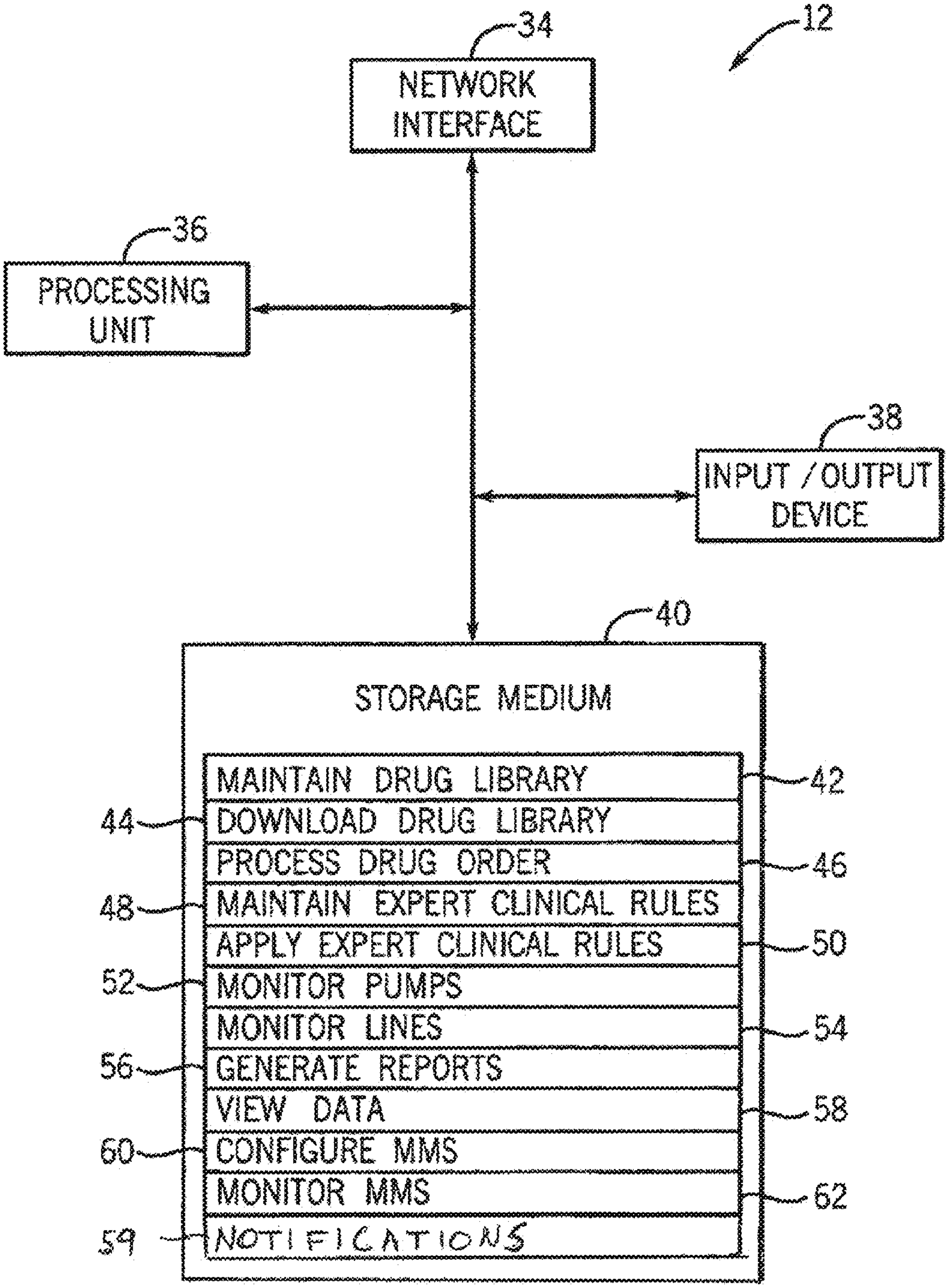
FIG. 2 is a schematic diagram of the medication management unit.

With reference to FIG. 2, the medication management unit 12 includes a network interface 34 for connecting the MMU 12 to multiple components of a hospital environment 16, one or more medical devices 14, and any other desired device or network. A processing unit 36 is included in MMU 12 and performs various operations described in greater detail below. A display/input device 38 communicates with the processing unit 36 and allows the user to receive output from processing unit 36 and/or input information into the processing unit 36. Those of ordinary skill in the art will appreciate that display/input device 38 may be provided as a separate display device and a separate input device.

An electronic storage medium 40 communicates with the processing unit 36 and stores programming code and data necessary for the processing unit 36 to perform the functions of the MMU 12. More specifically, the storage medium 40 stores multiple programs formed for various functions of the MMU 12 including but not limited to the following programs: Maintain Drug Library 42; Download Drug Library 44; Process Drug Order 46; Maintain Expert Clinical Rules 48; Apply Expert Clinical Rules 50; Monitor Pumps 52; Monitor Lines 54; Generate Reports 56; View Data 58; Configure the MMS 60; and Monitor the MMS 62. The Maintain Drug Library 42 program creates, updates, and deletes drug entries and establishes a current active drug library. The Download Drug Library 44 program updates medical devices 14 with the current drug library. The Process Drug Order 46 program processes the medication order for a patient, verifying that the point of care (POC) medication and delivery parameters match those ordered. The Maintain Expert Clinical Rules 48 program creates, updates, and deletes the rules that describe the hospital's therapy and protocol regimens. The Apply Expert Clinical Rules 50 program performs logic processing to ensure safety and considers other infusions or medication orders, patient demographics, and current patient conditions. The Monitor Pumps 52 program acquires ongoing updates of status, events, and alarms transmitted both real-time and in batch mode, as well as tracking the location, current assignment, and software versions such as the drug library version residing on medical device 14. The Monitor Lines 54 program acquires ongoing updates of status, events and alarms for each channel or line for a medical device 14 that supports multiple drug delivery channels or lines. The Generate Reports 56 program provides a mechanism that allows the user to generate various reports of the data held in the MMU storage medium 40. The View Data 58 program provides a mechanism that supports various display or view capabilities for users of the MMU 12. The Notifications 59 program provides a mechanism for scheduling and delivery of events to external systems and users. The Configure the MMS 60 program provides a mechanism for system administrators to install and configure the MMS 10. The Monitor the MMS 62 program enables information technology operations staff capabilities to see the current status of MMS

10 components and processing, and other aspects of day-to-day operations such as system start up, shut down, backup and restore.

Figure 3:
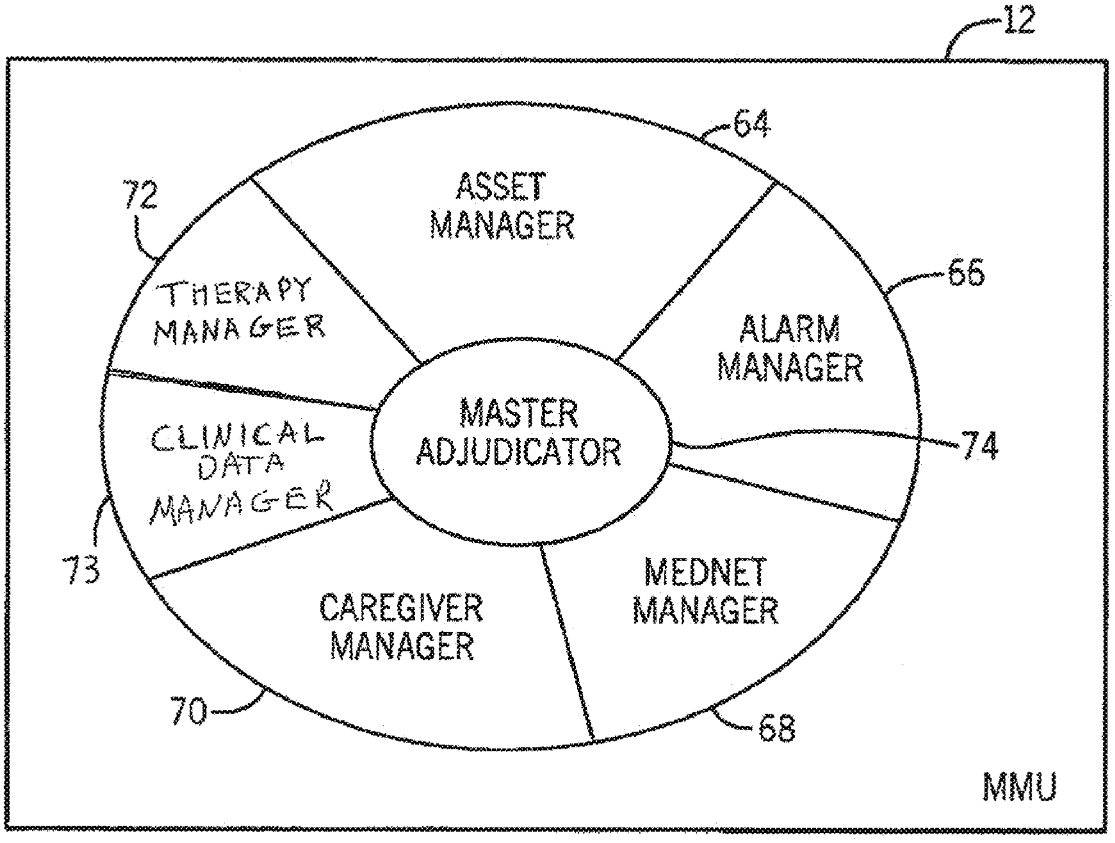
FIG. 3 is a schematic diagram illustrating some of the major functions performed by the medication management unit.

With reference to FIG. 3, the various functional programs 42-62 of the MMU 12, each including separate features and rules, are partitioned (at a higher level than shown in FIG. 2) and logically organized into interrelated managing units of the MMU 12. As shown, the MMU 12 includes an asset manager 64, an alarm manager 66, a drug library manager (such as, for example, is included in HOSPIRA MEDNET software) 68, a caregiver manager 70, a therapy manager 72, and/or a clinical data manager 73. However, one of ordinary skill in the art will appreciate that additional or alternative hospital system managing units can be provided. Additionally, the MMU 12 includes a master adjudicator 74 between the separate interrelated hospital system managing units 64-73 of the MMU 12, to regulate the interaction between the separate management units.

Further, while the MMU 12 as described herein appears as a single device, there may be more than one MMU 12 operating harmoniously and sharing the same database. For example the MMU 12 can consist of a collection of MMU specific applications running on distinct servers in order to avoid a single point of failure, address availability requirements, and handle a high volume of requests. In this example, each individual server portion of the MMU 12 operates in conjunction with other server portions of the MMU 12 to redirect service requests to another server portion of the MMU 12. Additionally, the master adjudicator 74 assigns redirected service requests to another server portion of the MMU 12, prioritizing each request and also ensuring that each request is processed.

With reference to FIGS. 2 and 3, the managing units 64-72 each include separate features and rules to govern their operation. For example, the asset manager 64 governs the execution of the Monitor Pumps 52 and Monitor Lines 54 programs; the drug library manager 68 governs the execution of the Drug Library 42 and Download Drug Library 44 programs; the therapy manager 72 governs the execution of the Process Drug Order 46, Maintain Expert Clinical Rules 48, and Apply Expert Clinical Rules 50 programs; and the clinical data manager 73 governs the execution of the Generate Reports 56 and View Data 58 programs. Other distribution of the functional MMU programs 42-62 among the hospital system managing units 64-73 can be made.

Figure 4:
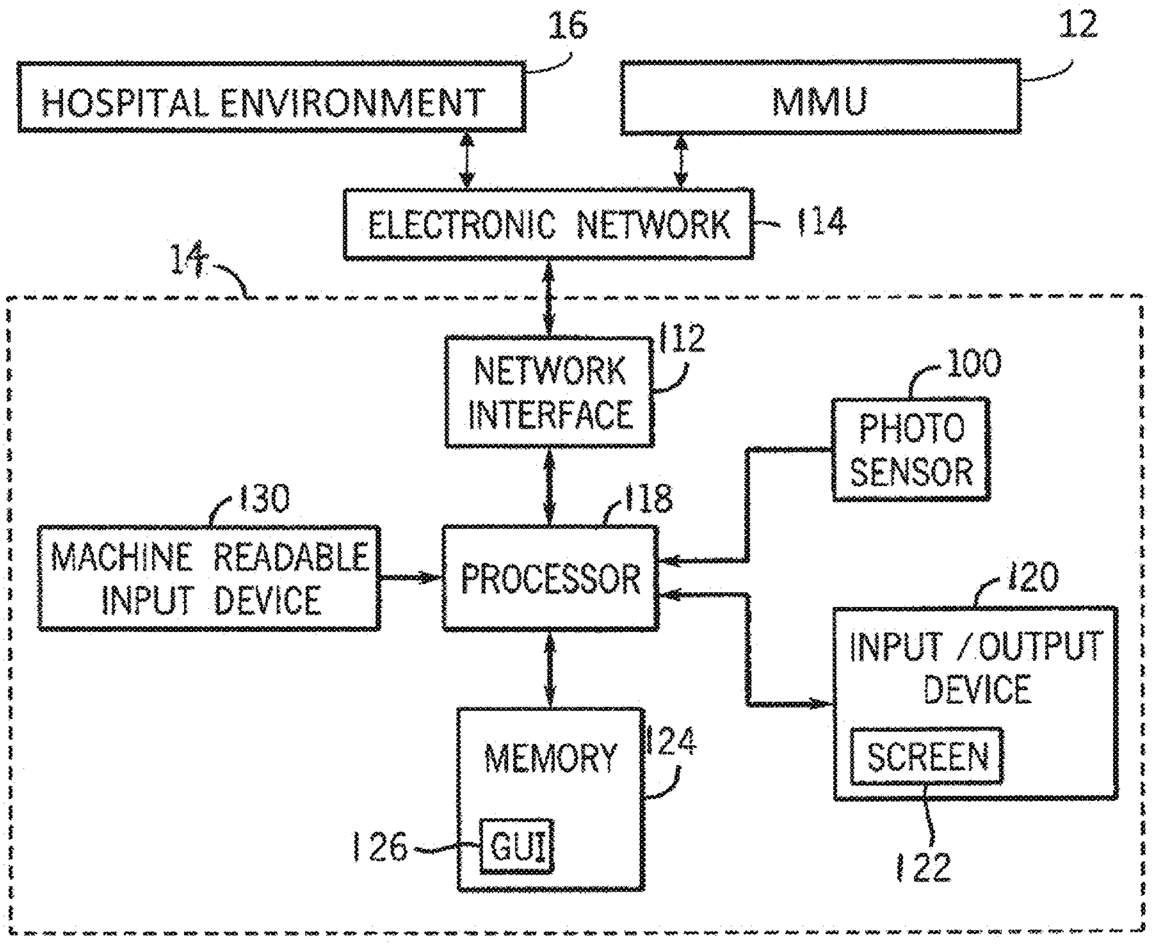
FIG. 4 is a schematic diagram of a medical device.

With reference to FIG. 4, an electronic network 114 connects the MMU 12, medical device 14, and hospital environment 16 for electronic communication. The electronic network 114 can be a completely wireless network, a completely hard wired network, or some combination thereof.

FIG. 4 is a schematic diagram illustrating several functional components of a medical device 14. Those of ordinary skill in the art will appreciate that the device 14 includes many more components than those shown in FIG. 4. However, it is not necessary that all these components be shown in order to disclose an illustrative embodiment.

The term "medical device" includes without limitation a device that acts upon a cassette, reservoir, vial, syringe, or tubing to convey medication or fluid to or from a patient (for example, an enteral pump, a parenteral infusion pump, a patient controlled analgesia (PCA) or pain management medication pump, or a suction pump), a monitor for monitoring patient vital signs or other parameters, or a diagnostic, testing or sampling device.

Figure 5:
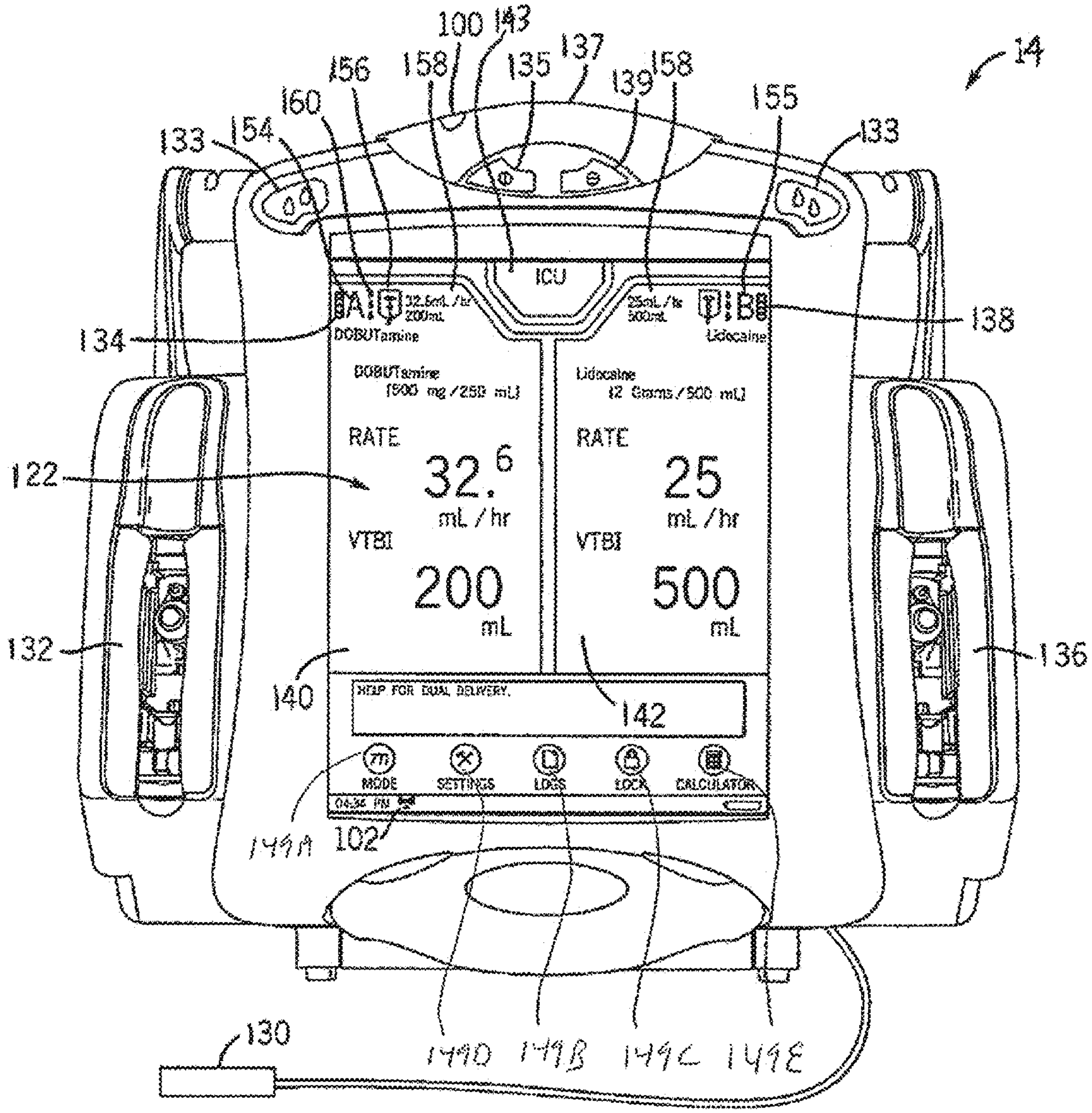
FIG. 5 is perspective view of a multi-channel medical device in communication with a machine-readable input device and shows a split screen display, having one portion associated with each channel, which is adapted to be displayed and viewed from afar during normal delivery of fluid.

With reference to FIG. 5, for the purpose of exemplary illustration only, the medical device 14 is disclosed as an infusion pump. More particularly, the medical device 14 can be a single channel infusion pump, a multi-channel infusion pump (as shown), or some combination thereof.

With reference to FIG. 4, the pump style medical device 14 includes a network interface 112 for connecting the medical device 14 to electronic network 114. Where a wireless connection to the electronic network 114 is desired, network interface 112 operates an antenna for wireless connection to the electronic network 114. The antenna can project outside the device 14 or be enclosed within the housing of the device.

A processor 118 is included in the medical device 14 and performs various operations described in greater detail below. The input/output device 120 allows the user to receive output from the medical device 14 and/or input information into the medical device 14. Those of ordinary skill in the art will appreciate that input/output device 120 may be provided as a single device such as a touch screen 122, or as a separate display device and a separate input device (not shown). In the preferred embodiment, the display screen 122 of the medical pump 14 is a thin film transistor active matrix color liquid crystal display with a multi-wire touch screen. A membrane generally impermeable to fluids overlays the display screen 122 so the user can press on images of keys or buttons on the underlying screen with wet gloves, dry gloves or without gloves to trigger an input.

A memory 124 communicates with the processor 118 and stores code and data necessary for the processor 118 to perform the functions of the medical device 14. More specifically, the memory 124 stores multiple programs formed for various functions of the medical device 14 including a graphical user interface program 126 with multiple subparts described in greater detail below.

With reference to FIG. 5, this provides a machine-readable input device 130. The machine-readable input device 130 communicates with the medical device 14 to input machine-readable information to the medical device 14. The machine-readable input device 130 can communicate, directly or indirectly, with the medical device 14 via a wireless or hard-wired connection. The machine-readable input device 130 can be a device that is separate from but associated or in communication with the medical device 14. The machine-readable input device 130 can be any sort of data input means, including those adapted to read machine-readable indicia, such as a barcode scanner or handheld personal digital assistant (PDA). Alternatively, the machine-readable input device 130 may be operable to read in other known forms of machine-readable information, such as radio frequency identification tags (RFID), touch memory, digital photography, biometrics, etc.

With reference to FIG. 5, the medical device 14 is a multichannel pump having a first channel 132 with first channel machine-readable label 134 and a second channel 136 with a second channel machine-readable label 138. A user of the medical device 14 operates the machine-readable input device 130 to select a channel from one or more channels 132 and 136, by scanning in the associated machine-readable label 134 or 138.

The user selects the desired channel 132 or 136 by using the machine-readable input device 130 to scan a factory or hospital programmed, unique, machine-readable label 134 or 138 that is electronically generated and presented on the screen 122, preferably juxtapositioned near the respective channel 132 or 136. Alternatively, the machine-readable labels 134 and 138 are physically affixed to the medical device 14, preferably on or juxtapositioned near the channel 132 and 136, respectively. Since the machine-readable labels 134 and 138 are generated and/or can be stored in memory 124 by the pump 14, the pump 14 can associate the machine-readable labels 134 and 138 to the channels 132 or 136. The pump 14 then allows the user to program and activate the selected channel 132 or 136. The user may also manually select the desired channel by touching an appropriate folder tab on the touch screen. The folder tabs are labeled and/or physically arranged on the screen so as to be proximate to the corresponding channel 132 or 136.

In a further aspect of the wireless embodiment, all the medical devices can periodically broadcast a unique wireless device/channel IP address and/or a self-generated unique machine-readable label (for example, a barcode) 134 or 138 that can also be presented on the screen 122. Alternatively, the machine-readable labels 134 and 138 are physically affixed to or posted on the medical device 14. Each medical device will correlate such broadcasted or posted device/channel IP addresses and/or barcodes with a particular patient, who is also identified by a unique machine readable label (not shown) or patient IP address. The user associates the desired pump(s) or channel(s) 132, 136 with the patient by using the machine-readable input device 130 to scan the unique machine-readable labels 134, 138 and the patient's machine readable label. This causes the appropriate pump processor(s) 118 to associate the appropriate pump channel(s) 132, 136 with the patient. Then the pumps or channels can associate, communicate, and coordinate with each other wirelessly.

With reference to FIGS. 4, 5, 5A and 17 A to 17C, the graphical user interface program 126 reallocates screen 122 for a medical device 14. Specifically, FIGS. 5 and 17B illustrates a multi-channel infusion pump 14 with a split touch screen 122 having a first channel screen portion 140 associated with first channel 132 and a second channel screen portion 142 associated with the second channel 136. Each channel screen portion 140 and 142 presents a subset of the delivery information regarding the respective channels 132 or 136, including without limitation therapeutic agent name, concentration, dose rate, VTBI, and alarm information, in a font size that it is easily readable by a user from a distance such as, for example, from approximately fifteen to twenty feet (4.6-6.2 meters) away. This is what is referred to as a "far view" delivery screen. The far view delivery screens display subsets of the information found on the relevant "near view" delivery screens, illustrated in FIG. 17 A and 17C. The near view delivery screen displays information such as, drug name, concentration, dose rate, time remaining, VTBI, volume remaining, and alarm name for the highest priority alarm if in an alarm state.

Figure 5A:
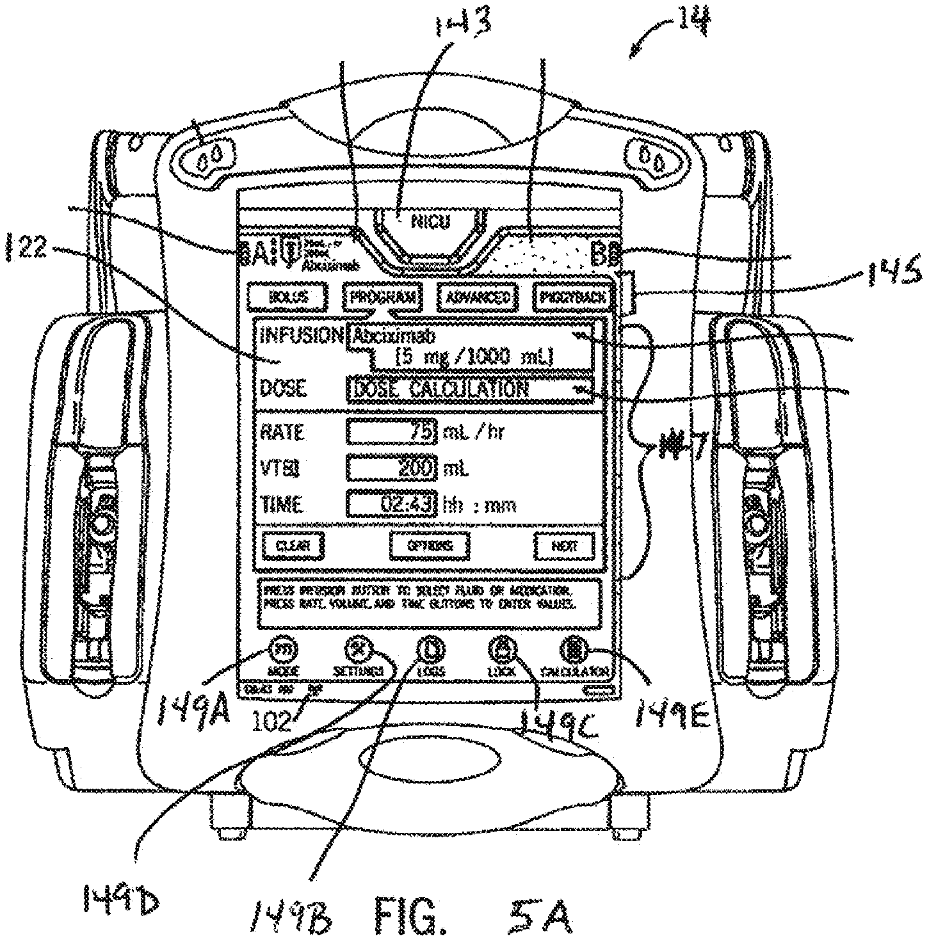
FIG. 5A is a perspective view similar to FIG. 5 and illustrates a near view display screen.
Figure 17A:
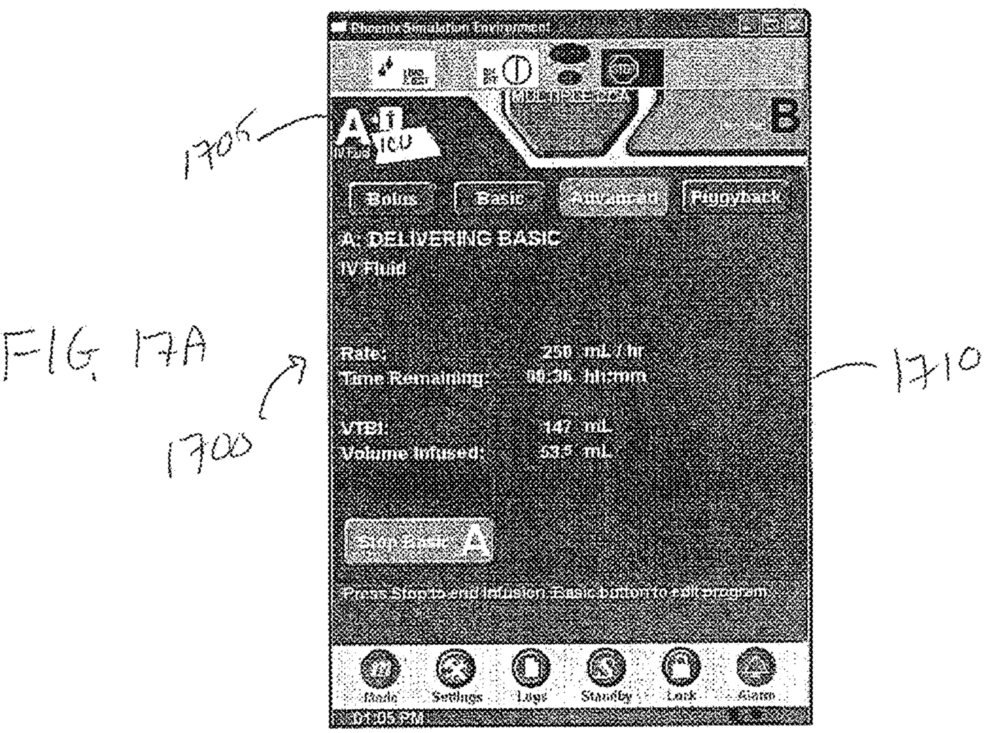
FIGS. 17A to 17C are screen shots illustrating a graphical user interface navigation button.
Figure 17B:
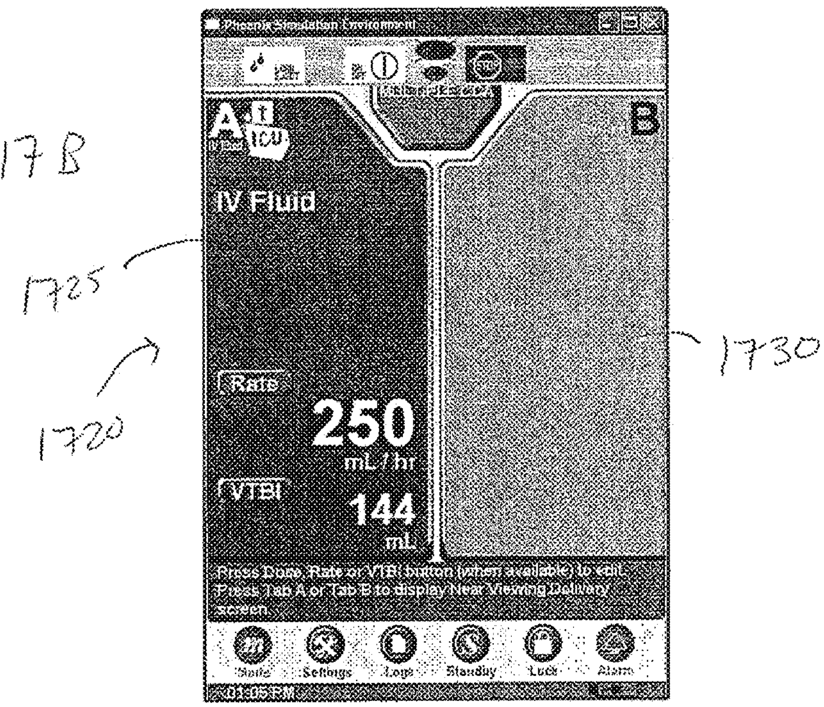
Figure 17C:
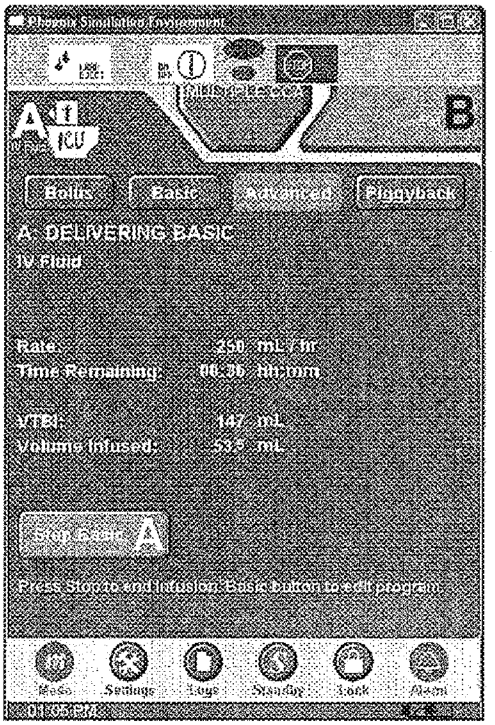

In practice, the delivery screen displays a near view when the user is programming the device as illustrated by FIG. 5A. The near view delivery screen will switch to the far view delivery screen after a predetermined period of time that is predetermined by the manufacturer, configurable by the facility via the drug library, and/or set by the caregiver at the pump, for example after 20 seconds. Often, the user does not want to wait for the predetermined length of time to view the far screen. FIGS. 17 A to 17C illustrate one embodiment of a medical device that allows the user to switch from the near view screen to the far view screen and vice versa at any time. FIG. 17A illustrates a near view screen for channel A 1705. If, while in the near view screen, the user wants to view the far view screen, the user touches anywhere within the body 1710 of the near view screen. Touching the body 1710 of the near view screen displays the far view screen 1720 illustrated in FIG. 17B. Referring to FIG. 17B, upon a user touching one of the tabs "A" or "B" or anywhere on the channel screen portions 1725 or 1730 of the far view delivery screen, a "near view" delivery screen is presented on the screen (FIG. 17C). In one embodiment, the user touches a "hotspot" or special toggle button within the body of the current display screen to return to either the far view screen or the near view screen.

Figure 18:
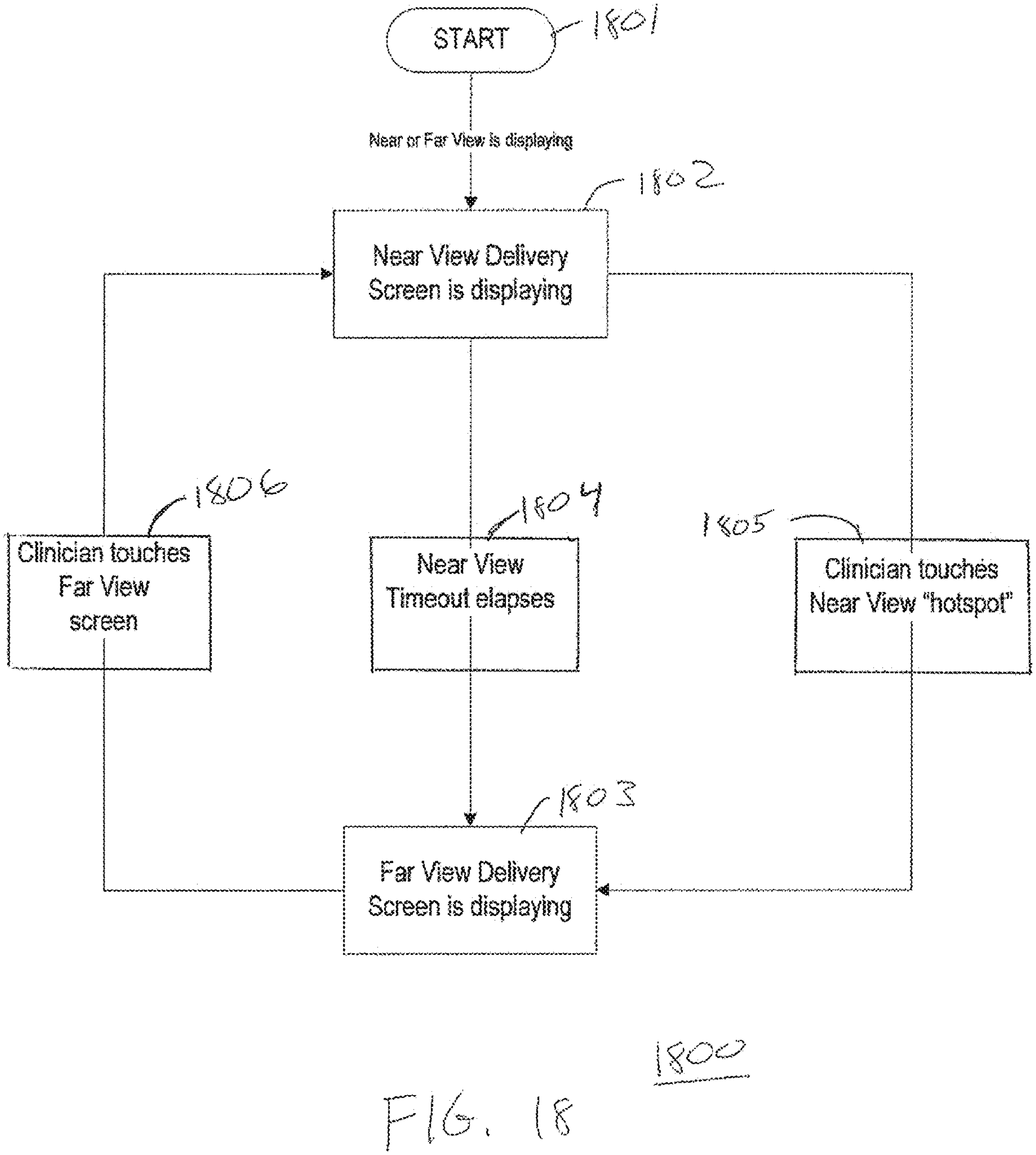
FIG. 18 is a flow chart for a program for determining a screen view display parameter.

Referring to FIG. 18, a flow chart for a program 1800 to immediately transition the display screen between the near view screen and the far view screen is illustrated. Program 1800 begins at block 1801 and progresses to block 1802 where the program determines that the near view delivery screen is displayed. In one aspect of the invention, program 1800 progresses in block 1804 to block 1803 when a near view time out elapses. In another aspect of the invention, program 800 moves from block 1802 to block 1803 when a user touches the near view hotspot in block 1805. Program 1800 may return to the near view screen, block 1802, from the far view screen, block 1803, when a user touches the far view screen in block 1806.

Returning to FIG. 5, the channel screen portion 140 or 142 selected or corresponding to the tab selected expands in area but the size of at least some of the text therein is shrunk, as shown in FIG. 17 A The shrinkage of one of the channel screen portions 140 and 142 and enlargement of its counterpart provides additional space for one or more data display or data entry fields to be placed on screen 122, as shown in FIG. 5A. As discussed below, data displays or data entry fields are placed on screen 122 in space previously occupied by portions of the channel screen portion 140 or 142. This reallocation of space on screen 122 perm its the user to enter inputs more easily since the data entry field can be large, preferably at least as large or, more preferably, larger in area than the original channel screen portions 140 and 142 were in the delivery screen mode. Additionally, the reallocation of space on screen 122 provides greater space for presenting information on the channel being adjusted or monitored. Further details on the reallocation of screen 122 and the near view and far view delivery screens can be found in commonly owned and co-pending application U.S. Ser. No. 11/103,235 entitled USER INTERFACE IMPROVEMENTS FOR MEDICAL DEVICES filed on Apr. 11, 2005, which is expressly incorporated herein in its entirety.

Referring again to FIG. 5, pump 14 includes dedicated or fixed tactile infuser buttons, and images of buttons on the LCD-touch screen 122. The fixed tactile buttons 133, 135, 137, and 139 provide the following functions: LOAD/EJECT button 133—opens and closes the cassette carriage; ON/OFF button 135—turns power on and off; ALARM SILENCE button 137—silences a silenceable alarm for a specified period of time, for example two minutes; and EMERGENCY STOP button 139—stops all channels.

The LCD color touch screen 122 allows the user to access and use on-screen button images, for example 3D button images, and data entry fields. The touch screen 122 uses a membrane over the LCD display so a single keypress does not cause significant infusion pole movement nor is it mistaken for a double keypress. The touch screen also accommodates a keypress whether the user is wearing wet gloves, dry gloves, or no gloves.

LCD touch screen button images 143, 145, 147 and 149A-149E are located as shown in FIGS. 5 and 5A and perform the following functions: Patient Information Tab 143—displays the clinical care area, preselected patient information (including without limitation name, ID number, etc.), and provides access to a more detailed patient information screen (FIG. 9C); Channel Level Therapy Buttons 145—accessed by button images on the infuser touch screen, are used to select an infusion therapy; Program Level Buttons 147—accessed by pressing areas, drop-down list triangles, boxes or text boxes on the programming screen, are used to select dose parameters of an infusion; and Device Level Buttons 149A-149E at the bottom of the touch screen are used to display and control device level features, including without limitation Mode 149A (for example, Operational or Biomed), Logs 149B, Locks 149C, Settings 149D, and Calculator display 149E. A wireless indicator image 102 displayed at the bottom of the screen 122 indicates that the device 14 is connected and ready for communication.

By using the Channel Level Therapy Buttons 145 and the Program Level Buttons 147, the healthcare practitioner can program each individual channel of the pump with specific fluid therapies in a variety of weight and body surface area-based units such as micrograms/kg/hour, grams/m2/hr, and other delivery specifications for the following modes: Basic Therapy-includes dose calculation, which allows dose rate programming based on volume to be infused (VTBI), drug amount, infusion time and drug concentration and simple rate programming that allows programming of volumetric rate (ml/hr) based upon VTBI and time; Bolus delivery—allows user to program a single uninterrupted discrete delivery based on dose amount and time (the bolus can be delivered from the primary or a secondary container); Piggyback delivery—allows user to program the delivery of a secondary infusion, to be delivered through the same cassette as the primary infusion (the primary infusion is paused until the piggyback VTBI completes); and Advanced Programming. Advanced Programming mode provides various types of programs including: Multistep-which allows a sequential delivery of fluid in up to 10 steps, with fluid volumes and delivery rates programmable for each step based on Rate and Volume or Volume and Time; Variable Time—which allows up to 24 dose calculation steps at specified clock times; Intermittent—a calculated dose or step to be delivered at regular intervals; and Taper—a delivery that ramps up and/or ramps down to a plateau rate.

With reference to FIGS. 4 and 5, the graphical user interface 126 provides channel indicators presented on screen 122. The channel indicators associate on-screen programming, delivery, and alarm information with a particular delivery channel by using graphical depictions such as a channel indication icon 154, 155. The channel indication icon 154 or 155 is a graphical item clearly associating on-screen programming, delivery, and alarm information with a specified associated delivery channel. The channel indication icons 154 and 155 are located on a tab 158 associated with a specified delivery channel of the medical device The channel indication icon 154 or 155 may include but is not limited to a user readable letter or number, a machine-readable indicator 134, or a combination thereof. The graphical user interface program 126 also provides a drip indicator icon 160 and an infusion status icon 156 presented on screen 122.

Figure 19A:
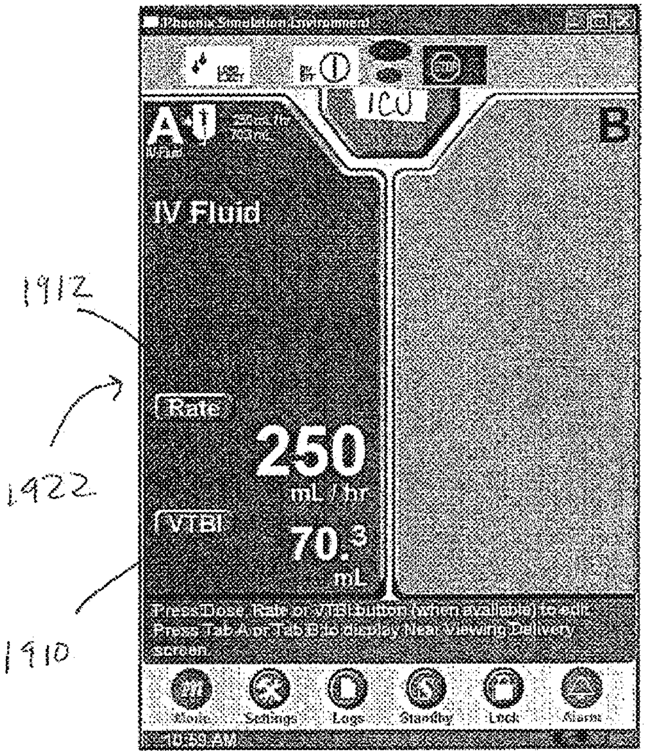
FIGS. 19A to 19G are screen shots illustrating additional graphical user interface navigation shortcut buttons.
Figure 19B:
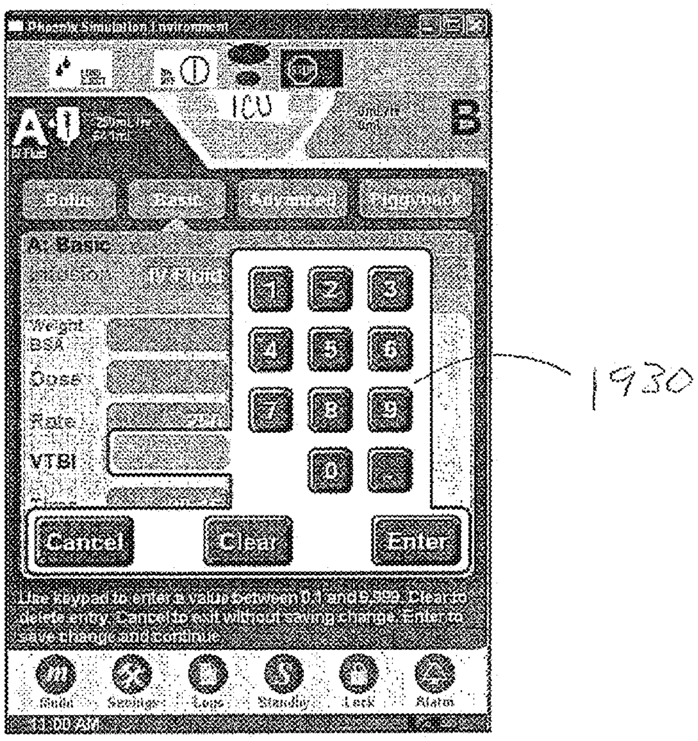
Figure 19C:
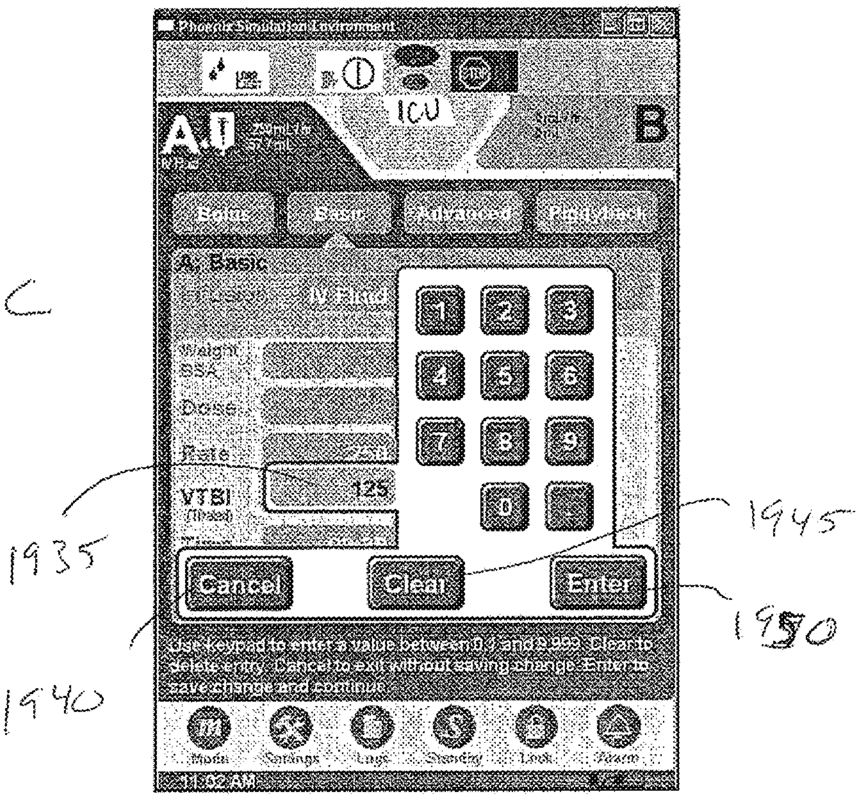
Figure 19D:
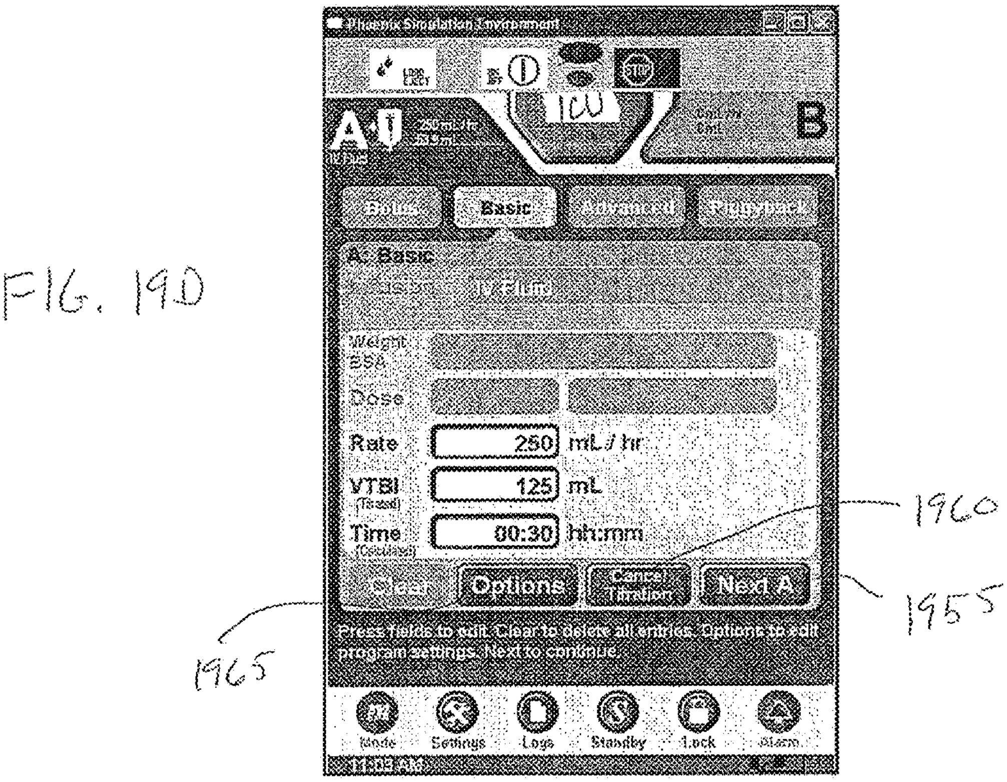
Figure 19E:
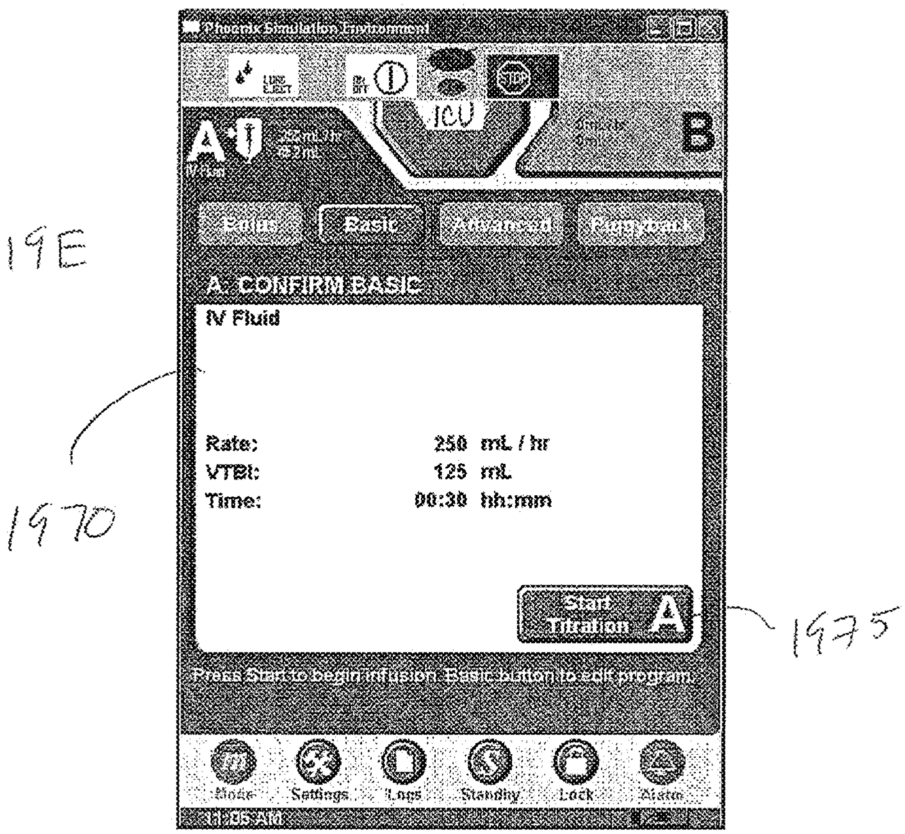
Figure 19F:
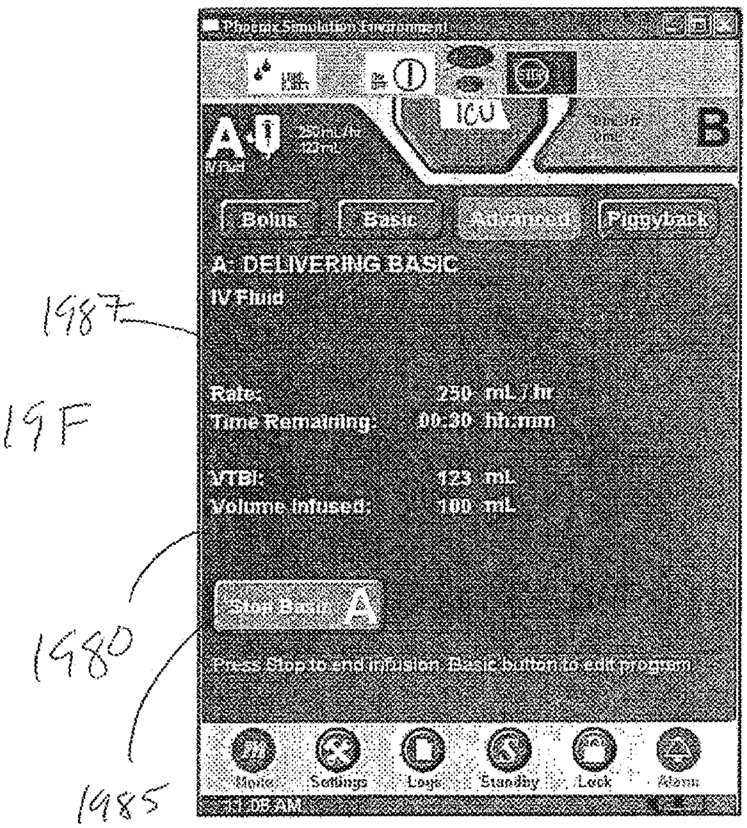
Figure 19G:
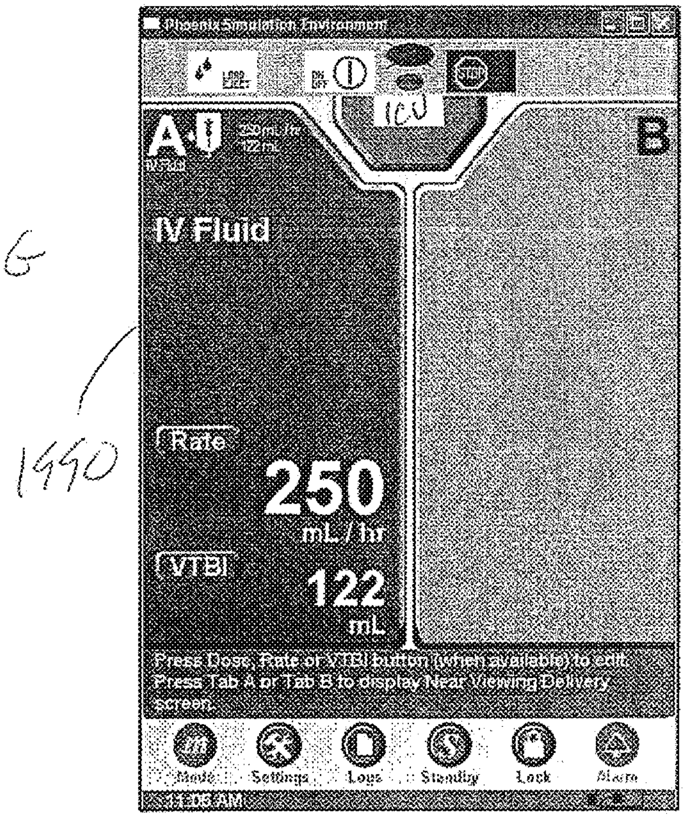

With reference to FIGS. 4, 5, 5A and 19A to 20, in one embodiment, the graphical user interface 126 provides quick titration buttons 1910, 1912 presented on a far view screen 122, 1922. FIG. 19A illustrates quick titration buttons for VTBI 1910 and Rate 1912. In another or the same embodiment, graphical user interface 1922 may also have a quick titration button for "dose" or other titration parameters. Quick titration buttons 1910, 1912 operate as explode or active buttons that when pressed take a user to a standard data entry field for data entry when the button is selected. In this manner, with one press of a button the user can be quickly taken to the desired data entry location rather than having to back track through several screens as is common. The quick titration buttons, thus, increase the user's efficiency in programming the medical device. FIGS. 19A to 19G illustrate the use of the VTBI quick titration button 1910. In practice, the user presses quick titration button 1910 (FIG. 19A) to bring up data entry field 1930 in FIG. 19B. In this embodiment, data entry field is a numerical keypad for entering a value for the VTBI. Once the desired value 1935 is entered, the user is prompted to use the keypad to cancel the entry by pressing the cancel button 1940, delete the entry by pressing the clear button 1945, or save the change and continue by pressing the enter button 1950 (FIG. 19C). FIG. 19D illustrates that the user pressed the enter button 1950 to accept and change the VTBI entry. At the graphical user interface illustrated in FIG. 19D, the user has the option to press "Next A" 1955 to continue, "Cancel Titration" 1960 to cancel the titration, or Options 1965 to edit the program. FIG. 19E illustrates that the user pressed "Next A" 1955 to continue. FIG. 19E illustrates a confirmation screen 1970. At this screen, the user is instructed to press "Start Titration A" 1975 to confirm the VTBI change and begin the infusion. At screen 1980 illustrated in FIG. 19F, the user can stop the titration by pressing "Stop Basic A" 1985. The near view screen 1980 illustrated in FIG. 19F returns to a far view screen 1990 shown in FIG. 19G.

Figure 20:
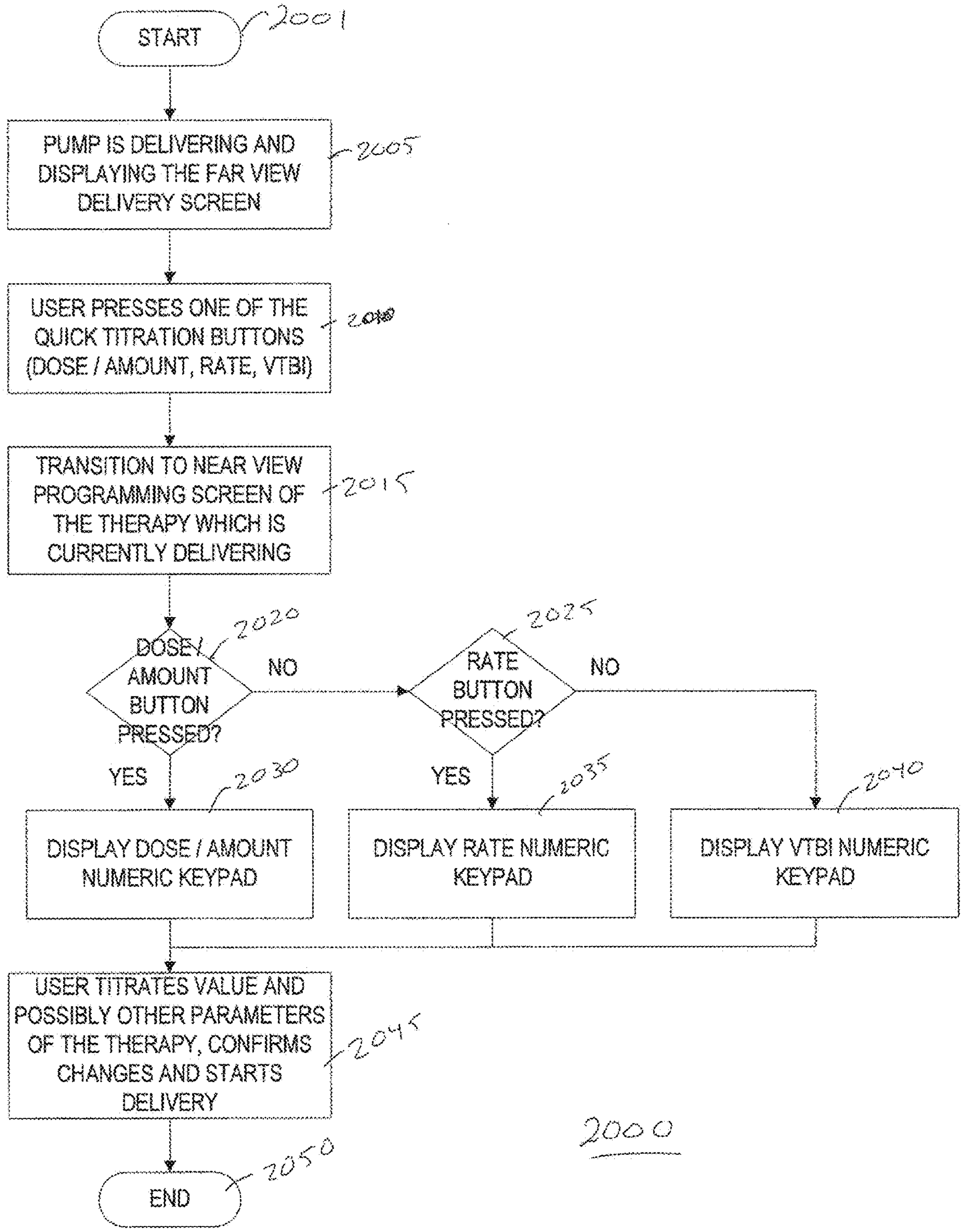
FIG. 20 is a flow chart for a program for determining a screen view display parameter based on the navigation shortcut buttons.

FIG. 20 is a flow chart of a program 2000 for operating quick titration buttons for "dose," "rate" and "VTBI" as discussed above. Program 2000 begins at block 2001 and progresses to block 2005 which indicates that the pump is delivering an infusion and displaying the far view delivery screen (see FIG. 19A). Program 2000 moves to block 2010 when a user presses one of the quick titration buttons 1910, 1912. In response to the pressing of the quick titration button, at block 2015 the program 2000 changes the display to the programming screen for the therapy which is currently delivering (e.g. Channel A or B). After the transition to the near view screen, program 2000 determines at blocks 2020 and 2025 which button was pressed. If the program determines that the Dose button was pressed the program displays the dose numeric keypad, block 2030. If the program determines that the rate button 1912 was pressed, the program displays the rate numeric keypad. If the program determines that neither the dose nor the rate button was pressed, the program displays the VTBI numeric keypad. Those with skill in the art will recognize that program 2000 can determine which button was pressed in any order other than that described herein. Once the keypad for the chosen button is displayed, the user inputs the desired data and continues with the program to confirm and run the infusion with the changed parameter as described above and illustrated in FIGS. 19A to 19G.

Figure 14:
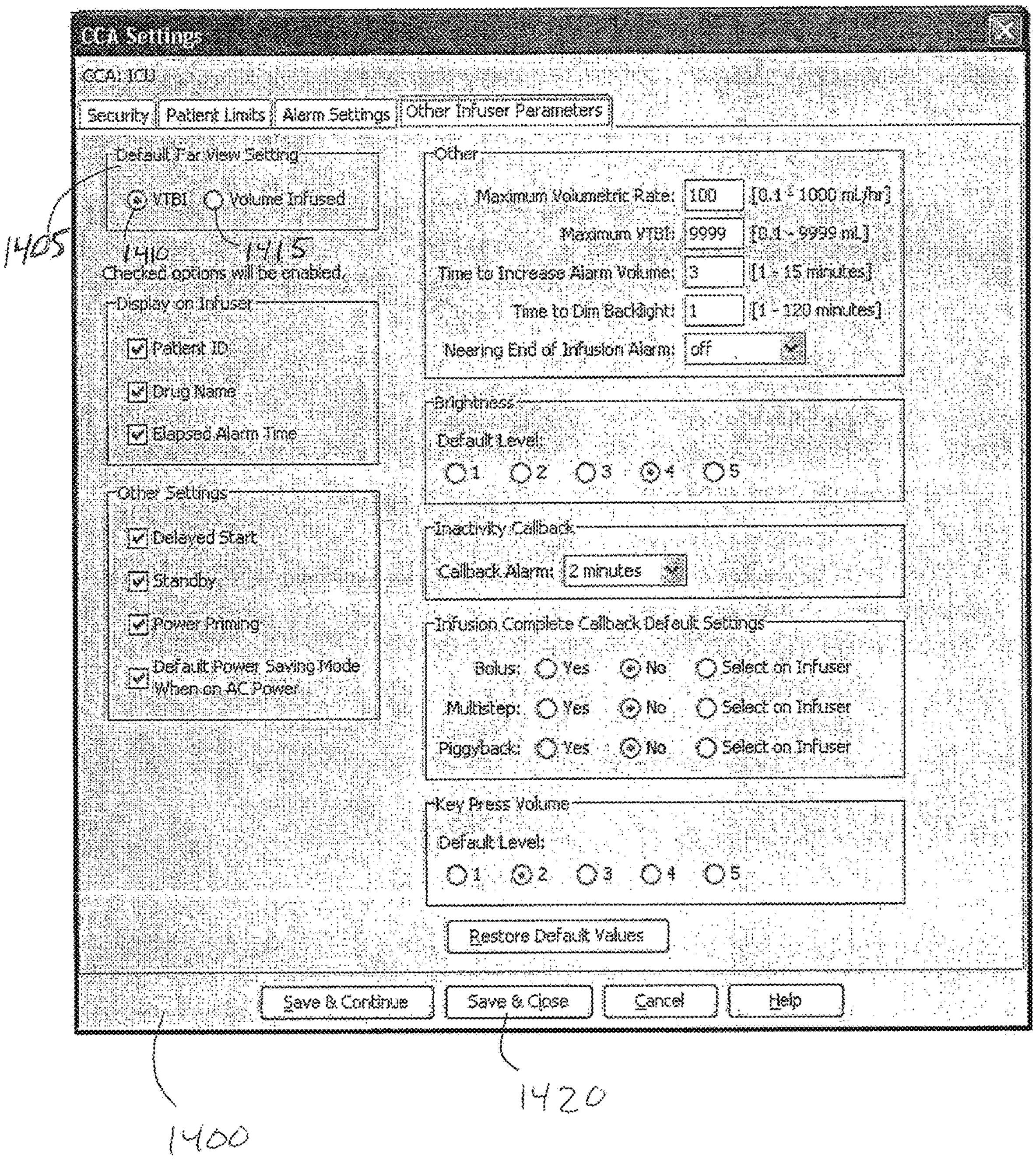
FIG. 14 is a screen shot of a graphical user interface for configuring a display setting at a drug library.
Figure 15A:
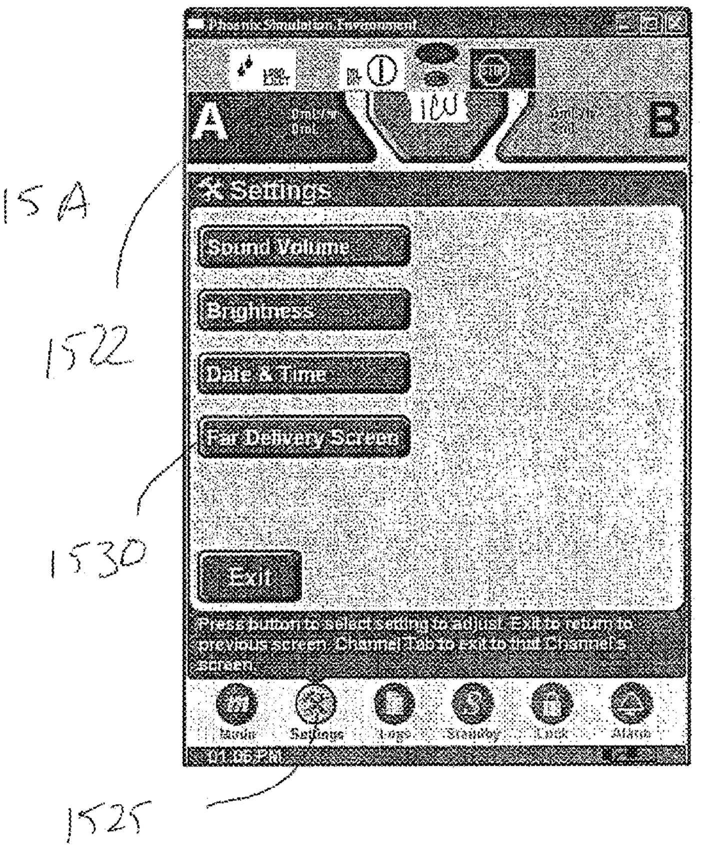
FIGS. 15A to 15C are screen shots illustrating a graphical user interface for configuring a medical device display parameter.
Figure 15B:
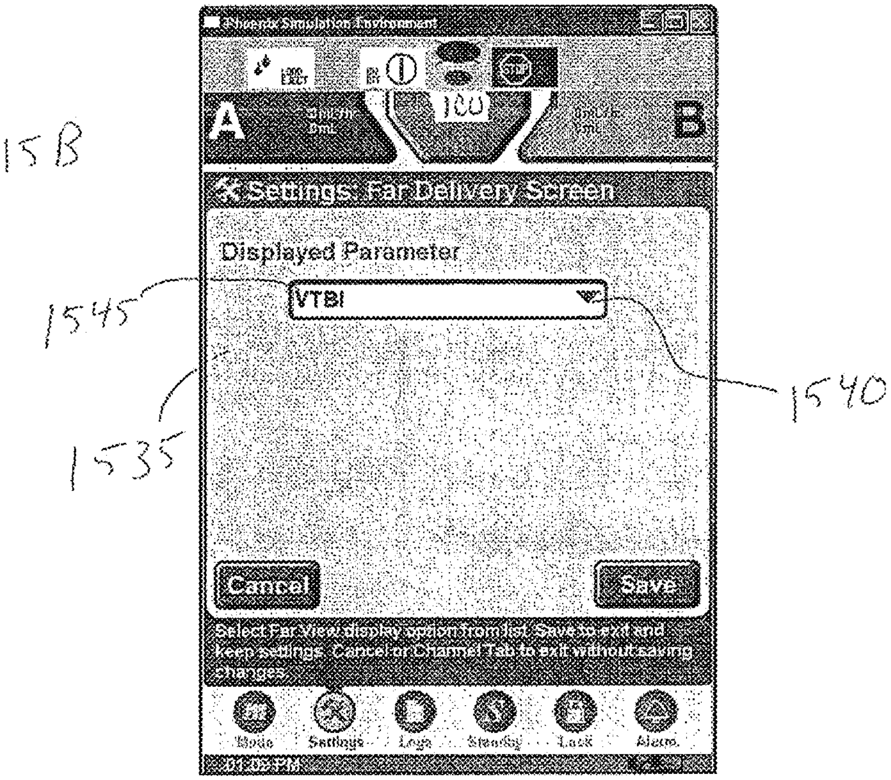
Figure 15C:
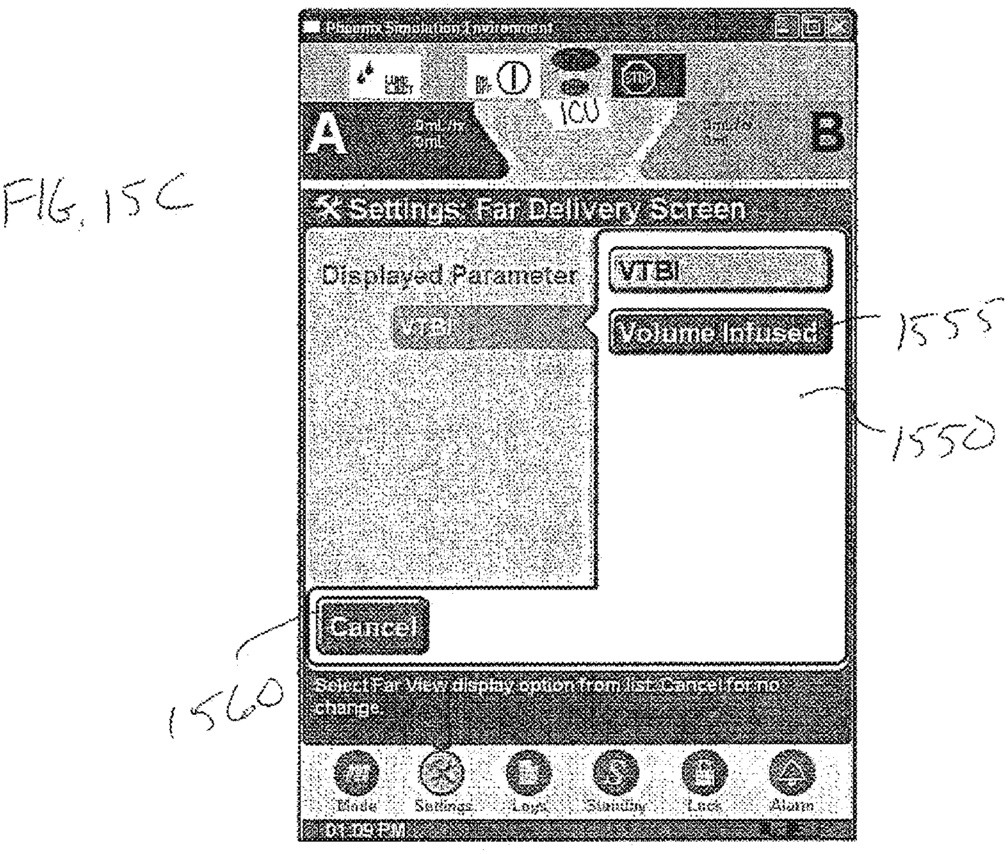
Figure 16:
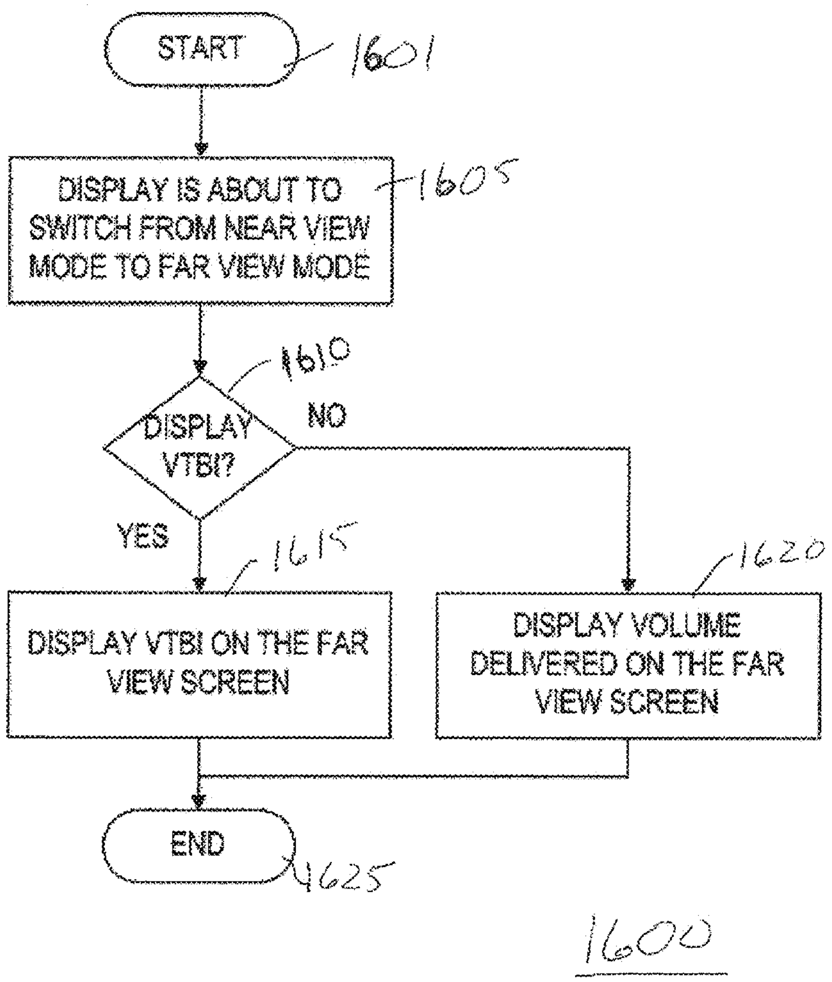
FIG. 16 is a flow chart for a program for determining a display parameter.

With reference to FIGS. 14 to 16, in another aspect, the drug library, located within the medication management system and downloaded to the medical device, can be configured to display either the VTBI or the volume infused as a default setting on the far view delivery screen. In another or the same embodiment, the user can change the default setting at the medical device, as provided in more detail below.

With reference to FIG. 14, illustrated is a screen shot of a graphical user interface 1400 for changing a plurality of settings of a drug library for a chosen CCA. In this example, the CCA is the Intensive Care Unit (ICU), though it should be understood that device settings for other CCAs may be similarly configured. The drug library includes drug and device related information, which may include but is not limited to drug name, drug class, drug concentration, drug amount, drug units, diluent amount, diluent units, dosing units, delivery dose or rate, medication parameters or limits, device/infuser settings and/or modes, CCA designations and constraints, and library version. Through the maintain drug library program 42 the drug library may be configured to provide a medical device 14 that includes a customized display. In one embodiment, the display is customized based on the Clinical Care Area (CCA) the medical device 14 is located in, assigned to, and/or to be assigned to.

Once the drug library graphical user interface 1400 for the chosen CCA is displayed, the administrator sets the "default far view setting" 1405 to either VTBI 1410 or volume infused 1415. FIG. 14 shows that VTBI 1410 has been selected as the default far view setting 1405.

With reference to FIGS. 15A to 15C, a user of a medical device having a default far view setting 1405 can change the default setting. To change the default far view setting 1405, the user presses settings button 1525 to access the settings screen 1522. Next, the user presses the far delivery screen button 1530 to access the settings far delivery screen interface 1535 illustrated in FIG. 15B. In this illustration, the default setting was set to display VTBI 1545. To change the default to display "volume infused" the user accesses pull down menu 1550 (FIG. 15C) by activating arrow 1540. Pressing the Volume Infused button 1555 will change the default setting to display the volume infused instead of the VTBI. The user can press the save button (FIG. 15B) or the cancel button 1560 (FIG. 15C) for no change to the default setting.

With reference to FIG. 16, illustrated is a flow chart of a program 1600 for determining at the medical device whether the VTBI should be displayed or the volume infused should be displayed, as described above. Program 1600 begins at block 1601 and proceeds to block 1605 where the display is about to switch from the near view to the far view. Prior to the switch program 1600 determines the display parameter based on the default far view setting 1405 from the drug library for the CCA chosen by the user or the most recent setting established by the user at the device. Based on the current display parameter setting, program 1600 determines at block 1610 whether to display the VTBI. If yes, program 1600 proceeds to 1615 to display VTBI on the far view screen. If no, program 1600 moves to block 1620 to display the volume delivered on the far view screen. Program 1600 ends at 1625. In another embodiment, the near view screen display parameter settings could be similarly configured and/or adjusted.

Figure 6A:
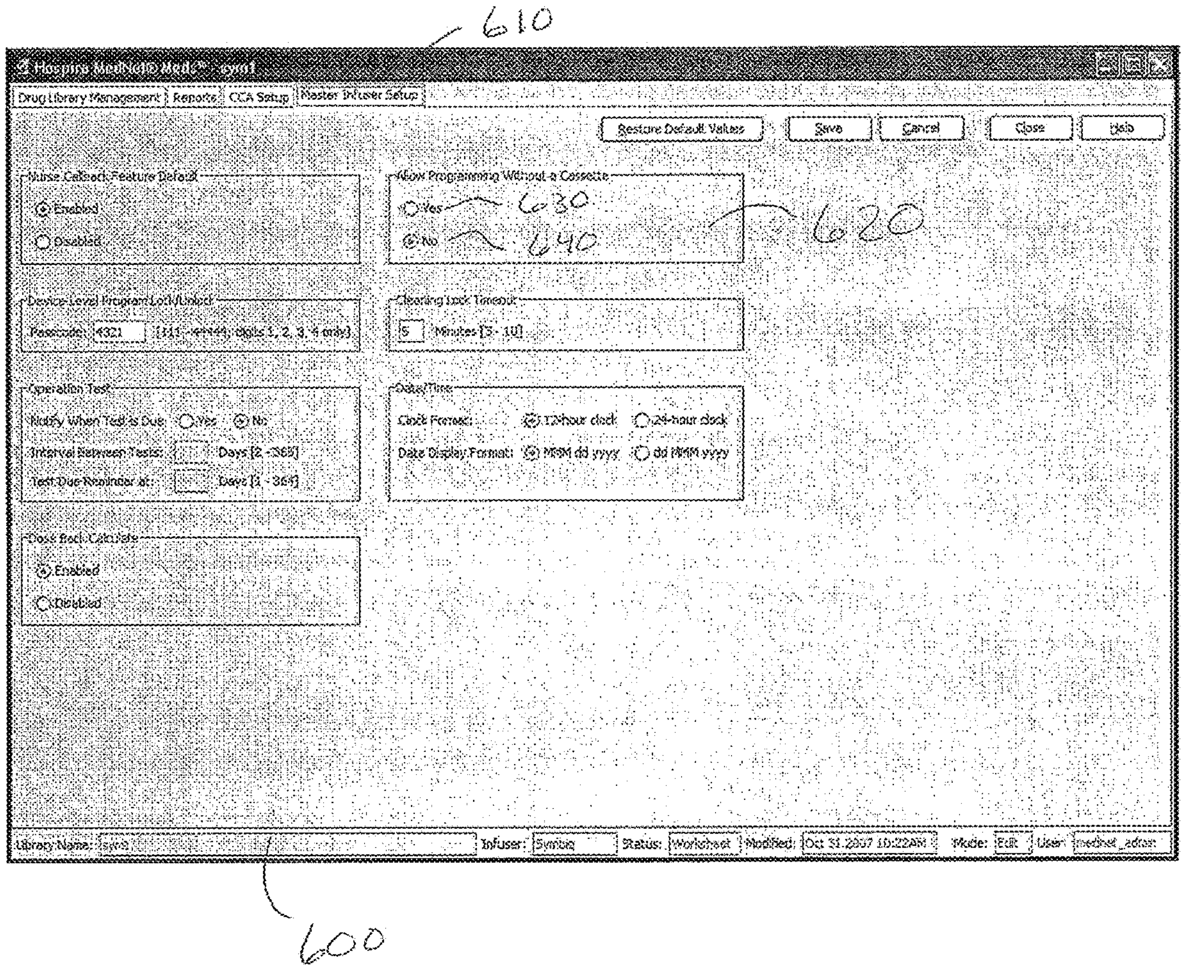
FIGS. 6A and 6B are screen shots of a graphical user interface for configuring a drug library parameter.
Figure 6B:
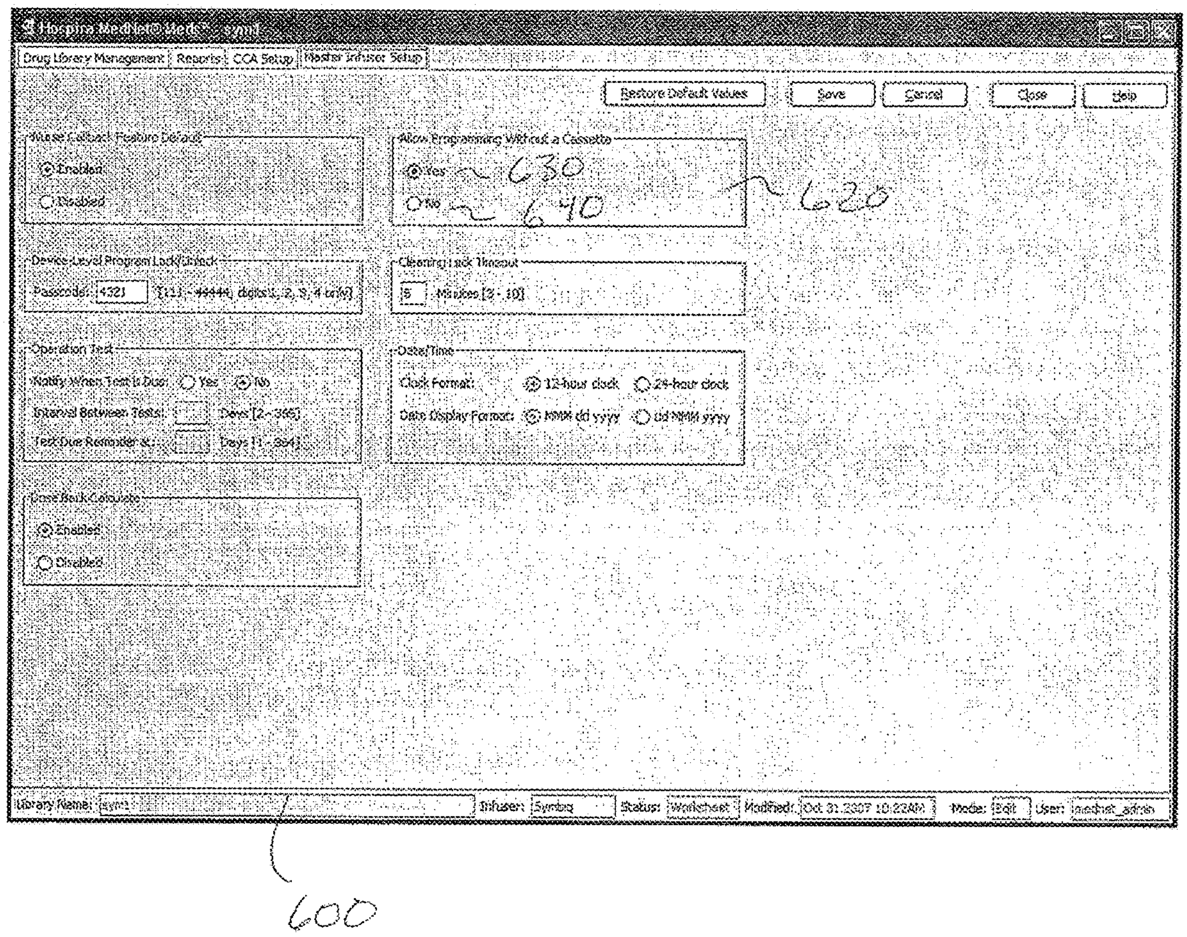

With reference to FIGS. 5, 6A and 6B, illustrated is graphical user interface 600 of an input device 38 within MMU 12 that is used to configure, within a medication management system all of the associated medical devices 14 as a part of the master infuser setup 610. Graphical user interface 600 is used by authorized personnel to configure medical device programming parameters. Infusion devices such as the pump 14 require an administration set to perform the infusion. In one embodiment, the administration set is a cassette. The below discussion is in relation to a cassette, however, other types of administration sets as known in the art may be used. Prior art devices require that the cassette be in place prior to programming the pump for an infusion. There are some circumstances within the hospital environment, however, where this requirement is inefficient and wasteful of expensive supplies that go unused, merely because the clinical caregiver has set up an infusion just in case it is needed in, for example, the OR, ER or the ICU. In other situations, the time it takes to program a pump only when it is needed may be harmful to the patient, especially in the OR and the emergency room. Conversely, disallowing the programming of a medical device without a cassette may enhance patient safety by, for example, reducing the risk of line confusion during setup.

Figure 7A:
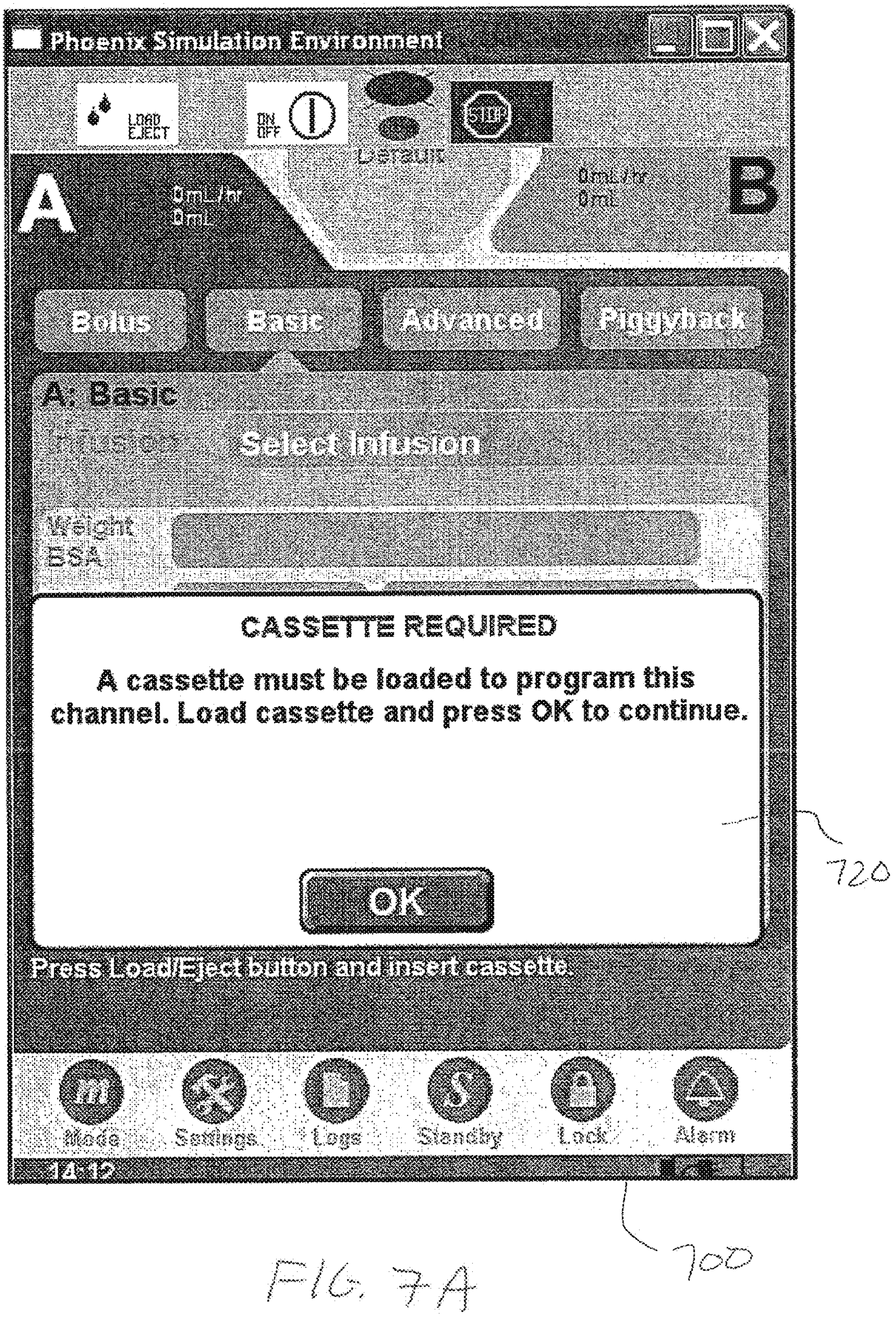
FIGS. 7A and 7B are screen shots of a graphical user interface for configuring medical device specific parameters.
Figure 7B:
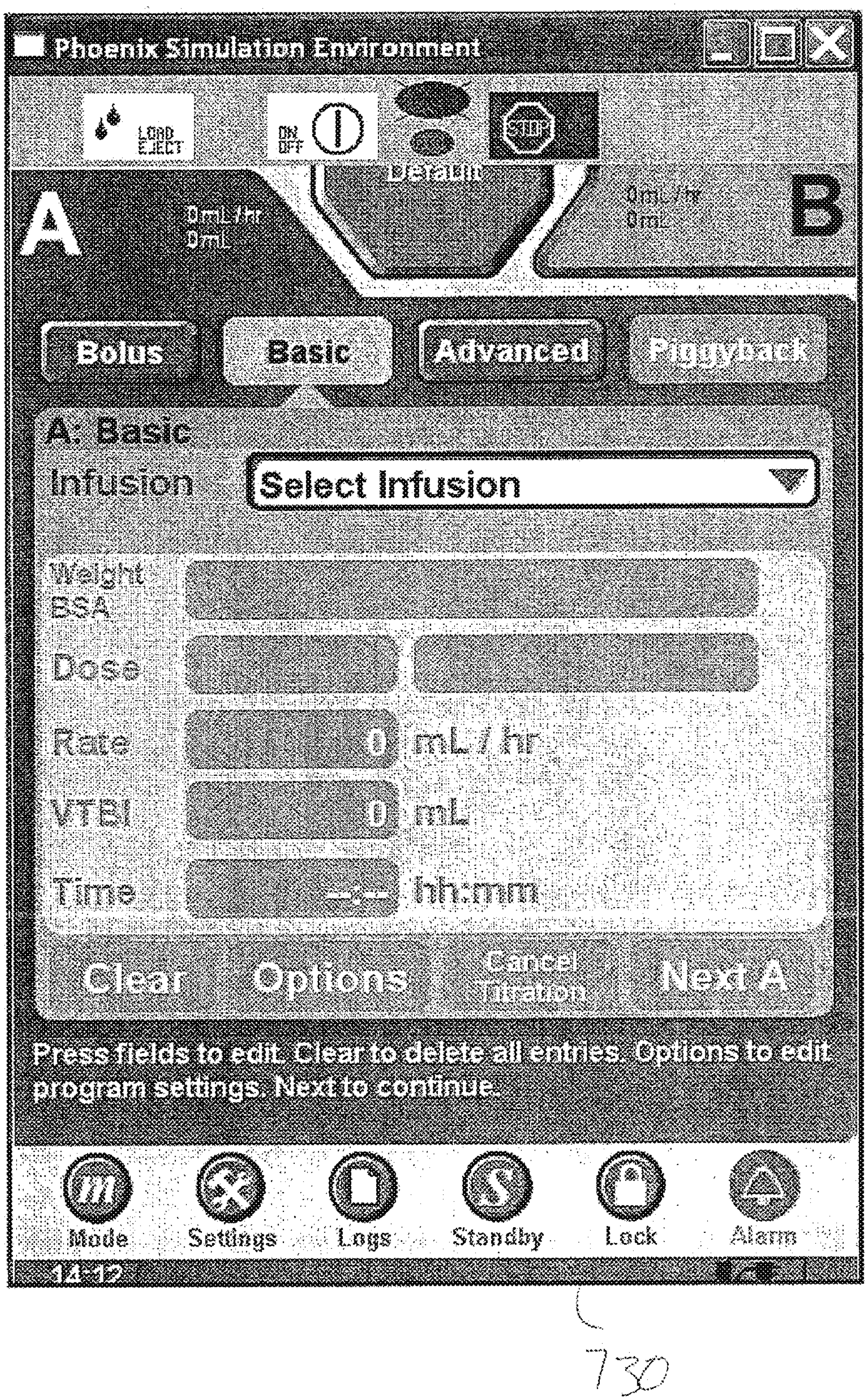

Therefore, in one aspect, the drug library, via the master infuser setup 610, can be configured by a hospital administrator based on hospital policy and procedure. FIGS. 6A and 6B illustrate the configurable parameter 620 of allowing programming of infusion pumps with or without a cassette in place. Thus, at graphical user interface 600, an administrator may choose to allow programming without a cassette by selecting "yes" 630 (FIG. 6B) or disallow programming without a cassette by selecting "no" 640 (FIG. 6A). FIG. 7 A illustrates a warning message 720 that appears on screen 700 when a user tries to program the medical device without a required cassette. Once the cassette is loaded, the programming can continue. FIG. 7B illustrates how a programming screen would appear if the programming was started with a cassette in place, whether or not required, or if programming was started without a cassette which has been allowed by the configuration of the master infuser setup 610.

Figure 8:
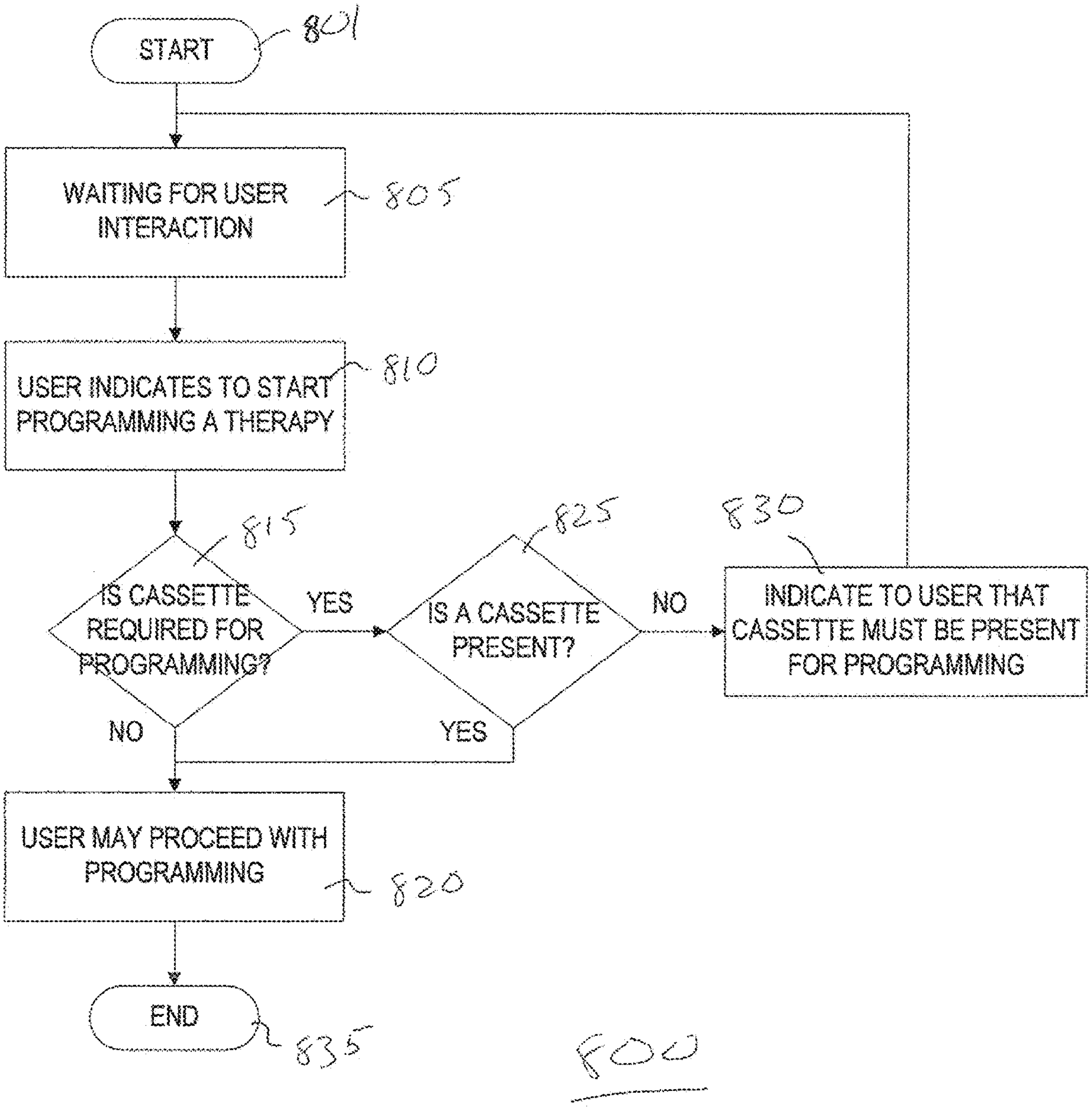
FIG. 8 is a flow chart for a program for allowing or disallowing programming of a medical device in regards to the presence of a cassette.

With reference to FIG. 8, a flow chart of a program 800 for determining at the medical device whether the drug library within the memory of the medical device allows the medical device to be programmed with or without a cassette in place. Program 800 begins at 801 and proceeds to 805 where upon some user interaction (e.g. power on), program 800 proceeds to block 810 where the program 800 receives an indication that the user is starting to program a therapy. Upon receiving the indication, program 800 determines at block 815 whether a cassette is required for programming. If no, the program allows the user to proceed, block 820 and the program ends at block 835. However, if at block 815 it is determined that a cassette is required, program 800 determines at block 825 whether a cassette is in place. If yes, program 800 proceeds to block 820 to allow the user to continue and the program ends at 835. If, at block 825, program 800 determines that a cassette is not present, a warning message 720 is displayed that indicates to the user that a cassette is required. The user may either place a cassette as required and continue or discontinue the attempted programming.

Another aspect allows the user to modify the CCA without the interruption of a current infusion. FIGS. 9A to 11 illustrate various embodiments of allowing the user to modify the CCA "on the fly." The ability to change the CCA is this manner increases user and workflow efficiency. In particular, the ability to change the CCA while an infusion is running is crucial where a patient is being transported from one CCA to another such as from the emergency room (ER) to the OR, or from the OR to the ICU. This ability to change the CCA also enhances patient safety where time to wait for an infusion to end may be harmful to the patient. FIGS. 9A to 9G illustrate a series of screen shots of a medical device configured to allow the CCA to be changed while an infusion is ongoing on another channel of the multi-channel pump.

Figure 9A:
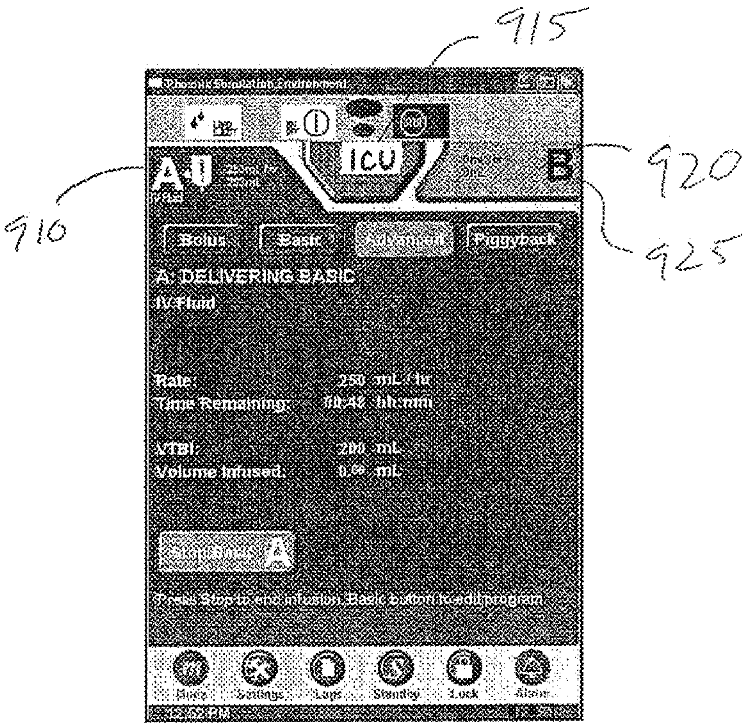
FIGS. 9A to 9G are screen shots of a graphical user interface, illustrating changing a clinical care area.
Figure 9B:
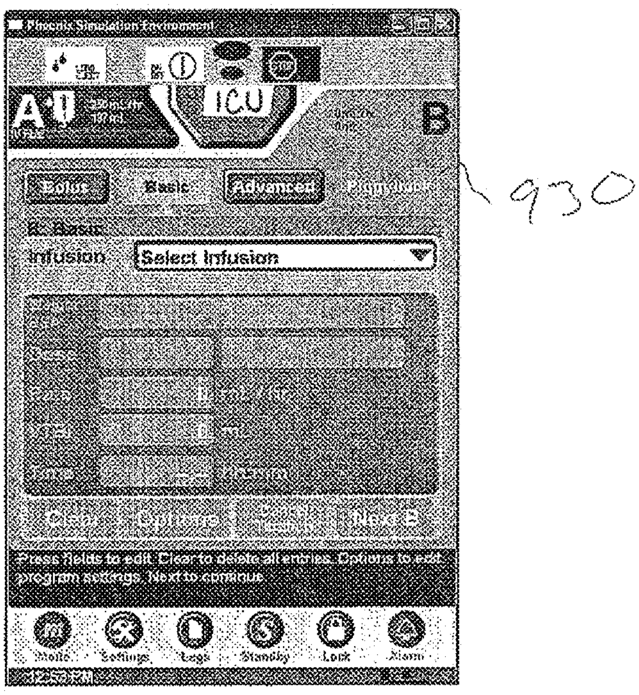
Figure 9C:
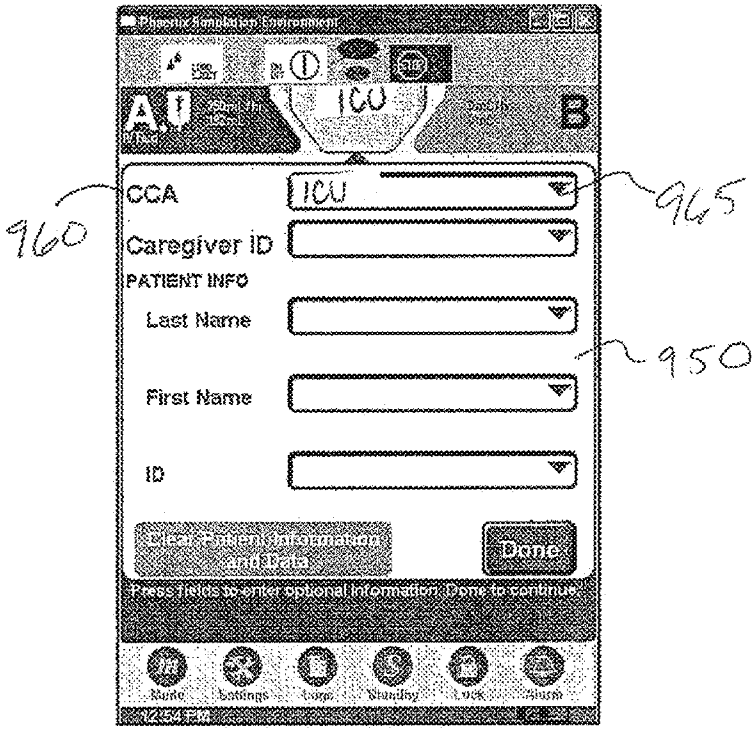
Figure 9D:
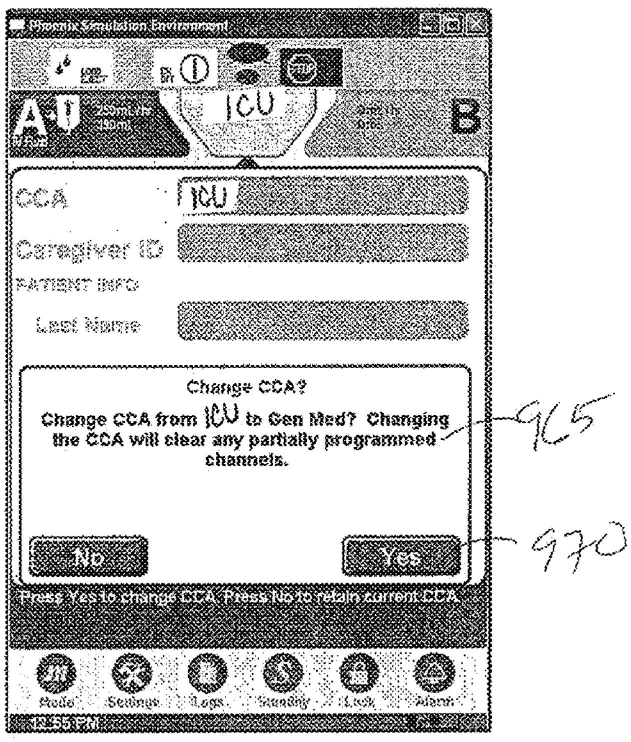
Figure 9E:
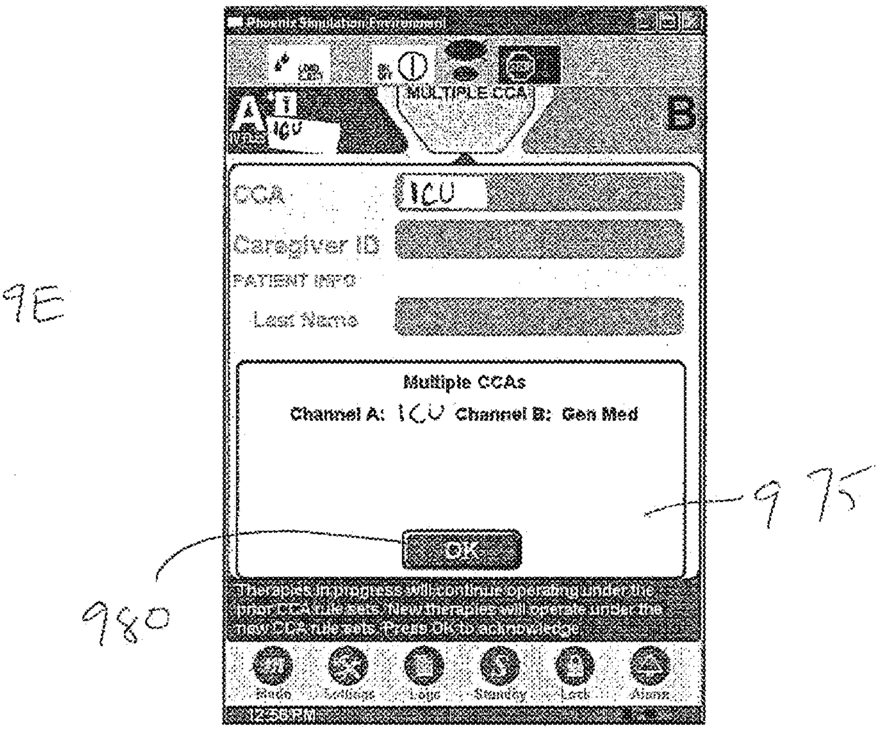
Figure 9F:
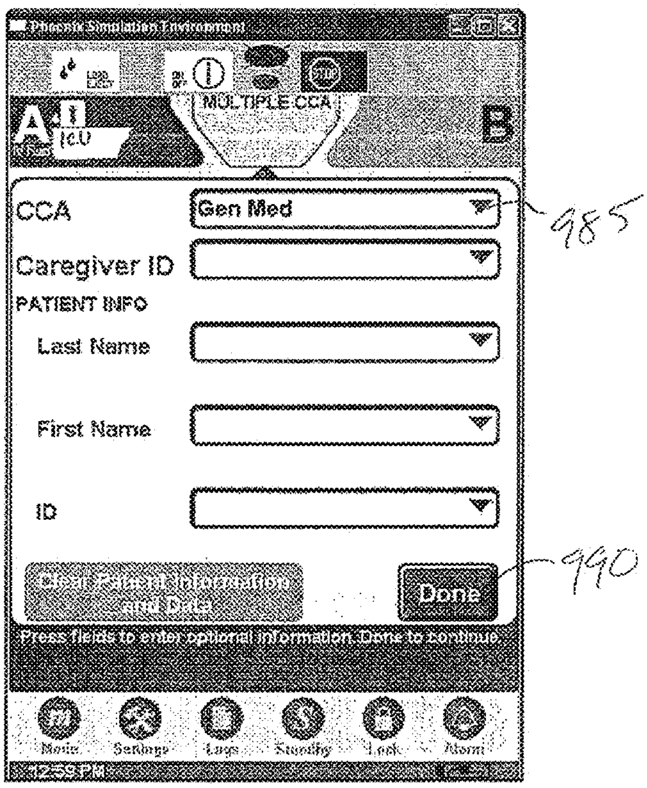
Figure 9G:
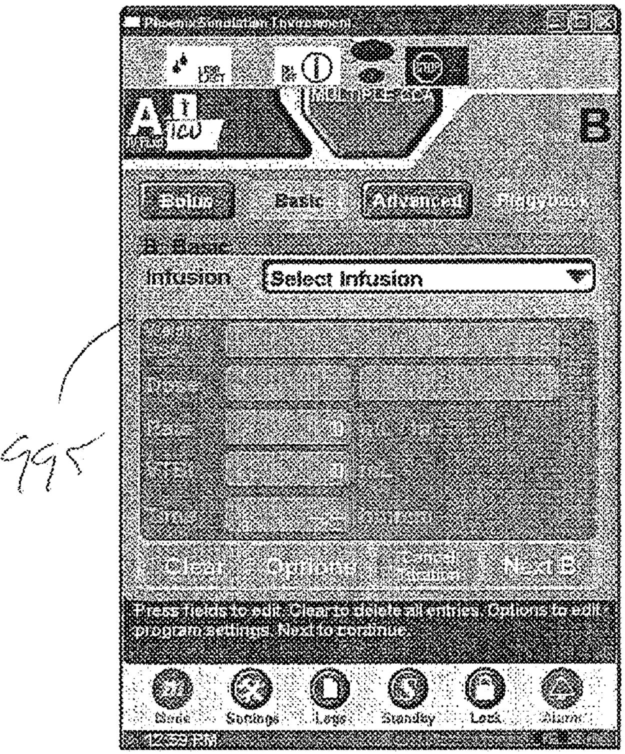

FIG. 9A illustrates that a therapy is delivering on channel A 910 with the ICU CCA 915. In this example, a user wants to change the CCA and program Channel B 920. The user selects channel B by pressing tab B 925, which brings up the channel B programming display screen 930 shown in FIG. 9B. Moving from FIG. 9B to FIG. 9C, the patient information button 940 has been pressed. Pressing the patient information button displays a patient information data field 950 for entry of patient data and changing the CCA 960. When the user presses the CCA button, a "Change CCA" message 965 appears requesting that the user confirm that the CCA is to be changed (FIG. 9D). In this example, the user wants to change the CCA from ICU to Gen Med. To confirm, the user presses the "yes" button 970. In response to the confirmation, a "multiple CCAs" system message 975 appears. To confirm, the user presses the "OK" button 980. Once the OK button 980 has been pressed, the CCA has been changed at 985 and a "Done" button 990 is displayed to continue with the programming of the infusion at infusion screen 995 (FIG. 9G).

Figure 10:
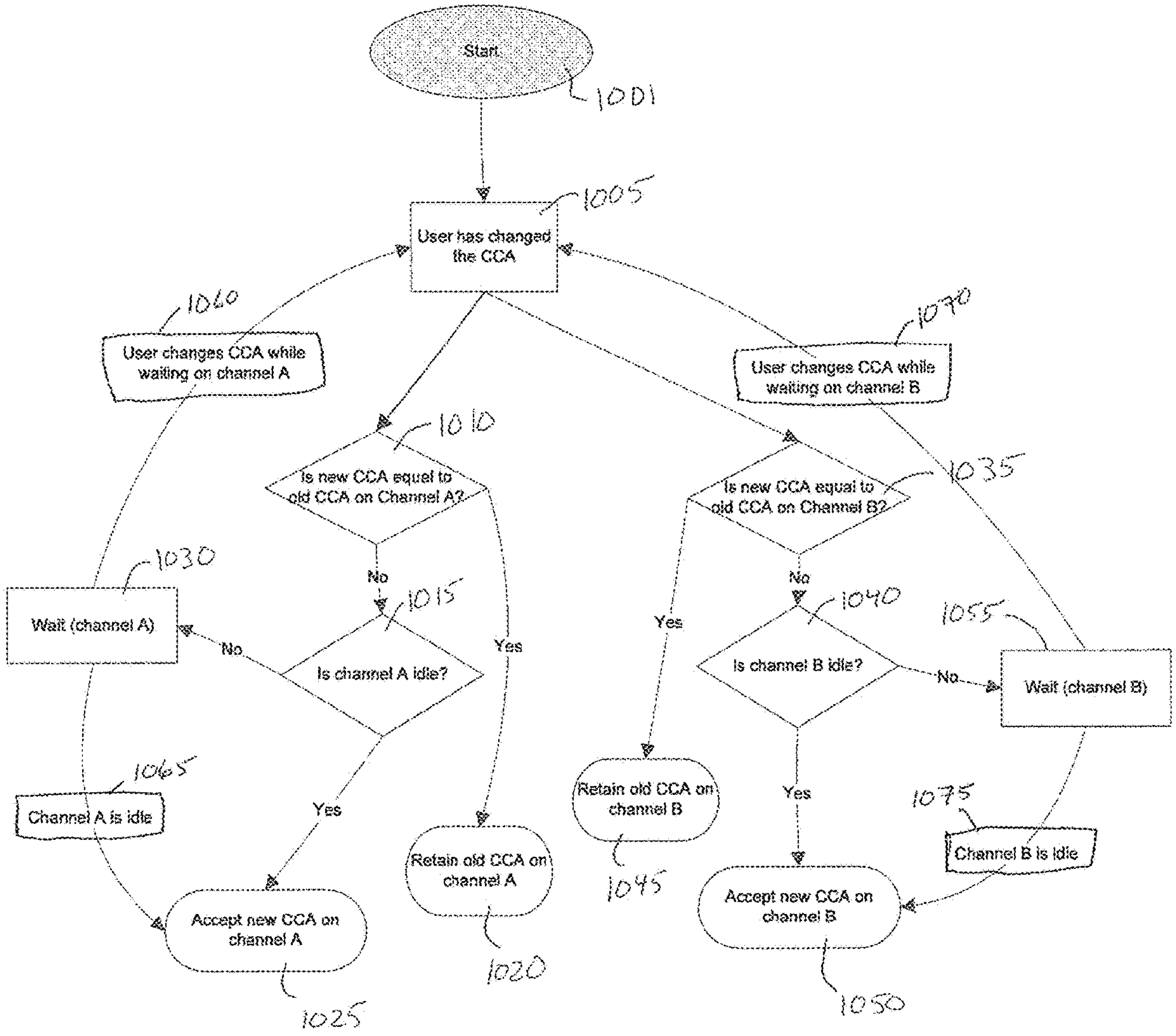
FIG. 10 is a flow chart for a program for changing a clinical care area in a multi-channel infusion pump.

With reference to FIG. 10, illustrated is a program 1000 for changing the CCA at a multi-channel medical device 14. Program 1000 starts at 1001 and proceeds to block 1005 where it is determined that the user has changed the CCA. Program 1000 then determines at block 1010 whether the new CCA is the same as the old CCA for Channel A If yes, the program proceeds to block 1020 to retain the old CCA on Channel A If no, program 1000 proceeds to block 1015 to determine whether channel A is idle. If yes, program accepts the new CCA on channel A at block 1025. If no, channel A is set to wait at block 1030 until either 1) the user changes the CCA while waiting on channel A (block 1060), whereby program 1000 proceeds to 1005; or 2) channel A becomes idle (block 1065), whereby program 1000 proceeds to block 1025 and accepts the new CCA on channel A Additionally, when a user has changed a CCA (block 1005), channel B is evaluated. Program 1000 proceeds from block 1005 to block 1035 to determined whether the new CCA is the same as the old CCA for Channel B. If yes, the program proceeds to block 1045 to retain the old CCA on Channel B. If no, program 1000 proceeds to block 1040 to determine whether channel B is idle. If yes, program 1000 accepts new CCA on channel B, block 1050. If no, channel B is set to wait at block 1055 until either 1) the user changes the CCA while waiting for channel B (block 1070), whereby program 1000 proceeds to 1005; or 2) channel B becomes idle (block 1075), whereby program 1000 proceeds to block 1050 and accepts the new CCA on channel B.

Figure 11:
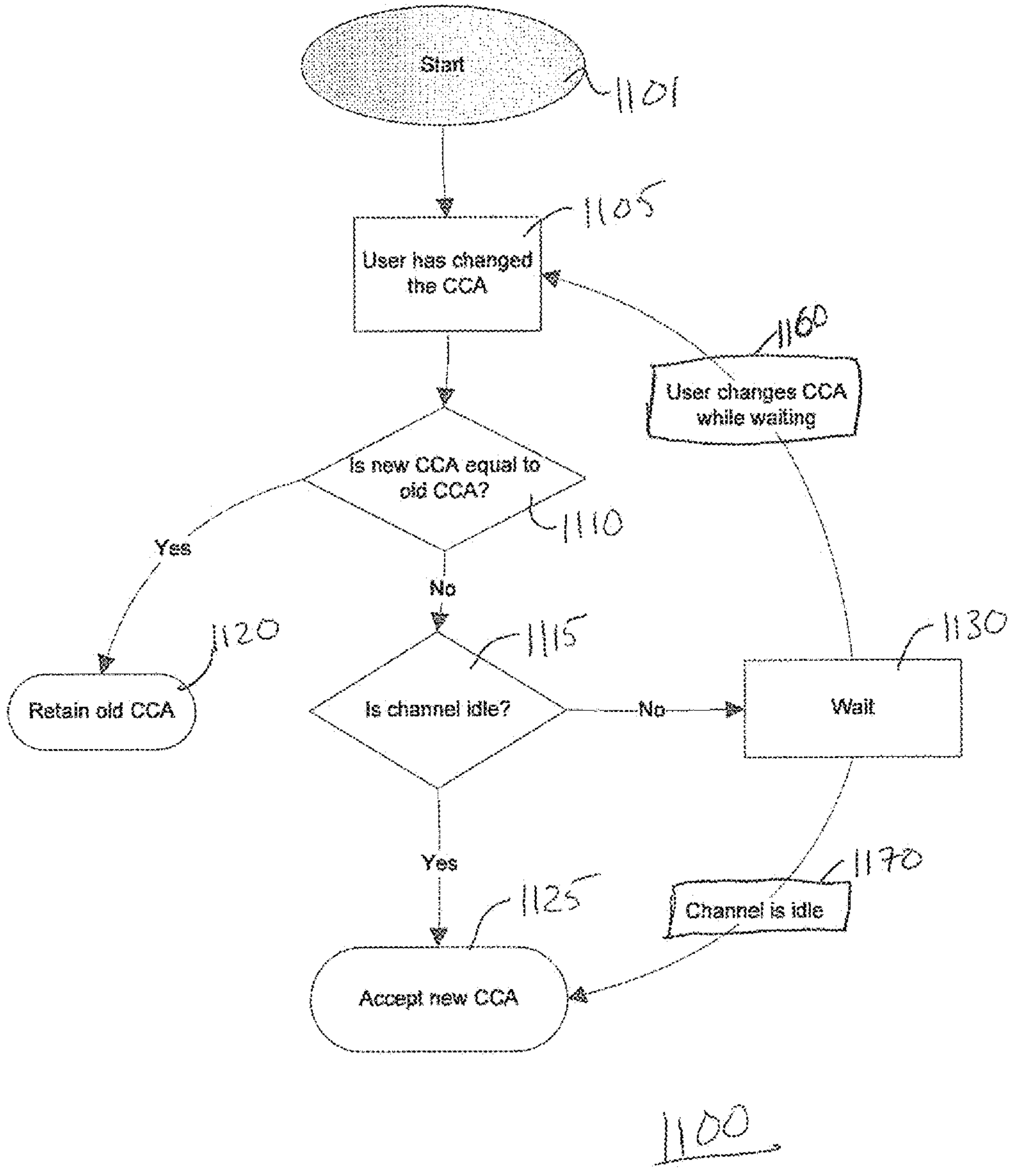
FIG. 11 is a flow chart for a program for changing a clinical care area in a single channel infusion pump.

With reference to FIG. 11, illustrated is a program 1100 for changing the CCA at a single channel medical device. Program 1100 starts at 1101 and proceeds to block 1105 where it is determined that the user has changed the CCA. Program 1100 then determined at block 1110 whether the new CCA is the same as the old CCA. If yes, the program proceeds to block 1120 to retain the old CCA. If no, program 1100 proceeds to block 1115 to determine whether the channel is idle. If yes, program 1100 accepts the new CCA, block 1125. If no, the channel is set to wait at block 1130 until either 1) the user changes the CCA while waiting (block 1160), whereby program 1100 proceeds to 1105; or 2) the channel becomes idle (block 1170), whereby program 1100 proceeds to block 1125 and accepts the new CCA.

Figure 12A:
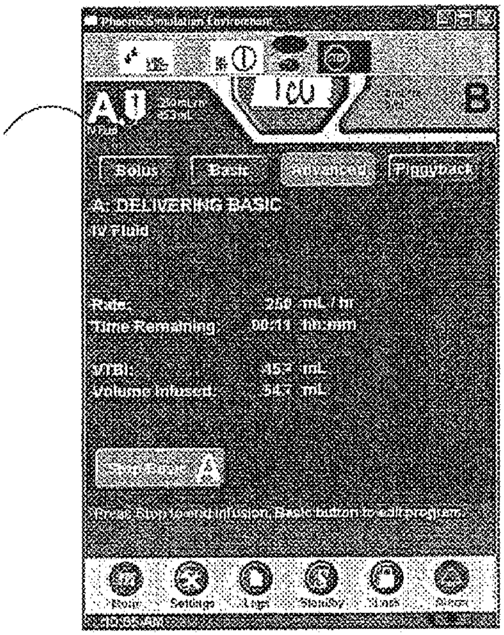
FIGS. 12A to 12F are screen shots of a graphical user interface, illustrating programming of additional VTBI to current infusion.
Figure 12B:
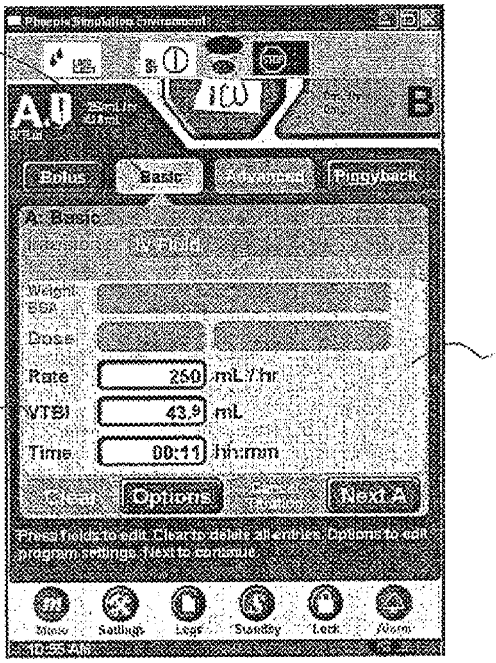
Figure 12C:
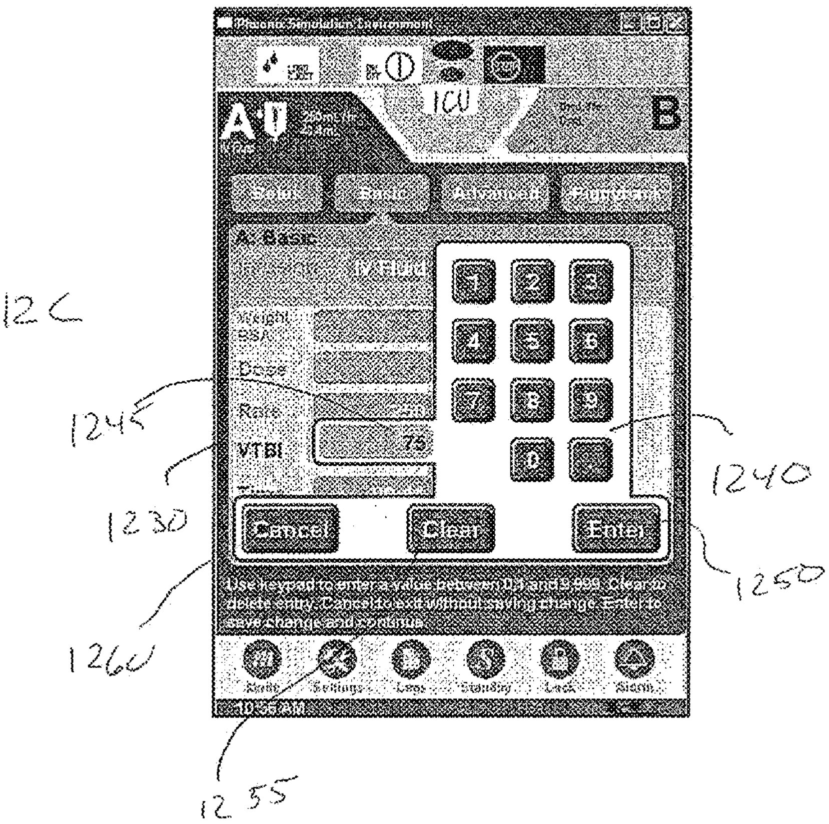
Figure 12D:
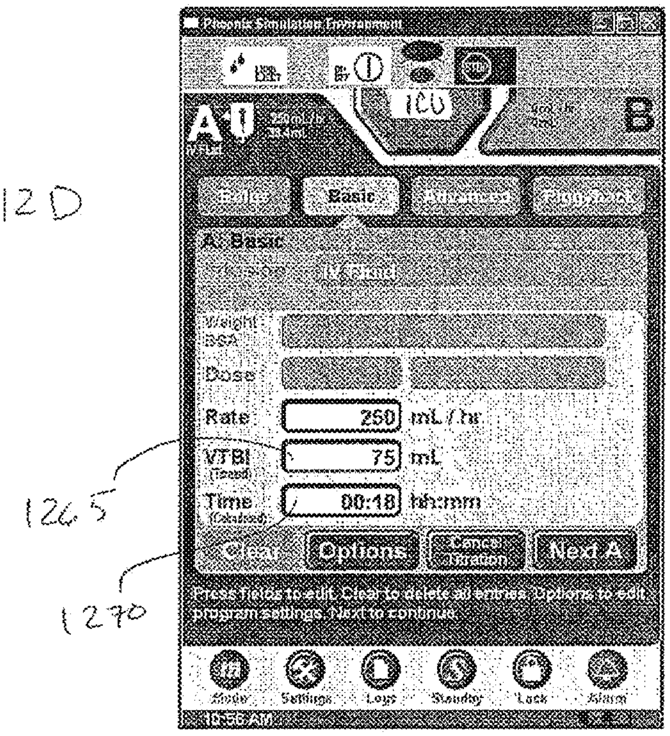
Figure 12E:
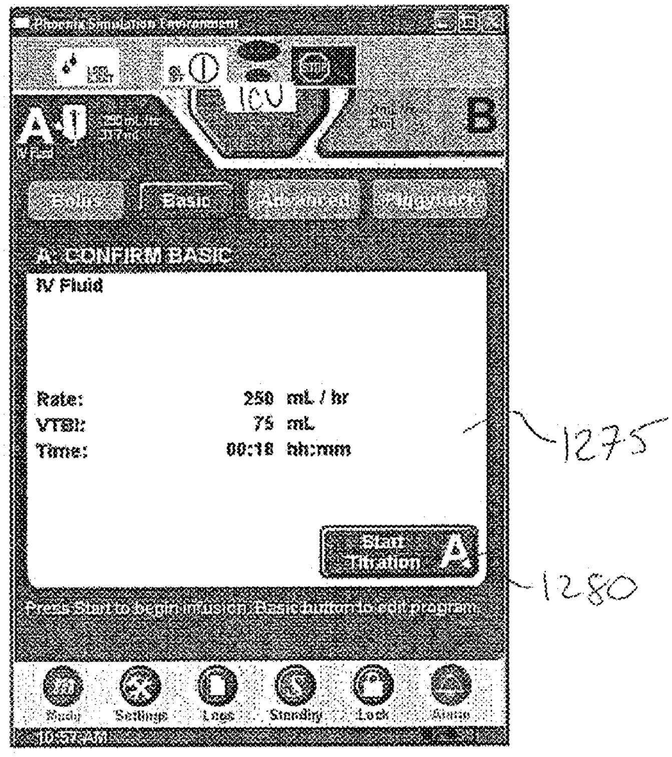
Figure 12F:
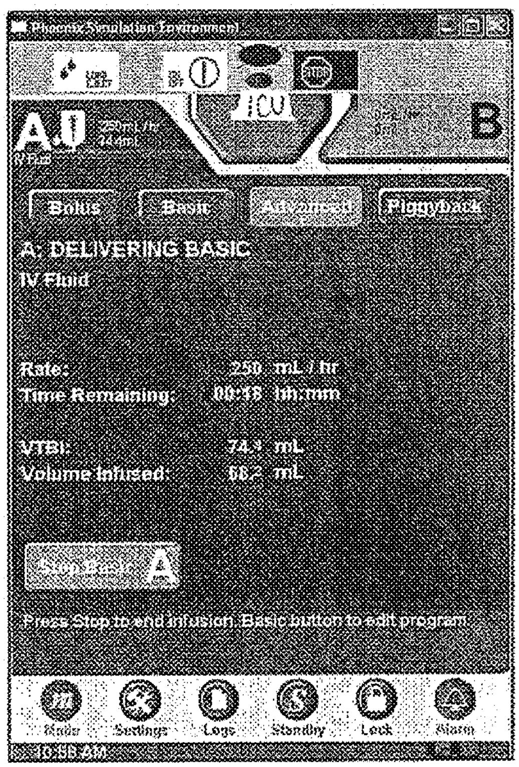
Figure 13:
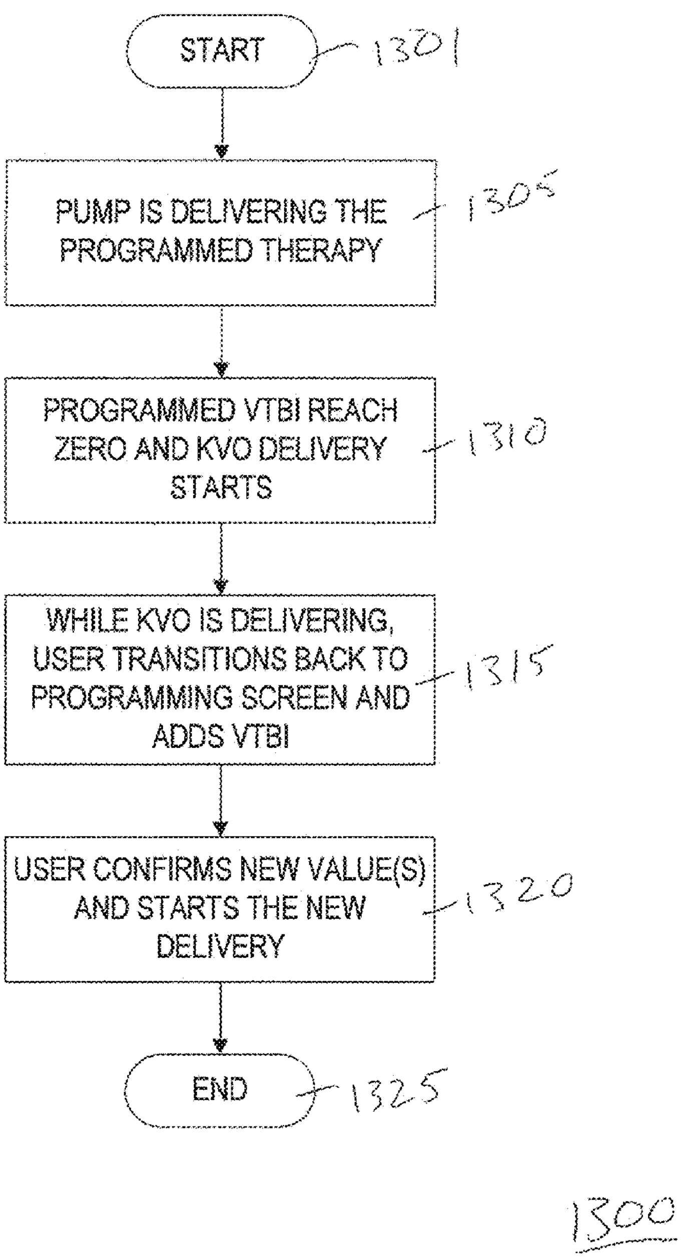
FIG. 13 is a flow chart for a program for adding additional VTBI to a current infusion.

With reference to FIGS. 12A to 13, illustrated is another aspect that allows a medical device 14 user to modify the VTBI parameter to specify additional fluid when an infusion is nearing completion or is delivering in a KVO (keep vein open) mode. A configured medical device that includes a program to allow the additional fluid provides for more efficient workflow as well as a more efficient user. In one embodiment of the invention, the program for allowing additional VTBI maintains all other delivery parameters while allowing the user to specify the additional VTBI. Thus, the user does not have to re-enter common delivery parameters when only an additional VTBI is needed. This reduces programming effort, saves time and reduces the potential for errors.

FIG. 12 A to 12F illustrate, using a series of screen shots, one embodiment of a program for modifying the VTBI delivery parameter. At FIG. 12A, a basic infusion is delivering on channel A, as shown by screen display 1200. At this point in the infusion, FIG. 12A shows that the remaining VTBI is 45.3 ml. FIG. 12B illustrates that the user has pressed "basic" button 1210. A data entry field 1220 appears based on the pressing of the basic button 1210. At data entry field 1220, the user can press the particular field to edit. FIG. 12C illustrates that the user pressed the VTBI button 1230 to edit the VTBI. In response to pressing the VTBI button 1230 a keypad 1240 appears on the display screen. Here, the user enters the total amount of VTBI desired. In this exam pie, the user enters 7 5 via the keypad 1240 into the data field for VTBI 1245. The user then presses "Enter" 1250 to save the changes and continue. Alternatively, the user can press "Clear" 1255 to delete the entry or cancel 1260 to exit without saving the changes. FIG. 12D illustrates that the VTBI has been changed to 75 ml and entered. FIG. 12D also illustrates that the time remaining has been recalculated and is displayed in area 1270 based on the new VTBI displayed in area 1265. At FIG. 12E, a confirmation of titration screen 1275 has appeared to confirm the new VTBI. The user confirms the change to the VTBI by pressing "Start Titration" button 1280. FIG. 12F illustrates that the infusion has been updated with the new VTBI and is continuing to run. In one embodiment, the method illustrated in FIGS. 12A to 12F is used to add to the VTBI the fluid remaining in the fluid container that is currently infusing. In another embodiment, the user may add a new container of fluid as long as all other delivery parameters remain the same as the currently running infusion.

FIG. 13 is a flow diagram illustrating one embodiment of a method 1300 for adding additional VTBI to a current infusion. Method 1300 starts at block 1301 and proceeds to block 1305 where it is determined that the pump is delivering a programmed therapy. Method 1300 continues at block 1310 where the programmed VTBI reached zero and the KVO delivery starts. At block 1315, a user accesses a VTBI programming screen 1220 and enters a VTBI value 1245. The user confirms the new value at block 1320 and starts the new delivery. Method 1300 ends at 1325. One skilled in the art will appreciate from the disclosure herein that such adding of VTBI can also be adapted for use in bolus or piggyback situations.

Figure 21A:
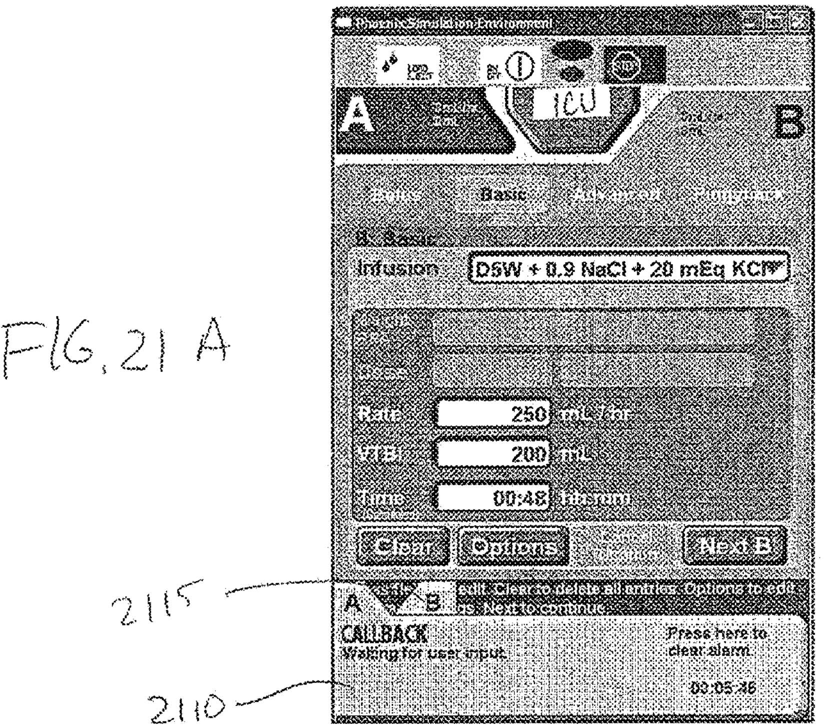
FIGS. 21A and 21 B are screen shots of various graphical user interface call back alarms.
Figure 21B:
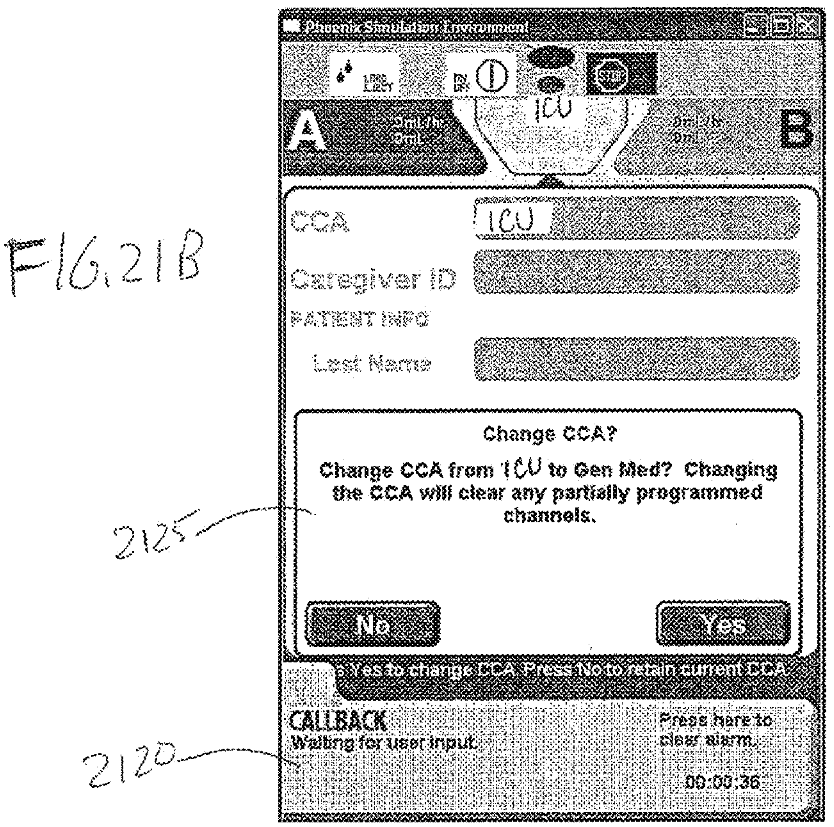
Figure 22:
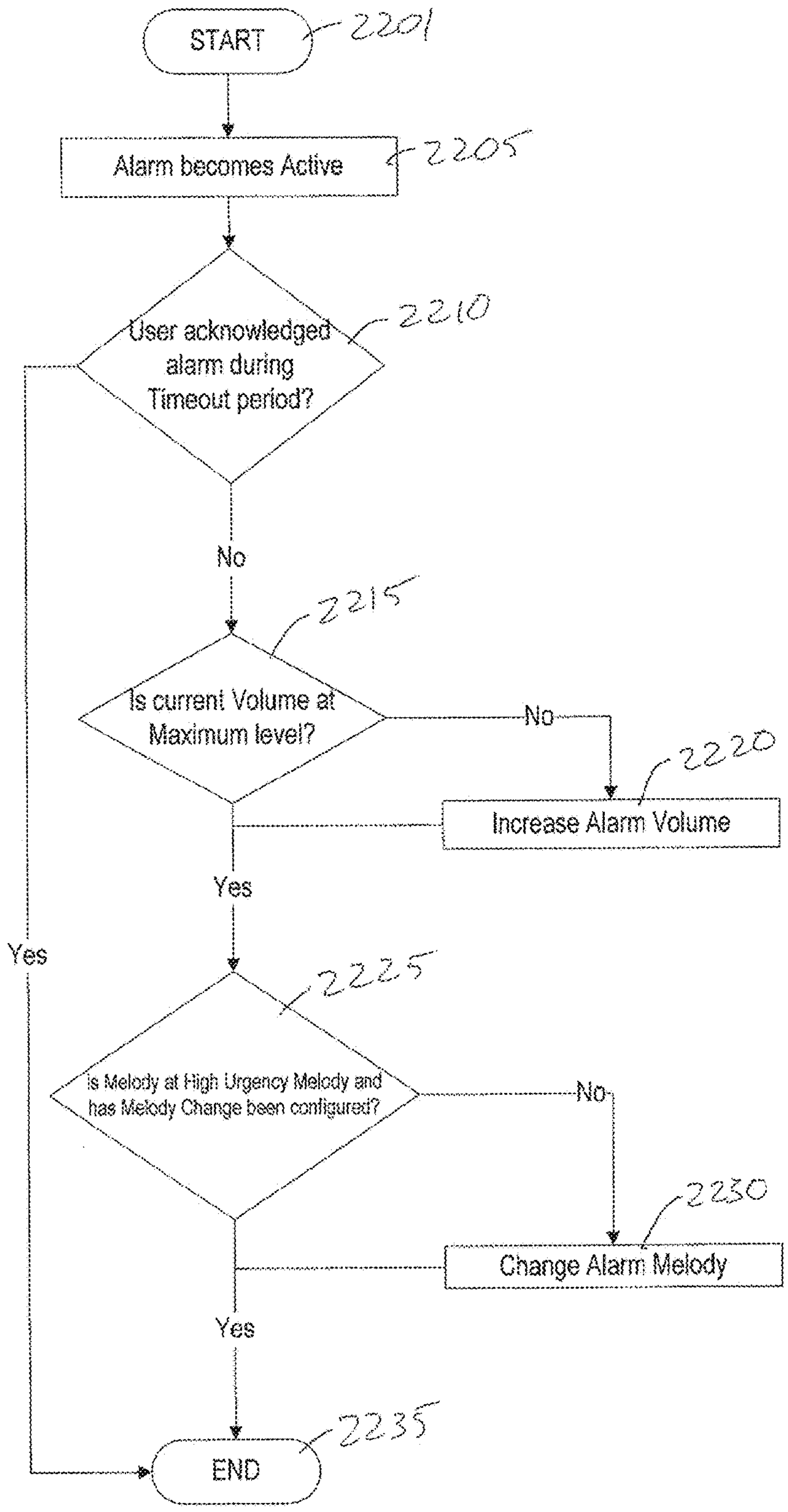
FIG. 22 is a flow chart for a program for responding to various call back alarms.

With reference to FIGS. 21A to 22, one embodiment provides for improved callback rules for the medical device. Medical devices generally have three classes of callback alarms based on urgency: High Urgency (e.g. Air-In-Line); Medium Urgency (e.g. Inactivity callback); and Low Urgency (e.g. Battery not Charging). In one embodiment of the invention, the alarms are configured at the drug library. In one embodiment, the alarms are configured at the drug library based on the CCA in which the medical device resides. In another embodiment, the alarms are configured at the drug library master infuser settings so that the alarm configurations apply to all medical devices within the medication management system. In other embodiments, the alarms are configurable by the clinician at the medical device. For example, in one embodiment, default alarm settings were configured at the drug library, and sent to the medical device where, depending on the alarm configuration rules set by the hospital administration, a clinician may modify the alarm based on factors such as the particular CCA, or personal preference.

In one embodiment of the invention, a specific alarm type or configuration is assigned to each class of urgency such that a clinician can determine the urgency of the callback alarm upon hearing the alarm. In one embodiment of the invention, each class of alarm is assigned a different melody, a different tone or series of tones and/or a different volume. In other embodiments, the frequency of the alarm is configured based on the class of alarm. In other embodiments, the volume, melody, tone and/or frequency may escalate based on a non-response by the clinician.

In one embodiment of the invention, when an audible alarm occurs at the medical device, the audio volume starts at the volume setting configured at the drug library and or by the clinician. However, if the alarm is not acknowledged, the volume is automatically escalated to a predetermined volume after a predetermined time out period passes. In one embodiment, the time out period is configurable at the drug library. In another embodiment, the time out period is configurable at the drug library for each particular CCA. In yet another embodiment, the time out period is configurable at the medical device. In another embodiment, a default value for the time out period is set at the drug library and may be changed at the medical device to a value that does not exceed the default value. For example, if the default time out period is 20 seconds, the user may set the time out period to less than 20 seconds such as for 10 seconds. In on embodiment of the invention, the volume escalates for only those alarms in the High Urgency class of alarms. In other embodiments, the volume escalates for both High Urgency and Medium Urgency classes of alarms.

In another embodiment, the alarm tone escalates after a predetermined time out period if the alarm is not acted upon. In this embodiment, a default tone set at the drug library may be configurable by a user at the medical device. In one embodiment, the pitch of the tone becomes higher when the alarm escalates due to the non-response of the clinician.

In another embodiment, the alarm comprises a predetermined tone melody. In one embodiment, a different tone melody is chosen for each class of alarm urgency or priority. In one embodiment, the High Urgency audible alarm is a sequence of six or seven tones that continually repeat until the alarm is acted upon by the clinician. In one embodiment, a brief pause of the tone sequence (melody) occurs between each repeat of the sequence. In one embodiment, the melody for the High Urgency alarm also escalates in volume with continued inactivity by the clinician. In one embodiment, the volume of the melody escalates after a predetermined length of time. In one embodiment, the escalation of volume is configured at the drug library. In another embodiment, the volume escalation is set as a default in the drug library and is further configurable at the medical device by the clinician.

In another or the same embodiment, the Medium Urgency audible alarm is a sequence of three tones. In one embodiment, the tone sequence (melody) repeats after a predetermined length of time if the clinician has not responded to the alarm. In one embodiment the predetermined length of time is 1 to 2 minutes. In another embodiment, the predetermined length of time is from 1 to 60 seconds. In one embodiment, the predetermined length of time is configured at the drug library. In another embodiment, the predetermined length of time is set as a default at the drug library and is further configurable by the clinician at the medical device.

In another embodiment, the Low Urgency audible alarm is a sequence of two tones. In one embodiment, the tone sequence repeats every two to ten minutes until acted upon by the clinician. The time to repeat may be configured as above for the Medium Urgency alarm.

In one embodiment, the High Urgency alarms are configured to have a melody with a very fast paced tempo. While the lesser urgency alarms have a melody with a slower paced tempo. In one embodiment, an alarm comprising a melody escalates in tempo when the alarm is not responded to by the user. In one embodiment, the alarm is configurable by the user at the medical device to a melody of the user's choice. In an example, a melody may be assigned to each user whereby the user sets the alarm on each medical device the user is responsible for to that one melody. In this manner, any one user in a location with multiple users can identify by sound that the alarm is for a medical device of a patient under their specific care.

FIG. 21A illustrates a screen shot of a medical device showing that a channel level callback alarm 2110, 2115 has sounded for each channel A and B where a therapy was partially programmed and no other action was taken by the user. FIG. 21 B illustrates a device level callback alarm 2120 has appeared because no keypress was made while a popup 2125 was displaying.

With regard to FIG. 22, a flow chart of a program 2200 for escalating an audible callback alarm. Program 2200 begins at 2201 and proceeds to block 2205 where an alarm has been activated. At block 2210, program 2200 determines whether the clinician has acknowledged the alarm during a timeout period. If yes, program 2200 proceeds to end at 2235. If no, program 2200 proceeds to block 2215 where a determination is made as to whether the current volume is at a maximum level. If no, program proceeds to block 2220 where the program increases the alarm volume. If yes at block 2215, program 2200 proceeds to block 2225 to determine whether the melody is at a High Urgency and has a melody change been configured. If yes, program 2200 proceeds to end at 2235. If no at block 2225, program 2200 proceeds to block 2230 to change the melody. Program 2200 then proceeds to end at block 2235.

When an alarm occurs on a medical device it may apply to the entire device (e.g. low battery) or it may only apply to a specific channel (e.g. inactivity callback on channel A). If the alarm is channel specific, the user needs to navigate to the channel to view what is causing the callback. In another aspect, a device program automatically takes the user to the precise location of the alarm when the user touches the alarm display area on the display screen as will be described below with reference to FIGS. 23A to 23C.

Figure 23A:
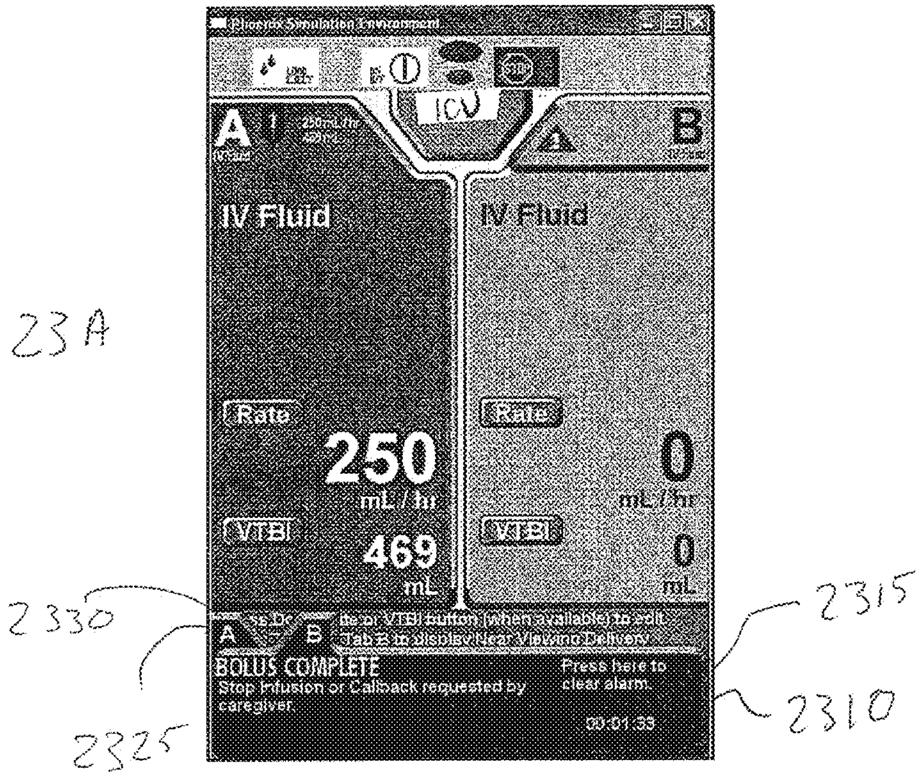
FIGS. 23A to 23C are screen shots illustrating graphical user interface alarm navigation shortcut buttons.
Figure 23B:
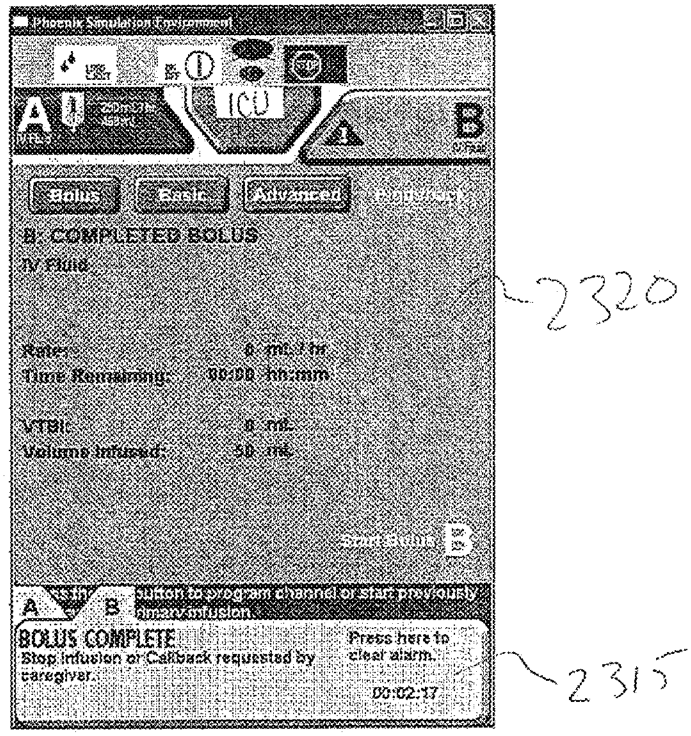
Figure 23C:
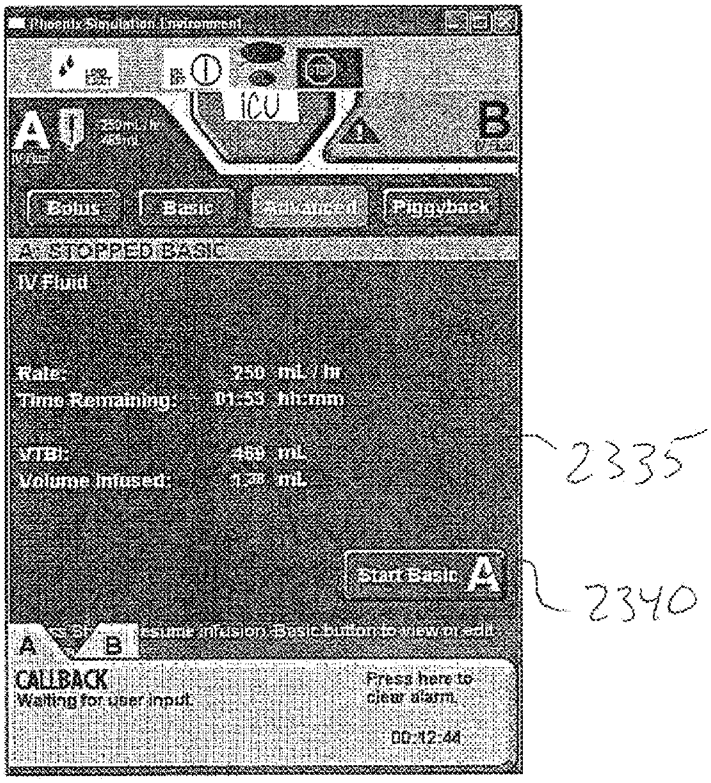

FIGS. 23A to 23C are screen shots of a display interface for a multi-channel infusion pump. In this example, the infusion pump has a therapy programmed for both channel A and channel B. Channel A is idle waiting for the bolus programmed on channel B to complete. FIG. 23A shows that an alarm 2310 has occurred on channel B based on the completion of the bolus infusion programmed on channel B. The drug library or the user had previously configured the pump to stop the infusion or request the pump generate a callback to them when the bolus was complete. When the user presses alarm tab B 2315 the user is taken directly to the display screen 2320 for channel B. Display screen for channel B indicates that the bolus is completed.

FIG. 23A also illustrates that an alarm 2325 has occurred for channel A When the user presses alarm tab A 2330, the user is taken directly to display screen 2335 shown in FIG. 23C. Display screen 2335 indicates to the user the pump is waiting for input from the user. The user must clear the alarm and provide the necessary input before the infusion scheduled on channel A may be started by pressing Start 2340. The ability for a user to navigate quickly to the cause of the alarm improves efficiency of the user as well as workflow. Additionally, the ability to navigate directly to the cause of the alarm decreases or eliminates errors that may occur if the user had to take many steps to navigate to the appropriate display screen.

Figure 24:
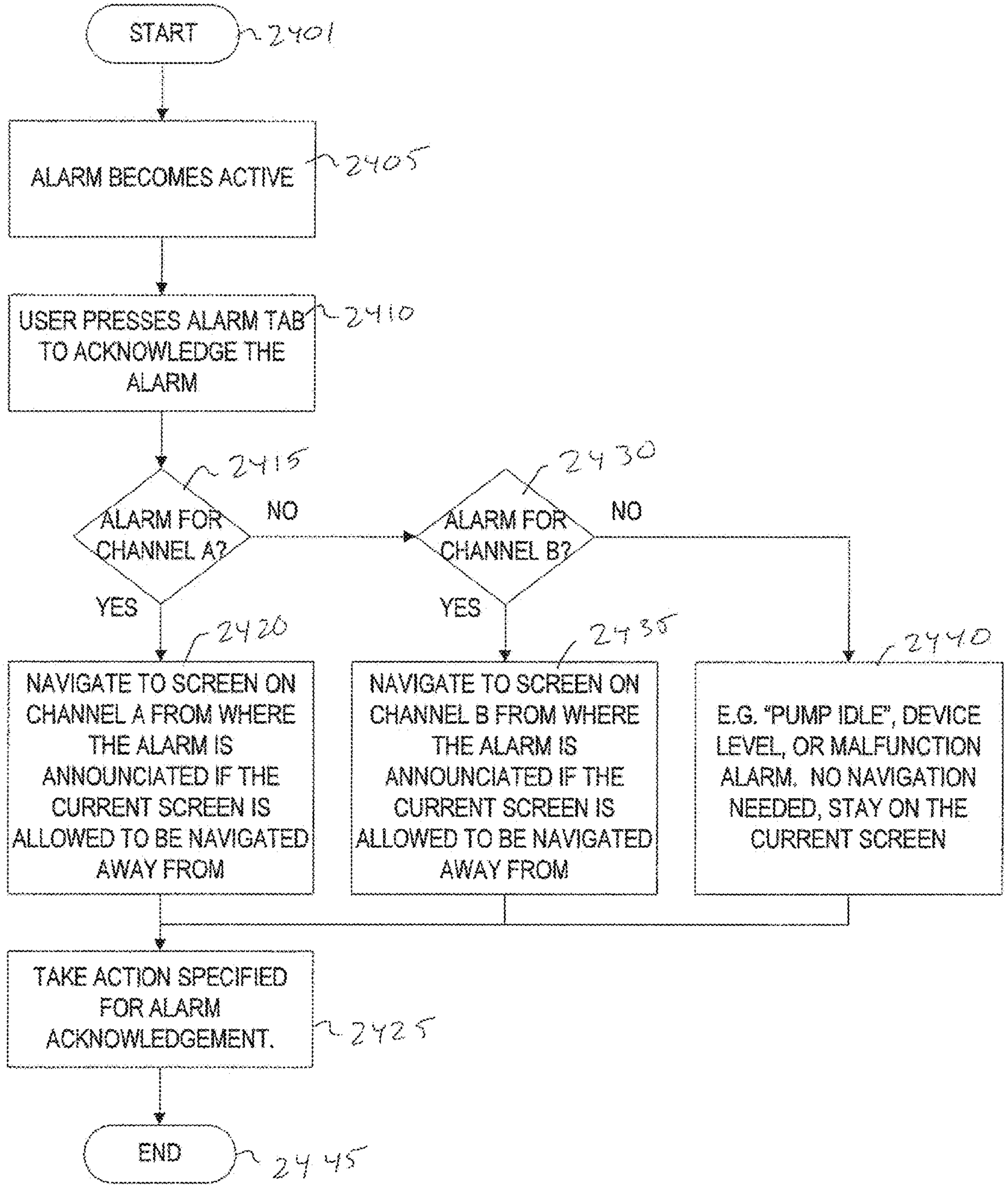
FIG. 24 is a flow chart for a program for determining a screen view display parameter based on the alarm navigation shortcut buttons.

With reference to FIG. 24, a flow chart for one embodiment for a program 2400 for navigating directly to a cause of an alarm is shown. Program 2400 begins at block 2401 and proceeds to block 2405 where an alarm has been activated. In response to the alarm, an acknowledgement is received from the user in response to the user pressing an alarm tab in block 2410. Program 2400 determines at block 2415 whether the alarm was for channel A If yes, the program proceeds to block 2420 where the program navigates to the screen on channel A from where the alarm is arising if the current screen is allowed to be navigated away from. At block 2425, the user takes appropriate action in relation to the alarm. If, at block 2415, the program determines that the alarm is not for channel A, program 2400 proceeds to block 2430 where it is determined whether the alarm is for channel B. If yes, the program proceeds to block 2435 where the program navigates to the screen on channel B from where the alarm is arising if the current screen is allowed to be navigated away from. If at block 2430, the alarm is not for channel B, program 2400 proceeds to block 2440. At block 2440, the program determines that no navigation is required and proceeds to block 2425 where the user is instructed to take a specific action. Program 2400 ends at 2445.

In another embodiment, the drug library may be configured to allow for a dose back calculation during the programming of an infusion delivery. During the programming of an infuser for a dose-based therapy (e.g. weight or BSA based therapy), the user must enter the dose first before being allowed to enter the rate. In certain clinical scenarios it is preferable for the user to enter the rate first and the dose is calculated from the rate. Providing this flexibility to the user and the hospital administration allows for increased efficiency and better work flow.

Figure 25:
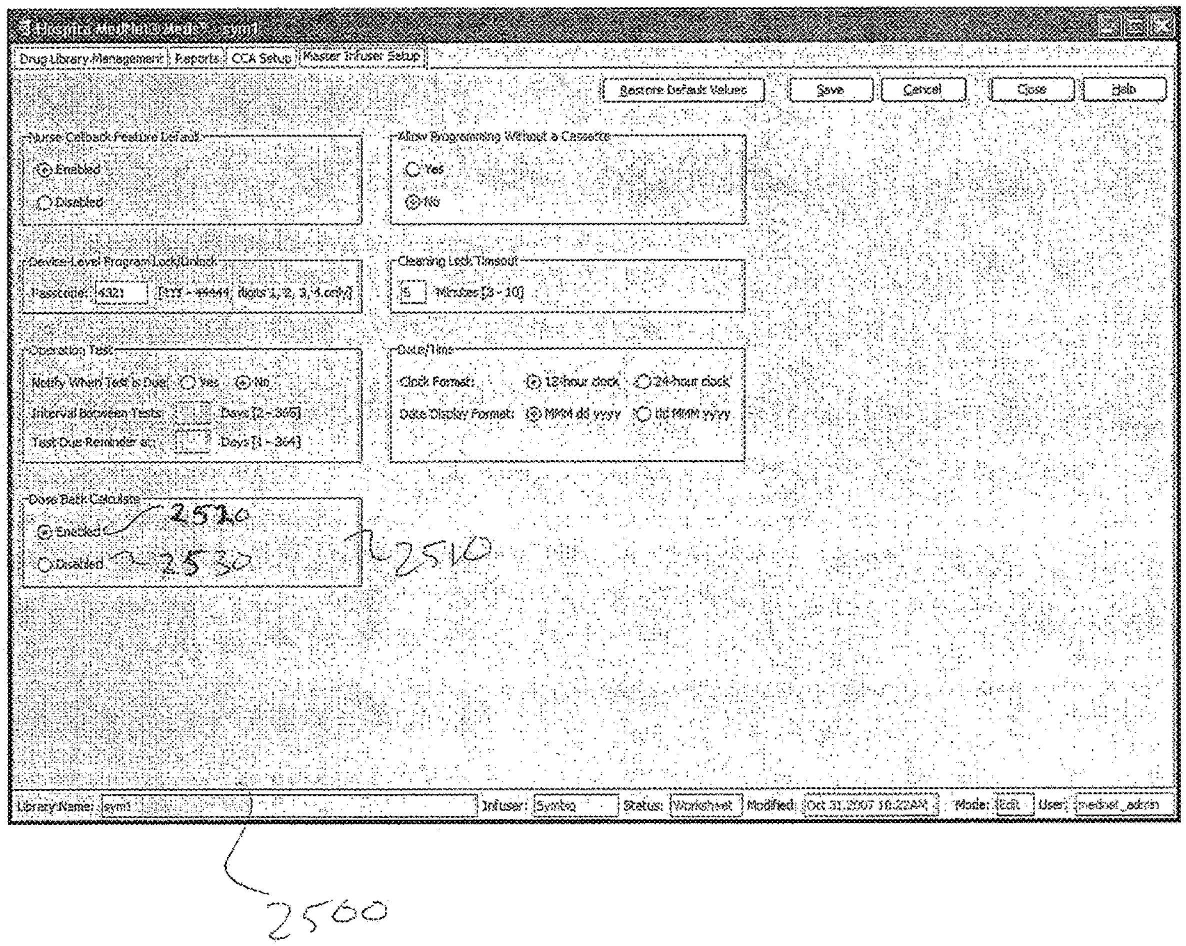
FIG. 25 is a screen shot of a graphical user interface for configuring a dose back calculation parameter at the drug library.

FIG. 25 illustrates a graphical user interface 2500 for configuring a drug library. A default "dose back calculate" can be set at 2510. To enable the dose back calculation at the medical device, an administrator selects "enabled" 2520. To disable the dose back calculation at the medical device, the administrator selects "disabled" 2530.

Figure 26A:
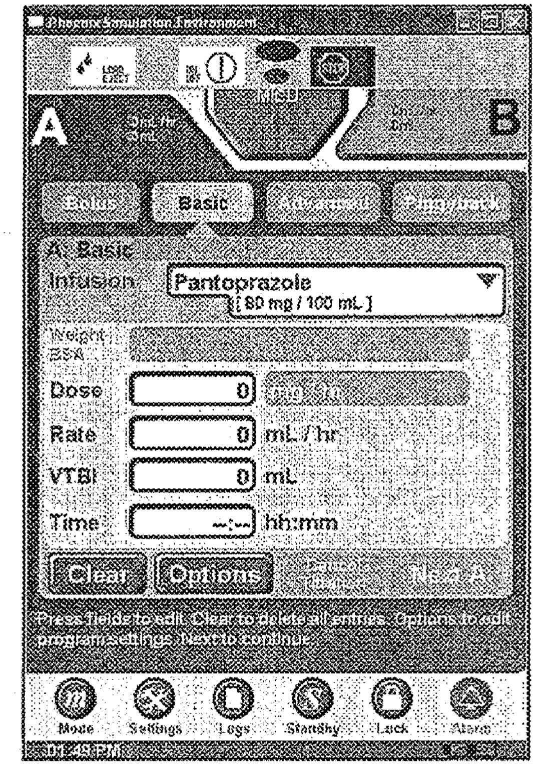
FIGS. 26A and 26B are screen shots of a graphical user interface for configuring a dose back calculation at the medical device.
Figure 26B:
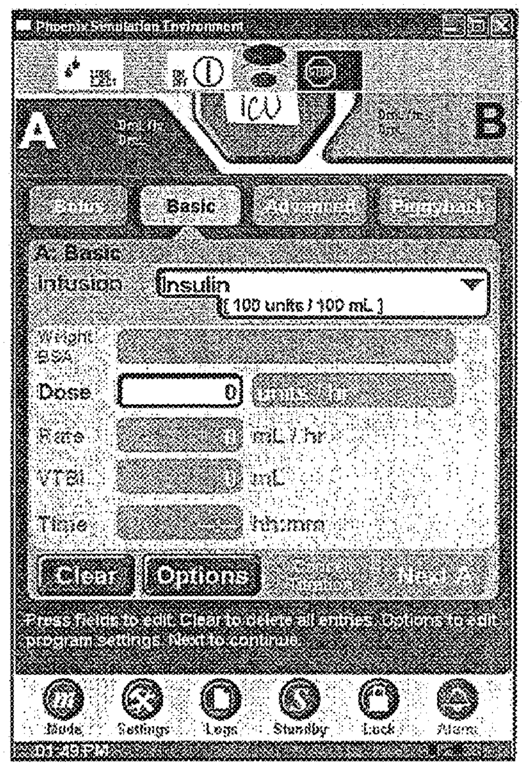

FIG. 26A is a screen shots of a medical device that allows for the dose back calculation as determined within the drug library. The user is allowed to enter dose, rate, etc. in any order as further described below. FIG. 26B is a screen shot of a medical device that disallows for the dose back calculation as determined within the drug library. The user is forced by the user interface to enter the dose first.

Figure 27:
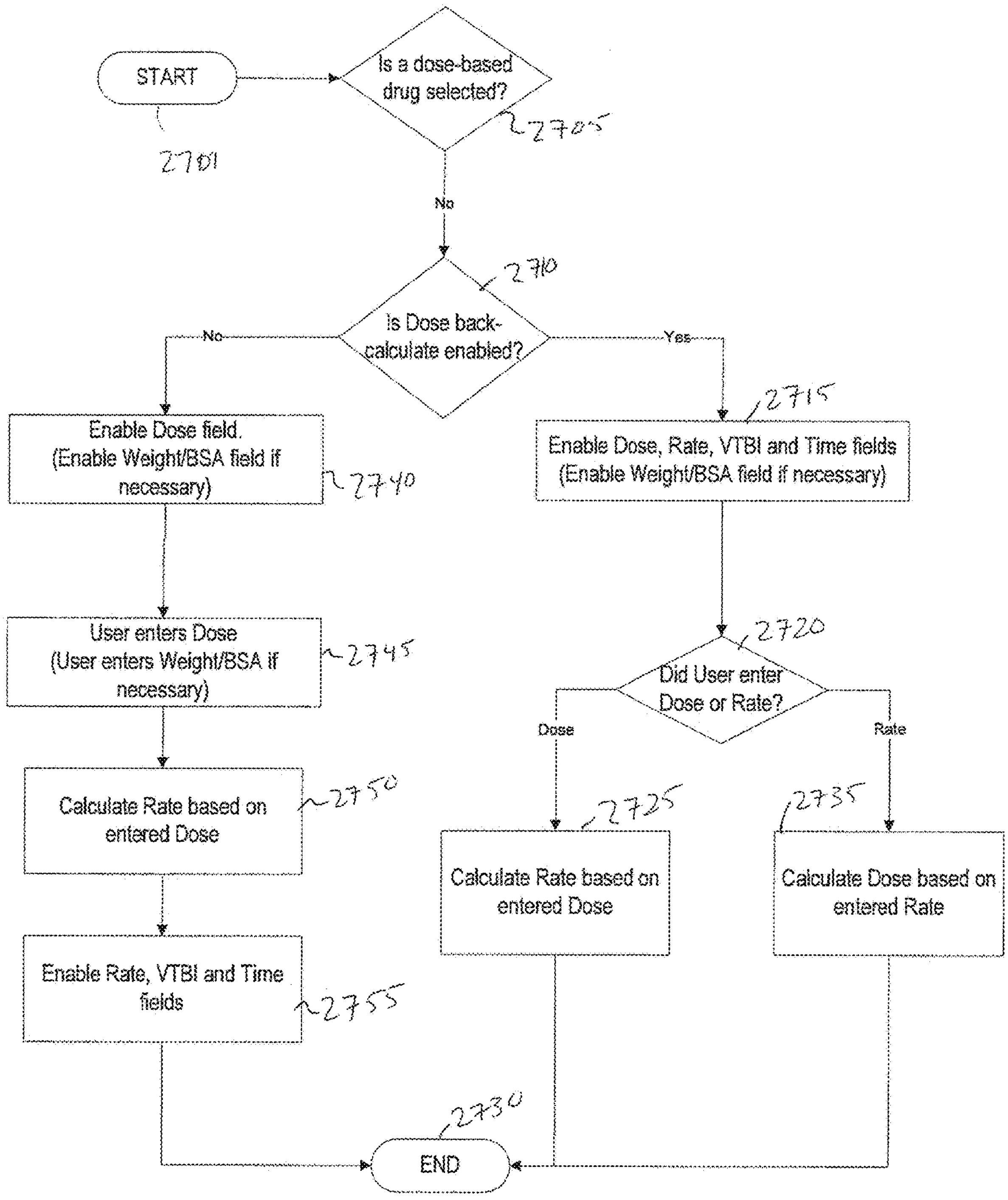
FIG. 27 is a flow chart for a program for allowing or disallowing a dose back calculation at the medical device.

With reference to FIG. 27, illustrated is a flow chart of a program 2700 residing in the medical device for programming a drug and calculating a dose. Program 2700 begins at 2701 and proceeds to block 2705 where the program determines if the user selected a dose-based drug. If not, program 2700 proceeds to block 2710 where program 2700 determines whether the dose back calculation is enabled at the drug library. If yes, program 2700 proceeds to block 2715, where program 2700 enables dose, rate, VTBI, time and/or weight/BSA fields. Program 2700 proceeds to 2720 where it is determined whether the user entered the dose or the rate. If dose, program 2700 proceeds to block 2725 to calculate rate based on the provided dose. If rate, program 2700 proceeds to block 2735 to calculate the dose based on the provided rate.

If at block 2710 the dose-back calculation is not enabled, program 2700 proceeds to block 27 40 where program 2700 enables a dose field as well as weight/BSA if required. Program 2700 proceeds to block 2745 where a dose is provided as well as weight/BSA if required. Next, a rate is calculated based on the entered dose. Program 2700 proceeds to block 2755 where rate, VTBI and time fields are enabled. Program 2700 ends at 2730.

One skilled in the art will appreciate from this disclosure that the functionality shown in the figures and described herein is made possible by computer program code, and as such those features could be combined, distributed or shared among the processors of the pump 14, the MMU 12, or other computers within the healthcare facility without detracting from the present invention. Those skilled in the art will also recognize from this disclosure that selecting the CCA and providing other information or input can be done via scanning or passively receiving input from drug containers, a patient identifier, a nurse identifier or other similar items.

While the embodiments of the invention disclosed herein are presently considered to be preferred, various changes and modifications can be made without departing from the scope of the invention. The scope of the invention is indicated in the appended claims, and all changes and modifications that come within the meaning and range of equivalents are intended to be embraced therein.

What is claimed is:

1. An infusion pump configured to convey medical fluid to a patient, the infusion pump comprising:

a processor;

a memory configured to store a drug library that includes a plurality of settings including medication parameters or limits;

first and second pump channels; and a display screen configured to display a plurality of drug infusion parameters;

wherein the display screen comprises a first pump channel screen portion and a second pump channel screen portion, the display screen being configured to display: (i) a designated clinical care area, and (ii) first and second machine readable indicia associated with the respective first and second pump channels;

wherein the infusion pump is configured to permit the clinical care area to be changed without stopping an ongoing infusion, from a first clinical care area associated with a first setting of the plurality of settings of the drug library to a second clinical care area associated with a second setting of the plurality of settings of the drug library that is different from the first setting;

wherein the infusion pump is configured to permit different clinical care areas to be designated for each of the first and second pump channels; and wherein the infusion pump is configured to communicate over a network with a medication management unit to receive drug library information.

2. The infusion pump of claim 1, wherein the first and second machine readable indicia comprise bar codes.

3. The infusion pump of claim 2, wherein the display screen is a color touch screen.

4. The infusion pump of claim 1, wherein the clinical care area can be changed without interrupting an ongoing infusion.

5. The infusion pump of claim 3, wherein the display screen is customizable depending on a chosen clinical care area.

6. The infusion pump of claim 1, wherein the plurality of drug infusion parameters include drug name, concentration, and dose rate.

7. The infusion pump of claim 1, wherein the plurality of drug infusion parameters include volume to be infused or volume remaining.

8. The infusion pump of claim 1, wherein the display screen is configured to provide a near view and a far view.

9. The infusion pump of claim 1, wherein the clinical care area is changeable while maintaining infusion parameters of an ongoing infusion.

10. An infusion pump configured to convey medical fluid to a patient, the infusion pump comprising:

a processor;

a memory configured to store a drug library that includes a plurality of settings including medication parameters or limits;

at least one pump channel; and a display screen configured to display a plurality of drug infusion parameters;

wherein the display screen is configured to display a designated clinical care area;

wherein the infusion pump is configured to permit the clinical care area to be changed without stopping an ongoing infusion, from a first clinical care area associated with a first setting of the plurality of settings of the drug library to a second clinical care area associated with a second setting of the plurality of settings of the drug library that is different from the first setting; and wherein the infusion pump is configured to communicate over a network with a medication management unit to receive drug library information.

11. The infusion pump of claim 10, further comprising machine readable indicia comprising a bar code.

12. The infusion pump of claim 10, wherein the display screen is a color touch screen.

13. The infusion pump of claim 10, wherein the clinical care area can be changed without interrupting an ongoing infusion.

14. The infusion pump of claim 10, wherein the display screen is customizable depending on a chosen clinical care area.

15. The infusion pump of claim 10, wherein the plurality of drug infusion parameters include drug name, concentration, and dose rate.

16. The infusion pump of claim 10, wherein the plurality of drug infusion parameters include volume to be infused or volume remaining.

17. The infusion pump of claim 10, wherein the display screen is configured to provide a near view and a far view.

18. The infusion pump of claim 10, wherein the clinical care area is changeable while maintaining infusion parameters of an ongoing infusion.

19. An infusion pump configured to convey medical fluid to a patient, the infusion pump comprising:

a processor;

a memory configured to store a drug library that includes a plurality of settings including medication parameters or limits;

at least one pump channel; and a display screen configured to display a plurality of drug infusion parameters;

wherein the infusion pump includes a setting for a clinical care area; and wherein the infusion pump is configured to permit the clinical care area to be changed without stopping an ongoing infusion, from a first clinical care area associated with a first setting of the plurality of settings of the drug library to a second clinical care area associated with a second setting of the plurality of settings of the drug library that is different from the first setting.

20. The infusion pump of claim 19, wherein the display screen is a color touch screen.

21. The infusion pump of claim 19, wherein the display screen is customizable depending on a chosen clinical care area.

22. The infusion pump of claim 19, wherein the plurality of drug infusion parameters include drug name, concentration, and dose rate.

23. The infusion pump of claim 19, wherein the plurality of drug infusion parameters include volume to be infused or volume remaining.

24. The infusion pump of claim 19, wherein the display screen is configured to provide a near view and a far view.

25. The infusion pump of claim 19, wherein the clinical care area is changeable while maintaining infusion parameters of an ongoing infusion.

26. The infusion pump of claim 19, wherein the infusion pump is configured to wait to change a setting associated with a clinical care area until the pump is idle.

27. The infusion pump of claim 1, wherein the infusion pump is configured to present a dialog box to the user to verify a change of clinical care area.

28. The infusion pump of claim 10, wherein the infusion pump is configured to wait until after an ongoing infusion is complete to implement the second setting.

29. The infusion pump of claim 19, wherein the infusion pump is configured to wait until after an ongoing infusion is complete to implement the second setting.

* * * * *